(12) United States Patent
Raksi et al.

(10) Patent No.: US 8,262,647 B2
(45) Date of Patent: Sep. 11, 2012

(54) OPTICAL SYSTEM FOR OPHTHALMIC SURGICAL LASER

(75) Inventors: Ferenc Raksi, Mission Viejo, CA (US); Jesse Buck, San Marcos, CA (US)

(73) Assignee: Alcon LenSx, Inc., Aliso Viejo, CA (US)

(*) Notice: Subject to any disclaimer, the term of this patent is extended or adjusted under 35 U.S.C. 154(b) by 676 days.

(21) Appl. No.: 12/511,974

(22) Filed: Jul. 29, 2009

(65) Prior Publication Data

US 2011/0028953 A1 Feb. 3, 2011

(51) Int. Cl.
*A61B 18/18* (2006.01)
*A61B 19/00* (2006.01)

(52) U.S. Cl. ............... 606/5; 606/4; 128/898

(58) Field of Classification Search ............ 606/4, 5, 606/17, 107; 128/898; 372/9
See application file for complete search history.

(56) References Cited

U.S. PATENT DOCUMENTS

| | | |
|---|---|---|
| 4,538,608 A | 9/1985 | L'Esperance, Jr. |
| 5,541,951 A | 7/1996 | Juhasz et al. |
| 5,548,234 A | 8/1996 | Turi et al. |
| 5,549,632 A | 8/1996 | Lai |
| 5,561,678 A | 10/1996 | Juhasz et al. |
| 5,656,186 A | 8/1997 | Mourou et al. |
| 6,081,543 A | 6/2000 | Liu et al. |
| 6,099,522 A | 8/2000 | Knopp et al. |
| 6,220,707 B1 | 4/2001 | Bille |
| 6,324,191 B1 | 11/2001 | Horvath |
| 6,610,050 B2 | 8/2003 | Bille |
| 6,610,051 B2 | 8/2003 | Bille |
| 6,693,927 B1 | 2/2004 | Horvath et al. |
| 6,726,680 B1 | 4/2004 | Knopp et al. |
| 6,746,121 B2 | 6/2004 | Ross et al. |
| 6,751,033 B2 | 6/2004 | Goldstein et al. |
| 6,908,196 B2 | 6/2005 | Herekar et al. |
| 6,992,765 B2 | 1/2006 | Horvath et al. |
| 7,027,233 B2 | 4/2006 | Goldstein et al. |
| 7,131,968 B2 | 11/2006 | Bendett et al. |
| 7,330,275 B2 | 2/2008 | Raksi |
| 7,390,089 B2 | 6/2008 | Loesel et al. |
| 7,452,080 B2 | 11/2008 | Wiltberger et al. |

(Continued)

FOREIGN PATENT DOCUMENTS

EP 1279386 1/2003

(Continued)

OTHER PUBLICATIONS

Wang et al., "High Focal Depth With a Pure-Phase Apodizer," Nov. 2001, Applied Optics, 40(31):5658-5662, 5 pages.

(Continued)

*Primary Examiner* — William Choi

(74) *Attorney, Agent, or Firm* — Gergely T. Zimanyi

(57) ABSTRACT

A laser system for ophthalmic surgery includes a laser source, to generate a pulsed laser beam, an XY scanner, to receive the pulsed laser beam, and to output an XY-scanning beam, scanned in two directions transverse to a Z axis, a Z scanner, to receive the XY-scanning beam, and to output an XYZ-scanning beam, scanned in addition along the Z axis, the Z scanner including a first lens group to output a beam having an intermediate focal plane, and a movable lens group to receive the beam through the intermediate focal plane and to collimate the beam in a variable manner, and an objective to receive the collimated beam from the Z scanner and to focus the beam into a focal spot in a target region.

22 Claims, 29 Drawing Sheets

First Beam Expander block 400    Movable Beam Expander block 500

U.S. PATENT DOCUMENTS

| | | |
|---|---|---|
| 7,452,081 B2 | 11/2008 | Wiltberger et al. |
| 7,522,642 B2 | 4/2009 | Zadoyan et al. |
| 7,584,756 B2 | 9/2009 | Zadoyan et al. |
| 7,597,444 B2 | 10/2009 | Rathjen et al. |
| 7,599,591 B2 | 10/2009 | Andersen et al. |
| 7,655,002 B2 | 2/2010 | Myers |
| 2003/0053219 A1 | 3/2003 | Manzi |
| 2004/0059321 A1 | 3/2004 | Knopp et al. |
| 2004/0254568 A1 | 12/2004 | Rathjen |
| 2005/0228366 A1 | 10/2005 | Kessler et al. |
| 2006/0084954 A1 | 4/2006 | Zadoyan et al. |
| 2006/0195076 A1 | 8/2006 | Blumenkranz et al. |
| 2007/0106285 A1 | 5/2007 | Raksi |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0173791 A1 | 7/2007 | Raksi |
| 2007/0173795 A1 | 7/2007 | Frey et al. |
| 2007/0173796 A1 | 7/2007 | Kessler et al. |
| 2007/0219541 A1 | 9/2007 | Kurtz |
| 2008/0033406 A1 | 2/2008 | Andersen et al. |
| 2008/0077121 A1 | 3/2008 | Rathjen |
| 2008/0147052 A1 | 6/2008 | Bendett et al. |
| 2008/0167642 A1 | 7/2008 | Palanker et al. |
| 2008/0228176 A1 | 9/2008 | Triebel et al. |
| 2008/0269731 A1 | 10/2008 | Swinger et al. |
| 2008/0281303 A1 | 11/2008 | Culbertson et al. |
| 2008/0319464 A1 | 12/2008 | Bischoff et al. |
| 2009/0012507 A1 | 1/2009 | Culbertson et al. |
| 2009/0118718 A1 | 5/2009 | Raksi et al. |
| 2009/0131921 A1 | 5/2009 | Kurtz et al. |
| 2009/0149841 A1 | 6/2009 | Kurtz |
| 2009/0171327 A1 | 7/2009 | Kurtz et al. |
| 2010/0004641 A1 | 1/2010 | Frey et al. |

FOREIGN PATENT DOCUMENTS

| | | |
|---|---|---|
| EP | 1584310 | 10/2005 |
| WO | 98/56298 | 12/1998 |
| WO | 2007056486 | 5/2007 |
| WO | 2009089504 | 7/2009 |

OTHER PUBLICATIONS

Jenkins et al., "Fundamentals of Optics," 4th Edition, 2001, pp. 190-191.

Duma et al., "Determination of Significant Parameters for Eye Injury Risk from Projectiles", Oct. 2005; Journal of Trauma Injury, Infection, and Critical Care, 59(4):960-4, 5 pages.

Gwon et al., "Focal laser photophacoablation of normal and cataractous lenses in rabbits: Preliminary report," May 1995, J. Cataract Refract Surg. 21, 282-286, 5 pages.

Kim, Sang Woo, Authorized Office, Korean Intellectual Property Office, PCT International Application No. PCT/US2010/042777, in International Search Report mailed Mar. 25, 2011, 10 pages.

Kim, Sang Woo, Authorized Office, Korean Intellectual Property Office, PCT International Application No. PCT/US2010/042791, in International Search Report mailed Mar. 25, 2011, 14 pages.

Kim, Sang Woo, Authorized Office, Korean Intellectual Property Office, PCT International Application No. PCT/US2010/042787, in International Search Report mailed Mar. 25, 2011, 11 pages.

Kim, Sang Woo, Authorized Office, Korean Intellectual Property Office, PCT International Application No. PCT/US2010/042796, in International Search Report mailed Mar. 28, 2011, 11 pages.

Kim, Sang Woo, Authorized Office, Korean Intellectual Property Office, PCT International Application No. PCT/US2010/042804, in International Search Report mailed Mar. 30, 2011, 8 pages.

Kim, Sang Woo, Authorized Office, Korean Intellectual Property Office, PCT International Application No. PCT/US2010/042800, in International Search Report mailed Mar. 30, 2011, 9 pages.

Kruger et al., "Experimental Increase in Accommodative Potential after Neodymium: Yttrium-Aluminum-Garnet Laser," Jun. 2001, Ophthalmology 108: 2122-2129, 8 pages.

Kurtz et al., "Precise Targeting of Surgical Photodisruption," Co-pending US Appl. No. 12/205,844, filed Sep. 5, 2008, to be published by the USPTO, 72 pages.

Ryan et al., "Nd:YAG Laser Photodisruption of the Lens Nucleus Before Phacoemulsification," Oct. 1987, Americal Journal of Ophthalmology 104: 382-386, 5 pages.

Hyun, Seung Hoon, Authorized Officer, Korean Intellectual Property Office, PCT International Application No. PCT/US2010/042786, in International Search Report, mailed Apr. 25, 2011, 9 pages.

Hyun, Seung Hoon, Authorized Officer, Korean Intellectual Property Office, PCT International Application No. PCT/US2010/042960, in International Search Report, mailed Apr. 25, 2011, 9 pages.

Hyun, Seung Hoon, Authorized Officer, Korean Intellectual Property Office, PCT International Application No. PCT/US2010/042964, in International Search Report, mailed Apr. 25, 2011, 9 pages.

Jang, Jung Suk, Authorized Officer, Korean Intellectual Property Office, PCT International Application No. PCT/US2010/055968, in International Search Report, mailed Jul. 6, 2011, 9 pages.

Hyun, Seung Hoon, Authorized Officer, Korean Intellectual Property Office, PCT International Application No. PCT/US2010/042957, in International Search Report, mailed Apr. 25, 2011, 9 pages.

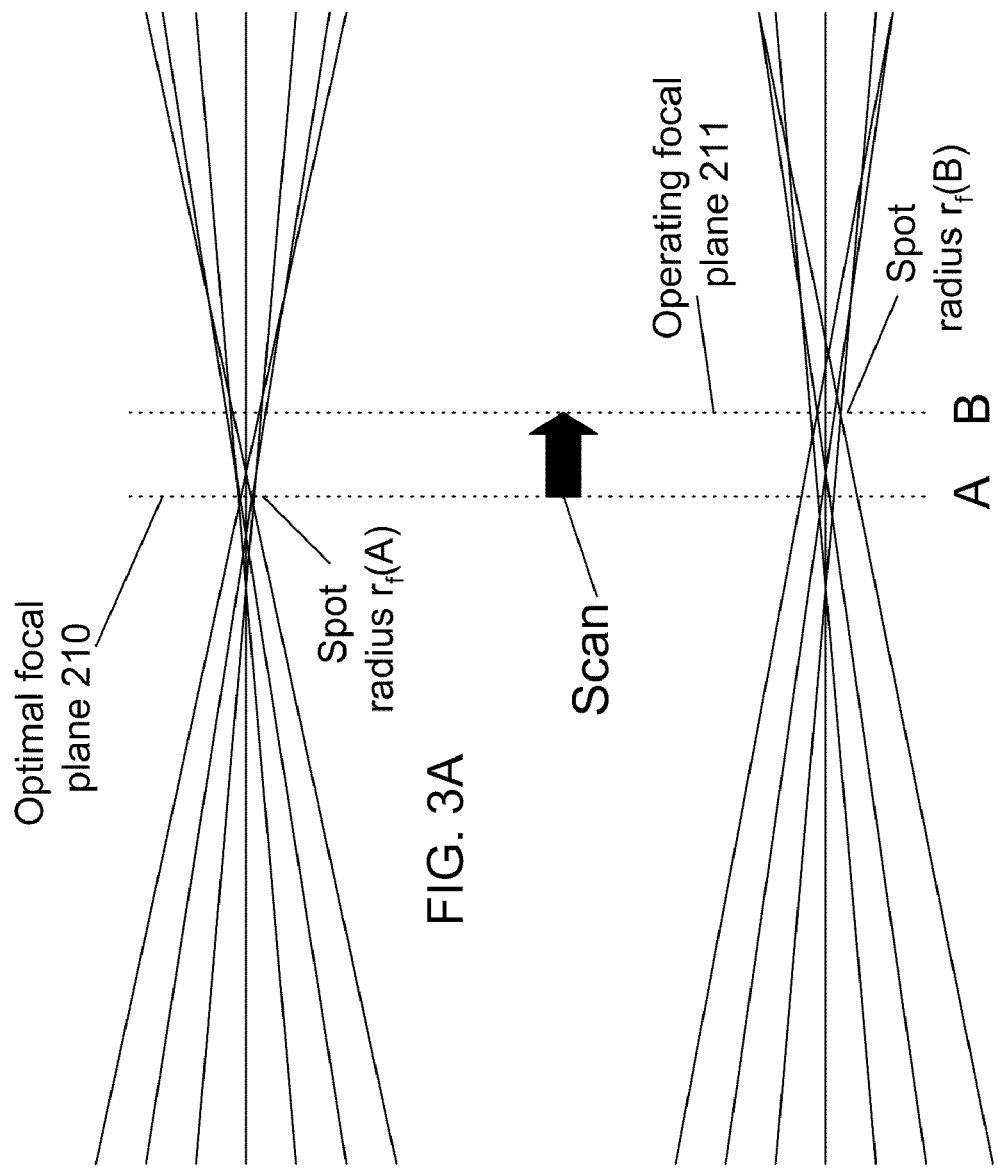

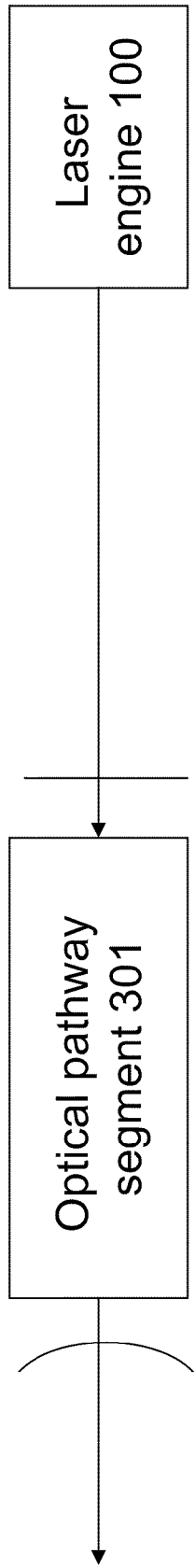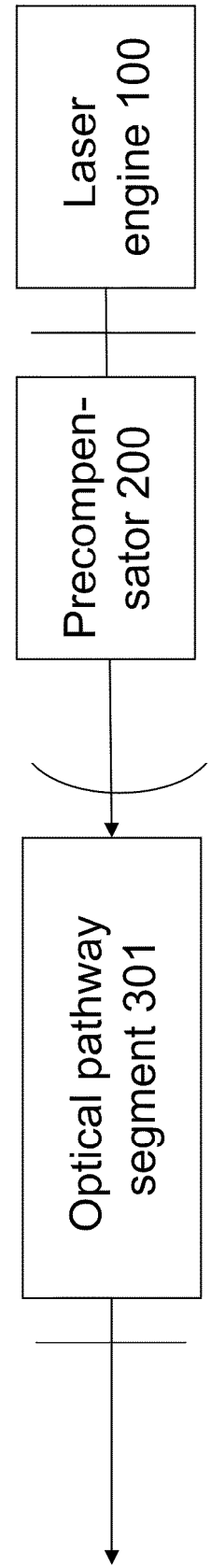

|  | 0 NA adjuster | 1 NA controller before XY scanner | 1 NA controller after XY scanner | 2 NA controllers |
|---|---|---|---|---|
| 0 Z depth scanner (fixed Z depth) |  | Controls NA during XY scanning | Controls NA during XY scanning | Controls NA during XY scanning |
| 1 Z depth scanner before XY scanner | Z scans | - Z scans<br>- Controls NA | - Z scans<br>- Controls NA | - Z scans<br>- Controls NA |
| 1 Z depth scanner after XY scanner | Z scans | - Z scans<br>- Controls NA | - Z scans<br>- Controls NA | - Z scans<br>- Controls NA |
| 2 Z depth scanners | Z scans at two speeds | - Z scans at two speeds<br>- Controls NA | - Z scans at two speeds<br>- Controls NA | - Z scans at two speeds<br>- Controls NA |

FIG. 10

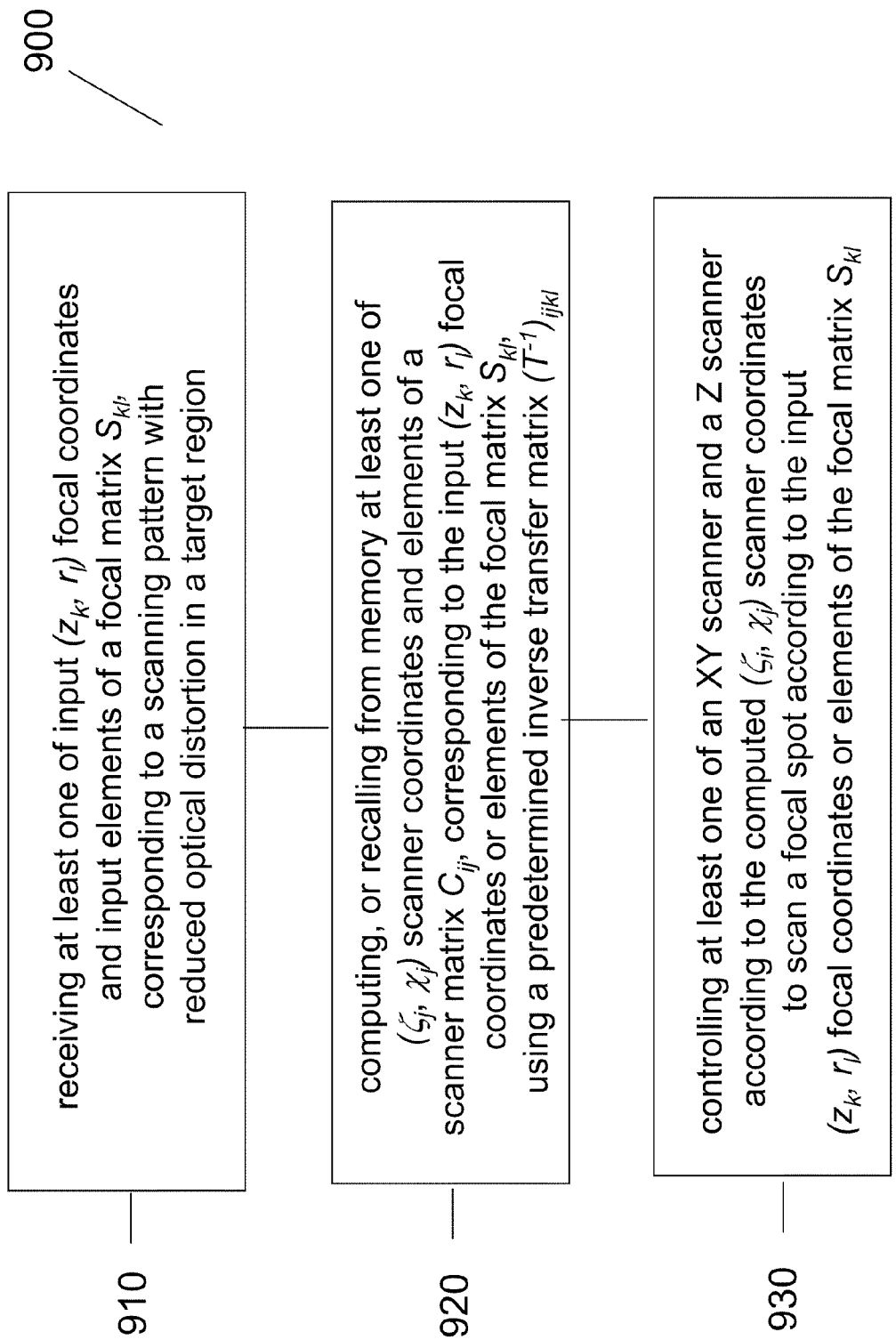

OPTICAL SYSTEM FOR OPHTHALMIC SURGICAL LASER

FIELD OF INVENTION

This invention relates to a system for surgery of the anterior segment of the eye with a femtosecond laser, more particularly to embodiments minimizing optical distortions of the laser beam while scanning and focusing the laser beam into the eye.

BACKGROUND

This application describes examples and embodiments of techniques and systems for laser surgery within the anterior segment of the eye the crystalline lens via photodisruption caused by laser pulses. Various lens surgical procedures for removal of the crystalline lens utilize various techniques to break up the lens into small fragments that can be removed from the eye through small incisions. These procedures use manual instruments, ultrasound, heated fluids or lasers and tend to have significant drawbacks, including the need to enter the eye with probes in order to accomplish the fragmentation, and the limited precision associated with such lens fragmentation techniques.

Photodisruptive laser technology can deliver laser pulses into the lens to optically fragment the lens without insertion of a probe and thus can offer the potential for improved lens removal. Laser-induced photodisruption has been widely used in laser ophthalmic surgery and Nd:YAG lasers have been frequently used as the laser sources, including lens fragmentation via laser induced photodisruption. Some existing systems utilize nanosecond lasers with pulse energies of several mJ (E. H. Ryan et al. American Journal of Opthalmology 104: 382-386, October 1987; R. R. Kruger et al. Opthalmology 108: 2122-2129, 2001), and picosecond lasers with several tens of µJ (A. Gwon et al. J. Cataract Refract Surg. 21, 282-286, 1995). These relatively long pulses deposit relatively large amounts of energy into the surgical spots, resulting in considerable limitations on the precision and control of the procedure, while creating a relatively high level of risk of unwanted outcomes.

In parallel, in the related field of cornea surgery it was recognized that shorter pulse durations and better focusing can be achieved by using pulses of duration of hundreds of femtoseconds instead of the nanosecond and picosecond pulses. Femtosecond pulses deposit much less energy per pulse, significantly increasing the precision and the safety of the procedure.

Presently several companies commercialize femtosecond laser technology for ophthalmic procedures on the cornea, such as LASIK flaps and corneal transplants. These companies include Intralase Corp./Advanced Medical Optics, USA, 20/10 Perfect Vision Optische Geräte GmbH, Germany, Carl Zeiss Meditec, Inc. Germany, and Ziemer Ophthalmic Systems AG, Switzerland.

However, these systems are designed according to the requirements of the cornea surgery. Crucially, the depth range of the laser focus is typically less than about 1 mm, the thickness of the cornea. As such, these designs do not offer solutions for the considerable challenges of performing surgery on the lens of the eye.

SUMMARY

Briefly and generally, a laser system for ophthalmic surgery includes a laser source, to generate a pulsed laser beam, an XY scanner, to receive the pulsed laser beam, and to output an XY-scanning beam, scanned in two directions transverse to a Z axis, a Z scanner, to receive the XY-scanning beam, and to output an XYZ-scanning beam, scanned in addition along the Z axis, the Z scanner including a first lens group to output a beam having an intermediate focal plane, and a movable lens group to receive the beam through the intermediate focal plane and to collimate the beam in a variable manner, and an objective to receive the collimated beam from the Z scanner and to focus the beam into a focal spot in a target region.

In some implementations the Z scanner is configured to scan a Z focal depth of the focal spot in the target region within a Z scanning range of 5 millimeter to 10 millimeter. In some implementations the Z scanner is configured to scan a Z focal depth of the focal spot in the target region within a Z scanning range of 0 millimeter to 15 millimeter.

In some implementations the movable lens group can be moved along the Z axis by a distance between 5 and 50 millimeters.

In some implementations the first lens group includes 2-10 lenses, and the movable lens group includes 2-10 lenses.

In some implementations the first lens group includes, sequentially from an input side a first lens group with a positive refractive power, a meniscus lens, having a convex surface facing the input side, and a second lens, having a concave surface facing the input side.

In some implementations the movable lens group includes, sequentially from an input side, a meniscus lens, having a concave surface facing the input side, a negative lens with a negative refractive power, and a positive lens group with a positive refractive power.

In some implementations the movable lens group is adjustable to change at least one characteristic of the XYZ scanning beam exiting the Z scanner, the characteristics including a convergence, a beam diameter, a Z focal depth, and a numerical aperture NA.

In some implementations the movable lens group is configured to adjust a numerical aperture NA and a Z focal depth of the XYZ scanning beam essentially independently from each other.

In some implementations the Z scanner is configured to focus a beam, emanating from an exit pivot point of the XY scanner into an entrance pivot point of the objective.

In some implementations the entrance pivot point of the objective is inside the objective. In some implementations a position of the entrance pivot point of the objective is adjustable by moving the movable lens group.

In some implementations the Z scanner is configured to modify an exit pivot point of the XY scanner into an entrance pivot point of the objective. In some implementations the entrance pivot point of the objective is inside the objective.

In some implementations the first lens group is one of a movable lens group and a fixed lens group.

In some implementations a method of ophthalmic surgery includes generating a pulsed laser beam, XY scanning the pulsed laser beam in two directions transverse to a Z direction with an XY scanner, Z scanning the XY scanned beam along a Z direction with a Z scanner by focusing the XY scanned beam onto an intermediate focal plane with a first lens group, receiving the beam from the intermediate focal plane by a movable beam scanner, collimating the beam into an adjustable entrance pivot point of an objective by the movable beam scanner, and focusing the beam onto an XYZ scanned focal spot in a target region by the objective.

In some implementations the Z scanning step includes adjusting the movable beam scanner to change at least one characteristic of the XYZ scanning beam exiting the Z scanner, the characteristics including a convergence, a beam diameter, a Z focal depth, and a numerical aperture NA.

In some implementations the Z scanning step includes adjusting a numerical aperture NA and a Z focal depth of the XYZ scanning beam essentially independently from each other.

BRIEF DESCRIPTION OF FIGURES

FIGS. 3A-B illustrate rays at an optimal and a scanned focal plane.

FIGS. 6A-B illustrate conceptually the operation of precompensator 200.

FIG. 10 illustrates a table of configurations containing 0, 1, or 2 Z depth Scanner and 0, 1, or 2 NA modifiers.

FIG. 19 illustrates steps of a computational control method.

DETAILED DESCRIPTION

Figure 1:
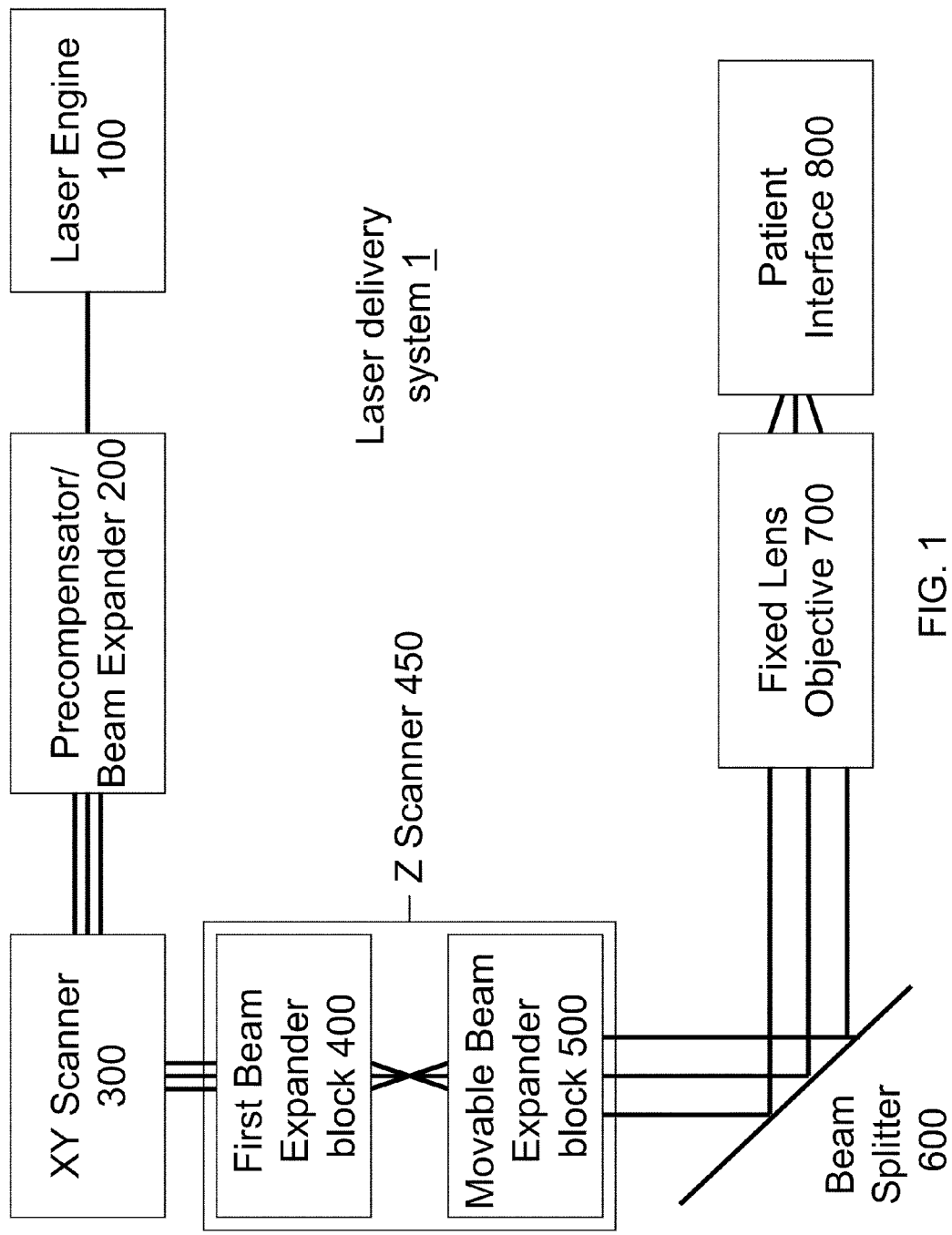
FIG. 1 illustrates a surgical laser delivery system 1.

Some embodiments of the present invention include systems for surgery in the lens of the eye, utilizing femtosecond laser pulses. Some integrated embodiments are also capable of performing both corneal and lens surgical procedures. Performing ophthalmic surgery in the lens of the eye is associated with qualitatively different requirements than corneal procedures.

The key differences between the presently described lens surgical laser system and corneal systems include:

1. Femtosecond laser pulses are to be generated reliably. High repetition rate femtosecond pulses allow the use of a much smaller energy per pulse, providing much higher control and precision for the operator of the system. However, generating femtosecond pulses reliably is a considerably greater challenge than nanosecond or picosend pulses, used by some existing systems.

2. The surgical laser beam is refracted considerably when propagating through up to 5 millimeters of refractive medium, including the cornea and the anterior aqueous chamber just to reach the surgical target, the lens. In contrast, the laser beam used for corneal surgery is focused at a depth of a fraction of a millimeter, and is thus essentially not refracted as it enters the cornea from the surgical system.

3. The surgical laser delivery system is configured to scan the entire surgical region, for example from the front/anterior of the lens at a typical depth of 5 mm to the back/posterior of the lens at a typical depth of 10 mm. This 5 mm or more depth-scanning range, or "Z scanning range", is considerably more extensive than the 1 mm depth-scanning range used for surgery on the cornea. Typically, the surgical optics, especially the here-used high numerical aperture optics, is optimized to focus a laser beam to a specific operating depth. During corneal procedures the 1 mm depth-scanning causes only moderate departure from the optimized operating depth. In contrast, during the scan from 5 to 10 mm during lens surgery, the system is driven far from a fixed optimized operating depth. Therefore, the lens-surgical laser delivery system employs a much-refined adaptive optics to be able to scan the extensive depth-scanning range required by lens surgery.

4. Some embodiments are integrated in the sense that they are configured to perform surgery on both the cornea and the lens. In these integrated embodiments the depth-scanning range can be up to 10 mm instead of 5 mm, posing even harder challenges.

5. During corneal surgical procedures, such as the many variants of LASIK, the laser beam is scanned perpendicular to the optical axis ("in the XY plane"). In typical procedures the XY scanning range covers only the central portion of the cornea with a diameter of 10 mm. However, in integrated surgical systems additional cuts may be formed as well. One type of cuts is the entry cuts, providing access to the inside of the eye for aspiration needles and conventional surgical tools. Another type of cuts is the limbal relaxing incisions (LRIs), which involve making a pair of incisions at the corneal limbus just anterior to the vascular arcade. By adjusting the length, depth, and location of these arcuate incisions, one can induce changes in the corneal astigmatism. Entry cuts and LRIs can be placed at the periphery of the cornea, typically with a diameter of 12 mm. While increasing the XY scanning diameter from 10 mm to 12 mm diameter is only a 20% increase compared to the regular diameter of LASIK flaps, it is a significant challenge to keep off-axis aberrations of the laser delivery system under control at such diameters, since off-axis aberrations grow proportional to higher powers of the field diameter at the focal plane.

6. Lens laser surgical procedures may require guidance from sophisticated imaging systems. In some imaging systems limbal blood vessels are identified to serve as reference marks on the eye, to calibrate the cyclo-rotational alignment of the eye during the time of surgery, in some cases relative to the reference coordinates identified during preoperative diagnosis of the eye. Blood vessels chosen on the periphery of the surgical area can be the most undisturbed by the surgery and thus the most reliable. Imaging systems directed to such peripheral blood vessels, however, require the imaging optics to image an area with a radius larger than 10 mm, such as 12 mm.

7. The laser beam develops various aberrations while propagating along the optical path within the eye. Laser delivery systems can improve precision by compensating for these aberrations. An additional aspect of these aberrations is that they depend on the frequency of the light, a fact referenced as "chromatic aberration". Compensating these frequency dependent aberrations increases the challenge on the system. The difficulty of compensating these chromatic aberrations increases with the bandwidth of the laser beam. a laser system. It is recalled that the spectral bandwidth of a beam is inversely proportional to the pulse length. Accordingly, the bandwidth for femtosecond pulses is often greater than that of picosecond pulses by an order of magnitude or more, necessitating a much better chromatic compensation in femtosecond laser systems.

8. Surgical procedures using high repetition rate femtosecond laser surgical systems require high precision in positioning each pulse both in an absolute sense with respect to target locations in the target tissue and in a relative sense with respect to preceding pulses. For example, the laser system may be required to redirect the beam by only a few microns within the time between pulses, which can be of the order of microseconds. Because the time between two subsequent pulses is short and the precision requirement for the pulse placement is high, manual targeting as used in existing low repetition rate lens surgical systems is no longer adequate or feasible.

9. The laser delivery system is configured to deliver the femtoscond laser pulses into the entire surgical volume of lens of the eye, through a refractive medium, with their temporal, spectral and spatial integrity preserved.

10. To ensure that only tissue in the surgical region receives a laser beam with high enough energy densities to cause surgical effects, such as tissue ablation, the laser delivery system has an unusually high numerical aperture (NA). This high NA results in small spot sizes and provides necessary control and precision for the surgical procedure. Typical ranges for the numerical aperture can include NA values larger than 0.3, resulting in spot sizes of 3 microns or less.

11. Given the complexity of the optical path of the laser for lens surgery, the laser delivery system achieves high precision and control by including a high performance computer-managed imaging system, whereas corneal surgical systems can achieve satisfactory control without such imaging systems, or with a low level of imaging. Notably, surgical and imaging functions of the system, as well as the customary observational beams generally all operate in different spectral bands. As an example, surgical lasers may operate at wavelengths in the band of 1.0-1.1 micron, observational beams in the visible band of 0.4-0.7 micron, and imaging beams in the band of 0.8-0.9 micron. Combining beam paths in common, or shared, optical components places demanding chromatic requirements on the optics of the laser surgical system.

The differences 1-11 illustrate through several examples that ophthalmic laser surgery (i) on the lens (ii) with femtosecond pulses introduces requirements which are qualitatively different from those of corneal surgery and even from lens surgery, using only nanosecond or picosecond laser pulses.

FIG. 1 illustrates a laser delivery system 1. Before describing it in detail, we mention that some embodiments combine the laser delivery system of FIG. 1 with an imaging or an observational system. In some corneal procedures, such as in LASIK treatments, eye trackers establish positional references of the eye by visual clues such an identification of the center of the iris by imaging and image processing algorithms, typically on the surface of the eye. However, existing eye trackers recognize and analyze features in a two-dimensional space, lacking depth information, since the surgical procedures are performed on the cornea, the outermost layer of the eye. Often, the cornea is even flattened to make the surface truly two dimensional.

The situation is quite different when focusing a laser beam in the lens, deep inside the eye. The crystalline lens can change its position, shape, thickness and diameter during accommodation, not only between prior measurement and surgery but also during surgery. Attaching the eye to the surgical instrument by mechanical means can also change the shape of the eye in an ill-defined manner. Such attaching devices can include fixating the eye with a suction ring, or aplanating the eye with a flat or curved lens. Further, the movement of the patient during surgery can introduce additional changes. These changes can add up to as much as a few millimeters of displacement of visual clues within the eye. Therefore, mechanically referencing and fixating the surface of the eye such as the anterior surface of the cornea or limbus are unsatisfactory when performing precision laser surgery on the lens or other internal portions of the eye.

To address this problem, laser delivery system 1 can be combined with an imaging system, as described in co-pending application serial number U.S. patent application Ser. No. 12/205,844 to R. M. Kurtz, F. Raksi and M. Karavitis, which is hereby incorporated by reference in its entirety. The imaging system is configured to image portions of a surgical region to establish three dimensional positional references based on the internal features of the eye. These images can be created before the surgery and updated in parallel with the surgical procedure to account for individual variations and changes. The images can be used to direct the laser beam safely to the desired location with high precision and control.

In some implementations, the imaging system can be an Optical Coherence Tomography (OCT) system. The imaging beam of the imaging system can have a separate imaging optical path, or an optical path partially or fully shared with the surgical beam. Imaging systems with a partially or fully shared optical path reduce the cost and simplify the calibration of the imaging and surgical systems. The imaging system can also use the same or a different light source as the laser of the laser delivery system 1. The imaging system can also have its own beam scanning subsystems, or can make use of the scanning subsystems of the laser delivery system 1. Several different architectures of such OCT systems are described in the referred co-pending application.

The laser delivery system 1 can be also implemented in combination with a visual observation optics. The observation optics can help the operator of the surgical laser to observe the effects of the surgical laser beam and control the beam in response to the observations.

Finally, in some implementations, which use an infrared and thus invisible surgical laser beam, an additional tracking laser may be employed operating at visible frequencies. The visible tracking laser may be implemented to track the path of the infrared surgical laser. The tracking laser may be operated at a low enough energy not to cause any disruption of the target tissue. The observation optics may be configured to direct the tracking laser, reflected from the target tissue, to the operator of the laser delivery system 1.

In FIG. 1, the beams associated with the imaging system and the visual observation optics can be coupled into the laser delivery system 1 e.g. through a beam splitter/dichroic mirror 600. The present application will not discuss extensively the various combinations of the laser delivery system 1 with the imaging, observational and tracking systems. The large number of such combinations, extensively discussed in the incorporated U.S. patent application Ser. No. 12/205,844, are all within the overall scope of the present application.

FIG. 1 illustrates a laser delivery system 1, which includes a Laser Engine 100, a Precompensator 200, an XY Scanner 300, a First Beam Expander block 400, a Movable Beam Expander block 500, a Beam Splitter/dichroic mirror 600, an Objective 700 and a Patient Interface 800, wherein the First Beam Expander block 400 and the Movable Beam Expander block 500 will be jointly referred to as Z Scanner 450.

In many implementations below the convention is used that the Z direction is the direction essentially along the optical path of the laser beam, or along the optical axis of the optical element. The directions transverse to the Z direction are referred to as XY directions. The term transverse is used in a broader sense to include that in some implementations the transverse and Z directions may not be strictly perpendicular to each other. In some implementations the transverse directions can be better described in terms of radial coordinates. Thus the terms transverse, XY, or radial directions denote analogous directions in the described implementations, all approximately (but necessarily precisely) perpendicular to the Z direction.

1. Laser Engine 100

The laser engine 100 can include a laser to emit laser pulses with predetermined laser parameters. These laser parameters may include pulse duration in the 1 femtosecond to 100 picosecond range, or within the 10 femtosecond to 10 picosecond range, or in some embodiments the 100 femtosecond to 1 picosecond range. The laser pulses can have an energy per pulse in the 0.1 microJoule to 1000 microJoule range, in other embodiments in the 1 microJoule to 100 microJoule range. The pulses can have a repeat frequency in the 10 kHz to 100 MHz range, in other embodiments in the 100 kHz to 1 MHz range. Other embodiments may have laser parameters which fall within a combination of these range limits, such as a range of pulse duration of 1-1000 femtosecond. The laser parameters for a particular procedure can be selected within these wide ranges e.g. during a pre-operational procedure, or based on a calculation which is based on certain data of the patient, such as his/her age.

Examples of the laser engine 100 can include Nd:glass and Nd:Yag lasers, and other lasers of a wide variety. The operating wavelength of the laser engine can be in the infrared or in the visible range. In some embodiments the operating wavelength can be in the 700 nm-2 micron range. In some cases the operating wavelength can be in the 1.0-1.1 micron range, e.g. in infrared lasers based on Yb or Nd.

In some implementations the laser parameters of the laser pulses may be adjustable and variable. The laser parameters may be adjustable with a short switch time, thus enabling the operator of the surgical laser delivery system 1 to change laser parameters during a complex surgery. Such a change of parameters can be initiated in response to a reading by a sensing or imaging subsystem of the laser delivery system 1.

Other parameter changes can be performed as part of a multi-step procedure during which the laser delivery system may be first used for a first surgical procedure, followed by a second, different surgical procedure. Examples include first performing one or more surgical steps in a region of a lens of an eye, such as a capsulotomy step, followed by a second surgical procedure in a corneal region of the eye. These procedures can be performed in various sequences.

High repetition rate pulsed lasers operating at a pulse repetition rate of tens to hundreds of thousands of shots per second or higher with relatively low energy per pulse can be used for surgical applications to achieve certain advantages. Such lasers use relatively low energy per pulse to localize the tissue effect caused by the laser-induced photodisruption. In some implementations, for example, the extent of the disrupted tissue can be limited to a few microns or a few tens of microns. This localized tissue effect can improve the precision of the laser surgery and can be desirable in certain surgical procedures. In various implementations of such surgeries, many hundreds, thousands or millions of pulses can be delivered to a sequence of spots which are contiguous, nearly contiguous, or are separated by controlled distances. These implementations can achieve certain desired surgical effects, such as tissue incisions, separations or fragmentation.

The parameters of the pulses and the scan pattern can be selected by various methods. For example, they can be based on a preoperative measurement of the optical or structural properties of the lens. The laser energy and the spot separation can also be selected based on a preoperative measurement of optical or structural properties of the lens or on an age-dependent algorithm.

2. Precompensator 200

Figure 2:
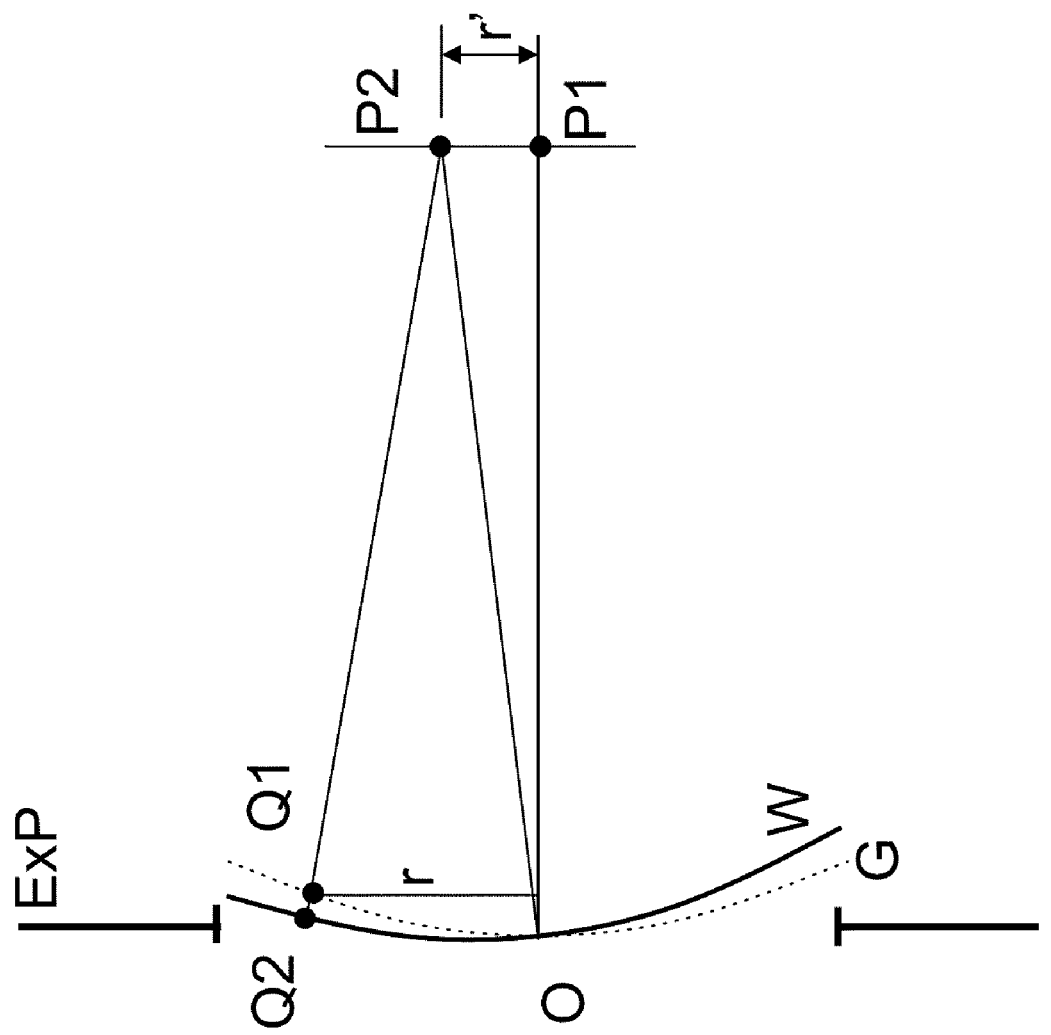
FIG. 2 illustrates a Gaussian wavefront G and an aberrated wavefront W.

FIG. 2 illustrates that the wavefront of the laser beam can deviate from an ideal behavior in several different ways and for several different reasons. A large group of these deviations are called aberrations. Aberrations (and the other wavefront distortions) displace real image points from the ideal paraxial Gaussian image points. FIG. 2 illustrates wavefronts of light exiting through an exit pupil ExP. The undistorted spherical wavefront G emanates from the pupil and converges to a point P1 at the center of curvature of the wavefront G. G is also called the Gaussian reference sphere. An aberrated wavefront W deviates from G and converges to a different point P2. The aberration $\Delta W$ of the aberrated wavefront W at point Q1 can be characterized by the optical length of the pathway relative to the undistorted reference sphere G: $\Delta W = n_i \overline{Q1Q2}$, where $n_i$ is the refractive index of the medium in the image space and $\overline{Q1Q2}$ is the distance of points Q1 and Q2.

In general, the aberration $\Delta W$ depends on the coordinates both at the exit pupil as well as at the focal plane. Therefore, this aberration $\Delta W$ can be also thought of as a correlation function: it represents that the set of points whose image converges to P2, removed from P1 on the optical axis by r', are located on a surface W, which deviates from the reference sphere G by an amount of $\Delta W$ at the radial distance r at the Exit pupil ExP. For a rotationally symmetrical system, $\Delta W$ can be written in terms of a double power series expansion in r and r' as:

$$\Delta W(r'; r, \Theta) = \sum_{l=0}^{\infty} \sum_{n=1}^{\infty} \sum_{m=0}^{\infty} {}_{2l+m}a_{nm} r'^{2l+m} r^n \cos^m \Theta. \quad (1)$$

Here r' is the radial coordinate of the image point P2 in the focal plane and r is the radial coordinate of point Q1 at the pupil. The angular dependence is represented by $\Theta$, the spherical angle. $n = 2p + m$ is a positive integer and ${}_{2l+m}a_{nm}$ are the expansion coefficients of the aberrated wavefront W. For reference, see e.g.: *Optical Imaging and Aberrations, Part I. Ray Geometrical Optics by Virendra N. Mahajan, SPIE Optical Engineering Press*. The order i of an aberration term is given by $i = 2l + m + n$.

The terms up to $i = 4$ are related to the primary aberrations: spherical, coma, astigmatism, field curvature and distortion. The actual relations between these primary aberrations and the ${}_{2l+m}a_{nm}$ aberration coefficients are documented in the literature. For a system imaging a point object, the explicit dependence of the aberration terms on the image radius r' can be suppressed by introducing the dimensionless variable $\rho = r/a$, where a is a transverse linear extent of the exit pupil, such as its radius:

$$\Delta W(\rho, \Theta) = \sum_{n=1}^{\infty} \sum_{m=0}^{\infty} a_{nm} \rho^n \cos^m \Theta, \qquad (2)$$

where $$a_{nm} = d^n \sum_{l=0}^{\infty} 2l+m a_{nm} r'^{2l+m}. \qquad (3)$$

A benefit of this notation is that the aberration coefficients $a_{nm}$ all have the dimension of length and represent the maximum value of the corresponding aberration at the exit pupil. In this notation, for example, the spherical aberration is characterized by the aberration coefficient $a_{40}$.

While the description of aberration in terms of the aberration coefficients $a_{nm}$, is mathematically well defined, it is not always the experimentally most accessible approach. Therefore, three alternative aberration measures are described next.

In the same vein of experimental accessibility and testability, it is noted that the behavior of a beam in a biological tissue, such as the eye, may not be the easiest to measure. Helpfully, studies indicate that rays in the eye may behave very analogously to rays in salty water with physiologically appropriate salt concentration, where they can be quantitatively measured and described. Therefore, throughout the application when the laser delivery system's behavior in the eye is described, it is understood that this description refers to behavior either in the described eye tissue, or in corresponding salty water.

Figure 3C:
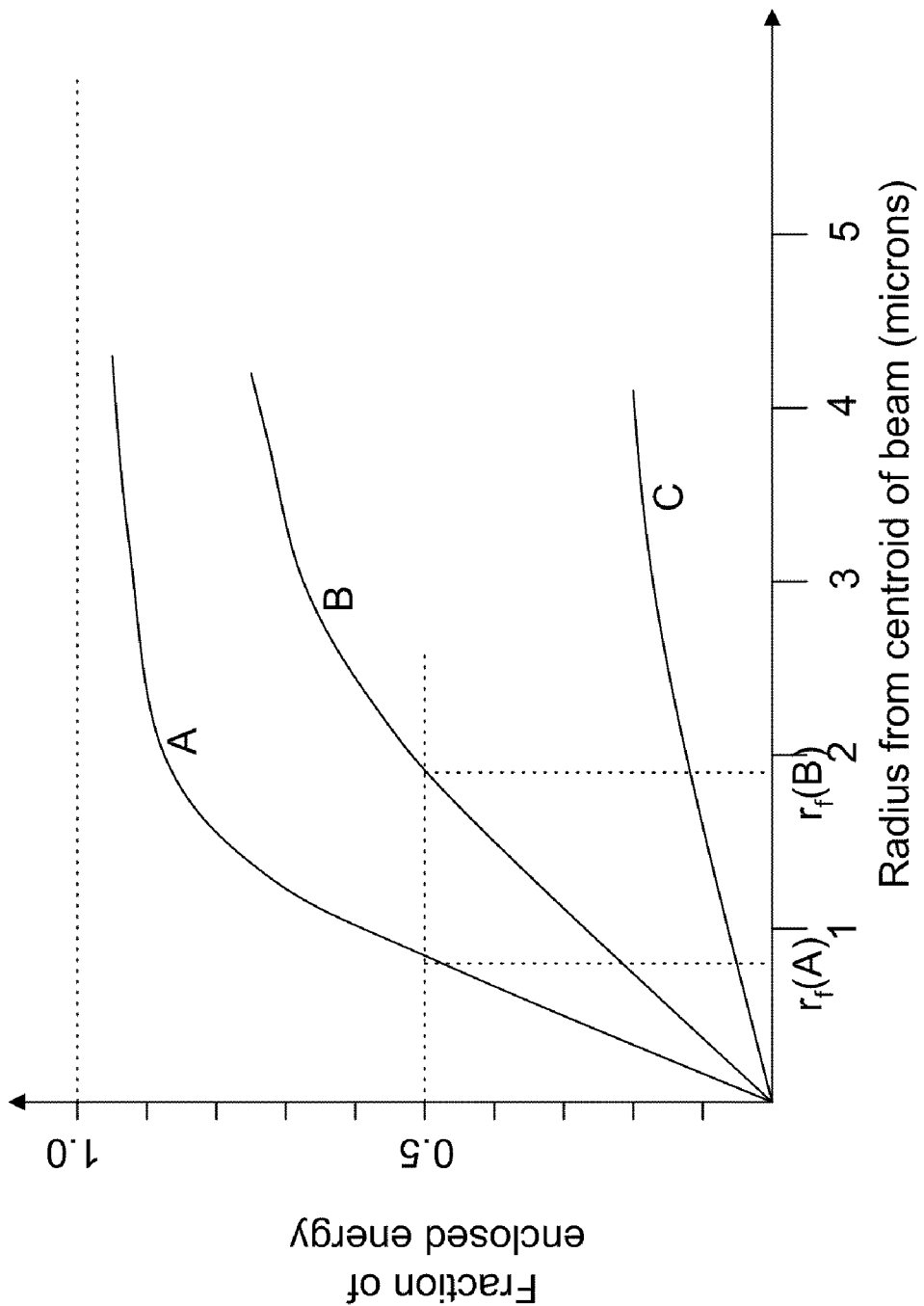
FIG. 3C illustrates a definition of the focal spot radius.

FIGS. 3A-C illustrate a second measure of aberrations. The laser delivery system 1, which was configured to focus a beam at a focal plane 210 at depth A, can cause a spherical aberration if it is operated to focus the beam at an operating focal plane 211 at depth B instead. Such a situation can occur, for example, during a three dimensional scanning procedure, when the focal point of the laser beam is moved from focal plane 210 to focal plane 211.

FIG. 3A illustrates the case when the laser delivery system 1 focuses the rays to their optimal focal plane 210. The rays pass through a spot at the optimal focal plane 210 (a "focal spot") of very narrow radial extent, or radius, $r_f(A)$. This radial extent $r_f(A)$ can be greater than zero for a variety of reasons, such as the diffraction of the light beam. The radius of the focal spot can be defined in more than one ways. A common definition of $r_f(A)$ is the minimal radius of the light spot on a screen as the screen's position is varied along the axial, or Z, direction. This Z depth is often called the "point of least confusion". This definition is further refined in relation to FIG. 3C.

FIG. 3B illustrates the case when the laser delivery system 1 scans the focus by some distance, such as a few millimeters, off the optimal focal plane 210, to an operating focal plane 211. Visibly, the rays pass through a focal spot of a radius $r_f(B)$ larger than $r_f(A)$, causing a spherical aberration. Mathematical formulae of various accuracy have been developed connecting the aberration coefficients $a_{nm}$ and the focal spot radius $r_f$. In some cases, the focal spot radius $r_f$ is an experimentally more accessible measure to quantify the aberrations than the $a_{mn}$ aberration coefficients.

FIG. 3C illustrates a more quantitative definition of the focal spot radius $r_f$. FIG. 3C illustrates the energy contained in a spot of radius r, measured from a centroid of the beam. A widely accepted definition of the focal spot radius $r_f$ is the radius, within which 50% of the beam's energy is contained. The curve labeled "A" shows that in a diffraction limited beam, when the beam is focused to its optimal focal plane 210, as in FIG. 3A, 50% percent of the beam's energy can be contained, or enclosed, in a spot of radius r=0.8 micron, providing a useful definition of $r_f(A)$.

Surgical procedures based on laser induced optical breakdown (LIOB) can have higher precision and efficiency and smaller undesirable effects if the laser beam's energy is deposited in a well or sharply defined focal spot. LIOB is a highly nonlinear process with an intensity (plasma-) threshold: typically, tissue exposed to a beam with intensity higher than the plasma threshold turns into plasma, whereas tissue exposed to a beam with intensity below the plasma threshold does not undergo the plasma transition. Therefore, a broadening of the focal spot by aberration reduces the fraction of the beam which achieves intensity at the focal plane higher than the plasma threshold and increases the fraction of the beam whose intensity remains below the threshold. This latter fraction of the beam is not absorbed effectively by the target tissue and continues to propagate through the eye tissue, in most cases to the retina, potentially causing undesirable retinal exposure.

For surgical procedures aimed at correcting the cornea, the focal plane is typically scanned, or shifted, in the Z direction (along the optical axis) only by about 0.6 mm from its optimal or nominal depth, since the thickness of the cornea is essentially 0.6 mm, in rare case thicker but still does not exceed 1 mm. The curve labeled "B" illustrates that when the focal plane of a beam is shifted from its optimal focal plane 210 by 1 mm (an upper estimate for corneal procedures) to the operating focal plane 211, 50% of the beam's energy is contained within the focal spot radius of $r_f(B)=1.8$ micron. While this shift introduces an aberration, but its measure is limited. Correspondingly, some of the existing corneal laser systems do not compensate this aberration at all, while others introduce only some limited level of compensation.

Besides the aberration coefficients $a_{mn}$ and the focal spot radius $r_f$, a third measure of aberrations is the so-called Strehl ratio S. The Strehl ratio S of a system can be defined referring to a beam which emanates from a point source, as a peak intensity of the beam at the focal plane of the system divided by the theoretical maximum peak intensity of an equivalent perfect imaging system, which works at the diffraction limit. Equivalent definitions are also known in the literature and are within the scope of the definition of the Strehl ratio S.

Corresponding to this definition, the smaller the value of S, the bigger the aberration. An unaberrated beam has S=1 and conventionally, when S>0.8, the imaging system is said to be diffraction limited.

A fourth definition of the aberrations is $\omega$, a root-mean-square, or RMS, wavefront error which expresses the deviation $\Delta W$ of the aberrated wavefront W from the undistorted wavefront G of FIG. 2, averaged over the entire wavefront at the Exit pupil ExP. $\omega$ is expressed in units of the wavelength of the beam, making it a dimensionless quantity.

Figure 4:
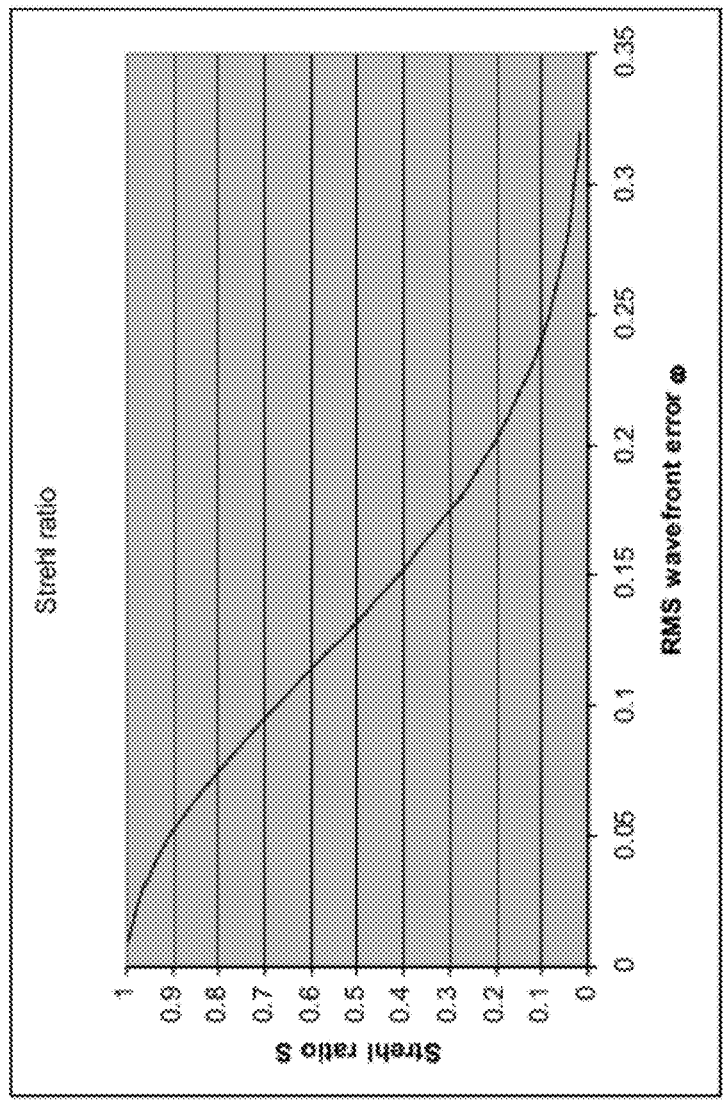
FIG. 4 illustrates a relation between a Strehl ratio S and an RMS wavefront error $\omega$.

FIG. 4 illustrates that for relatively small aberrations $\omega$ and S are related by the following empirical formula:

$$S \approx e^{-(2\pi\omega)^2} \qquad (4),$$

regardless of the type of aberration, where e is the base of natural logarithm.

All four of the above measures of aberration are useful for diagnosing problems and optimizing the design of the laser delivery system 1. Accordingly, below the general terminology "aberration measure" can refer to any one of these measures, or their equivalents. Notably, increasing aberration is captured by an increase of the aberration coefficients $a_{mn}$, focal spot radius $r_f$ and RMS wavefront error $\omega$, but by a decrease of the Strehl ratio S.

The relationship between these aberration measures is demonstrated by showing the spherical aberration coefficient $a_{40}$ and the corresponding Strehl ratio S in a specific example. In the example, the surgical laser system focuses the laser beam in an ocular tissue at different depths below its surface. The laser beam is diffraction limited, with a 1 micrometer wavelength and NA=0.3 numerical aperture, and is focused at the surface of the tissue at normal angle of incidence. The numbers of this example can be analogous to the effects of adding a plan parallel plate of thickness equal to the scanned depth near the focal plane of the system, and carrying out the calculation for salty water.

The surface of the tissue introduces aberrations in the beam, characterized by Equations (2) and (3). The spherical aberration, characterized by the aberration coefficient $a_{40}$, is zero at the surface, the Strehl ratio, by its very construction, is S=1.

LASIK surgeries typically form flaps in a depth of 0.1 mm. At these depths, the Strehl ratio S is reduced to about 0.996, only a small decrease. Even at 0.6 mm depth, approximately at the posterior surface of the cornea, S is about 0.85. While this is a non-negligible decrease of peak intensity, but still can be compensated by adjusting the laser beam intensity.

On the other hand, at 5 mm depth, characterizing the anterior surface of the crystalline lens in the eye, the Strehl ratio can decrease to S=0.054. At this depth and Strehl ratio, the beam intensity is reduced considerably below the plasma-threshold, and thus the beam is unable to generate LIOB. This drastic loss of peak intensity cannot be compensated by increasing the laser power without undesirable effects such as a serious over-exposure of the retina or excessively increased bubble size.

Table 1 illustrates the spherical aberration $a_{40}$, corresponding to the just-described Strehl ratios. Visibly, the spherical aberration increases approximately linearly with the tissue-depth, whereas the Strehl ratio S behaves in a non-linear manner:

TABLE 1

| Depth in tissue [mm] | Spherical aberration $a_{40}$ [micron] | Strehl ratio S |
|---|---|---|
| 0 | 0.00 | 1.000 |
| 0.1 | −0.04 | 0.996 |
| 0.6 | −0.24 | 0.856 |
| 5 | −2.00 | 0.054 |
| 10 | −3.99 | 0.041 |

In surgical procedures aimed at performing lens lysis, capsulotomy, or other surgical procedures on the crystalline lens, the focal plane is often scanned across the entire depth of the lens, which can be as much as 5 mm. Moreover, in integrated cornea-lens systems, the total scanning depth can extend from the cornea to the posterior surface of the lens, about 10 mm. The curve labeled "C" in FIG. 3C indicates that in such cases the focal spot radius grow up to $r_f(C)=18$ microns, which value is too large to even appear on the same plot as $r_f(A)$ and $r_f(B)$. In some embodiments, the optimal focal plane can be chosen to lie halfway in the depth-scanning range and the laser beam maybe scanned in a plus/minus 5 mm depth range. In this case $r_f(C)$ can be reduced to 10 microns.

These large $r_f(C)$ values translate to a great amount of aberration in the other three aberration measures $a_{40}$, S and $\omega$. Clearly, in contrast to the corneal procedures which scan only a few tenth of a millimeter, these large aberrations of lens surgery pose numerous challenges for the design of the laser delivery system 1 to compensate or manage their undesirable consequences.

To address the problem of large aberration measures, associated with lens surgery, some embodiments include the Precompensator 200 to precompensate the spherical aberration and improve the aberration measures. These aberrations can be developed in the target tissue, or along a portion of the optical pathway within the laser delivery system 1, or along the entire optical pathway.

Figure 5:
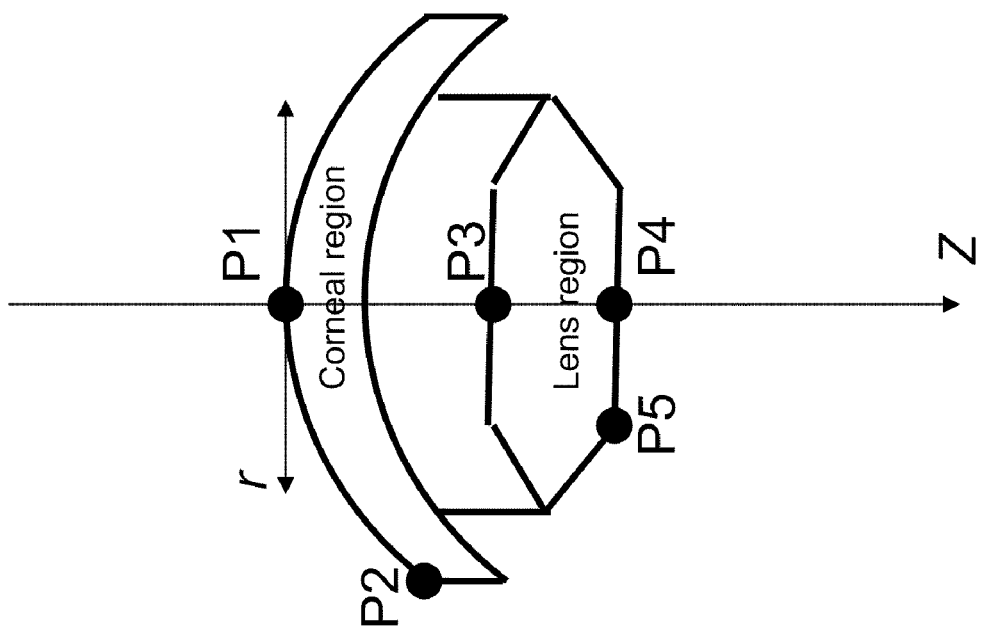
FIG. 5 illustrates reference points for ophthalmic surgery.

FIG. 5 illustrates (not to scale) that, since the aberration measures $r_f(C)$, $a_{40}$, S and $\omega$ depend on the focal spot's depth z and its radial distance r from the optical axis, in what follows when it is described that an aberration measure assumes a value, this will refer to the aberration measure assuming the described value at some selected reference points. A set of relevant reference points can be described by their cylindrical coordinates (z, r): P1=(0,0), P2=(2,6), P3=(5,0), P4=(8,0), P5=(8,3), all in millimeters. Since the main structures of the eye exhibit an approximate cylindrical symmetry, these P reference points can be located at any azimuth angle $\phi$. Therefore, these P points will be referred to only by two of their three cylindrical coordinates, the azimuth angle $\phi$ being suppressed. P1 is a typical point for a centrally located corneal procedure, P2 is typical for peripheral corneal procedures, P3 is related to the anterior region of the lens, P4 is related to the posterior of the lens, and P5 is a peripheral lens reference point. Other reference points can be adopted to characterize the aberrations of a laser delivery system as well. In some cases, an aberration measure can refer to the aberration measure averaged over the operational wavefront, or illuminated area.

The aberration measures can be determined in several different ways. A wavefront of the laser beam can be tracked in a computer-aided design (CAD) process through a selected section of the optical pathway, such as a model of the target tissue, or a section of the laser delivery system 1. Or, the aberration of the laser beam can be measured in an actual laser delivery system, or a combination of these two procedures.

Accordingly, in some implementations the precompensation, introduced by the Precompensator 200 may be selected by determining, calculating or measuring an aberration measure along a selected portion of the optical pathway, which may include the target tissue itself and then determining an amount of precompensation which is needed to compensate a preselected portion of the determined/calculated/measured aberration.

The Precompensator 200 can correct, or precompensate, the spherical aberration efficiently, because the spherical aberrations dominantly affect axial rays. Other types of aberrations, such as transverse aberrations, astigmatism and coma, affect non-zero angle rays as well as field rays, including rays being offset from the optical axis. While the laser beam, generated by the laser engine 100 is an essentially axial beam, the various blocks in the optical pathway, most notably the XY Scanner 300, transform this axial beam into a non-zero angle beam, having field rays.

Therefore, in designs where a precompensator is placed after the XY Scanner 300, the field rays of the beam can develop several different aberrations. This emergence of different aberrations poses great design challenges because (i) the optimization of the beam may require compensating several of the aberrations, and (ii) the different types of aberrations are not independent from each other. Thus, compensating one type of aberration typically induces unwanted other types of aberration.

Therefore, in architectures where a compensator is placed after the XY scanner, the spherical aberrations are typically compensated only to a limited degree and at the expense of introducing other types of unwanted aberrations.

In contrast, embodiments of the present laser delivery system 1 can have the Precompensator 200 before the XY Scanner 300. This design allows the Precompensator 200 to precompensate a spherical aberration without introducing other types of unwanted aberrations.

Some implementations can even exploit the above mentioned interdependence of the on-axis and the off-axis aberrations by introducing an on-axis precompensation by the Precompensator 200 to precompensate an off-axis aberration, caused by a subsequent segment of the laser delivery system or the target tissue.

FIGS. 6A-B illustrate schematically an idealized operation of the Precompensator 200.

FIG. 6A illustrates a laser delivery system 1 without a precompensator. In general, an optical pathway segment 301 can introduce some level of spherical aberration. This is shown by an undistorted wavefront entering the optical pathway segment 301 and a wavefront with aberration leaving the optical pathway segment 301. This segment can be any segment of the optical pathway, such as a portion of the target tissue, or the entire target tissue, or a portion of the pathway within the laser delivery system 1.

FIG. 6B illustrates that the Precompensator 200 can introduce a compensating (or complementary) distortion of the wavefront. This precompensated wavefront then enters the optical pathway segment 301, causing it to output a wavefront with reduced distortion, or even without distortion.

Some existing systems do not have a dedicated compensator at all. Other systems may compensate the spherical aberration only in a distributed manner by the lenses of lens groups which have other functions as well and are positioned after the XY scanner. In these existing systems, the parameters of the lenses are chosen as a result of making compromises between different functionalities, leading to limitations on their performance.

In contrast, embodiments of the laser delivery system 1 can have the dedicated Precompensator 200 disposed before the XY Scanner 300. In some embodiments, the Precompensator 200 is the first optical unit, or lens group, which receives the laser beam from the laser engine 100. Since because of its location the laser beam reaches the Precompensator 200 without developing non-zero angle rays or field rays (which could be caused by the XY Scanner 300), these embodiments can achieve a high level of precompensation. The precompensation is also efficient because it is a primary function of the Precompensator 200 and thus design compromises can be kept very limited, as opposed to existing systems, which compensate with lenses serving additional functions.

For these reasons, in such implementations it is possible to correct the spherical aberration to a high degree without affecting or introducing other types of aberrations.

It is known in the theory of aberrations, that the spherical aberration of a compound lens system is approximately the sum of spherical aberrations of individual components. Therefore, in some implementations of the laser delivery system 1, an unwanted amount of spherical aberration can be precompensated by designing the Precompensator 200 to introduce an equal amount of aberration, but with the opposite sign.

As an example, when the depth of the focal spot inside the eye tissue is moved by 5 mm off its optimal focal plane, the spherical aberration $a_{40}$ (according to Table 1) is $-2.0$ micrometers. Accordingly, in some implementations the Precompensator 200 can introduce an aberration measure of $a_{40} = +2.0$ micrometers. In a first approximation this precompensation may essentially eliminate the spherical aberration caused by the 5 mm shift of the focal spot and correspondingly increase the Strehl ratio from $S=0.054$ back to $S=1$. (This simple example disregarded other sources of aberrations.)

Some implementations below will be characterized by comparing the aberration measures of "non-precompensated" laser delivery systems 1, i.e. laser delivery systems where the Precompensator 200 has been removed, to "precompensated" laser delivery systems, i.e. systems where the Precompensator 200 has not been removed.

In some implementations, installing the Precompensator 200 can increase the Strehl ratio from a value $S<S(precomp)$ of the non-precompensated laser delivery system 1 to a value $S>S(precomp)$ for the precompensated laser delivery system 1. In some implementations S(precomp) can be 0.6, 0.7, 0.8 or 0.9, for example.

As stated above, this Strehl ratio S here and below can refer to any one of the Strehl ratios $S(P1), \ldots S(P5)$ at the five reference points P1-P5 above, or to the Strehl ratio at some other predetermined reference points, or to an average of the Strehl ratios over the five reference points, or to an average over the operational wavefront.

Also, the Strehl ratio can refer to the entire laser delivery system 1, receiving the laser beam from Laser Engine 100, ending with the Objective 700 and forming the focal spot in an ophthalmic target tissue. In some other cases the term can refer to other targets, including air. In some implementations the term can refer to a subsystem of the laser delivery system 1.

In some implementations, the addition of the Precompensator 200 to the non-precompensated laser delivery system 1 can increase a Strehl ratio from a non-precompensated value below $S=S(precomp)$ to a precompensated value above $S=S(precomp)$ for pulses having an associated bandwidth at least an order of magnitude larger than the transform-limited bandwidth of laser pulses with a duration of a picosecond or longer. As above, S(precomp) can be 0.6, 0.7, 0.8, or 0.9, for example.

In some implementations the addition of the Precompensator 200 to the laser delivery system 1 can increase a Strehl ratio from a non-precompensated value below $S=S(precomp)$ to a precompensated value above $S=S(precomp)$ over a range of wavelengths of 0.4 microns to 1.1 microns. As above, S(precomp) can be 0.6, 0.7, 0.8, or 0.9, for example.

In some implementations the addition of the Precompensator 200 can increase a system numerical aperture from a non-precompensated value below $NA=NA(precomp)$, corresponding to the laser delivery system 1 without the Precompensator 200, to a precompensated value above $NA=NA(precomp)$ with the Precompensator 200. In some implementations, the value of NA(precomp) can be 0.2, 0.25, 0.3 or 0.35, for example.

In some implementations adding the Precompensator 200 to a laser delivery system 1 without one can decrease the focal spot radius $r_f$ in a target tissue from a non-precompensated value above $r_f(precomp)$ to a precompensated value below $r_f(precomp)$, corresponding to the laser delivery system 1 with the Precompensator 200. In some implementations $r_f(precomp)$ can be 2, 3 or 4 microns.

In some implementations, installing the Precompensator 200 can increase the RMS wavefront error from a value $\omega > \omega(precomp)$ of the non-precompensated laser delivery system 1 to a value $\omega < \omega(precomp)$ for the precompensated laser delivery system 1. In some implementations $\omega$(precomp) can be 0.06, 0.07, 0.08 or 0.09, all in units of the wavelength of the laser beam, for example.

In some implementations, installing the Precompensator 200 can increase the spherical aberration coefficient from a value $a_{40} > a_{40}$(precomp) of the non-precompensated laser delivery system 1 to a value $a_{40} < a_{40}$(precomp) for the precompensated laser delivery system 1. In some implementations $a_{40}$(precomp) can be 2, 3, or 4 micrometers, for example.

In some implementations, installing the Precompensator 200 into a non-precompensated laser delivery system 1 can reduce at least one of the following aberration measures: the RMS wavefront error $\omega$, the spherical aberration measure $a_{40}$ and the focal spot radius $r_f$ from a non-precompensated value by at least a precompensation percentage P(precomp), or increase a Strehl ratio S by at least the precompensation percentage P(precomp). In some implementations P(precomp) can be 10%, or 20%, or 30%, or 40%, for example.

As described above, any one of these aberration measures can belong to any one of the reference points P1, ... P5, or to some other predetermined reference points, or to an average of values at reference points, or can be an average over the wavefront.

In some embodiments, the Precompensator 200 can compensate non-spherical aberrations, such as first, or higher order aberrations as well. In some cases it can perform precompensation of off-axis rays too.

In some implementations, the Precompensator 200 precompensates other types of aberrations, while not increasing the RMS wavefront error by more than 0.075, or by keeping the Strehl ratio above S(precomp), having a value of e.g. 0.8.

In some implementations the Precompensator 200 can increase the radius of the beam rb exiting the Precompensator 200 to a value above rb=rb(precomp), where rb(precomp) can be e.g. 5 mm or 8 mm.

Some of these functionalities can be reached by including one or more movable lenses into the Precompensator 200. Position actuators can move the movable lens or lenses, changing the distance between some of the lenses of the Precompensator 200.

In implementations with one movable lens, the movable lens of the Precompensator 200 can move the focal plane or spot of the laser delivery system 1 along the optical axis by 0.3-4.0 mm. In some other implementations, by 0.5-2.0 mm.

In some implementations, when at least one of the Strehl ratios S(low) at the above described five reference points P1, ... P5 is below S=S(movable) when the movable lens is in a median position, the movable lens can be moved to increase the Strehl ratio S(low) to a value above S=S(movable). S(movable) can be 0.6, 0.7, 0.8 or 0.9.

In some implementations the movable lens can be moved to vary the Strehl ratio S in the range 0.6-0.9. In other implementation in the range 0.70-0.85.

Since the Precompensator 200 is located before the XY Scanner 300 or other beam expanders, the beam radius is still small. Therefore, the movable lens can be small. And since the movable lens is small, the position actuators can move it very fast, allowing for a very quick changing of the focal depth. This feature speeds up the depth scanning, or Z scanning in these embodiments and can make the Z scanning speed comparable to the typically faster XY scanning speed.

In some typical existing systems, the aberrations are compensated dominantly by optical means, such as lenses. The presently described movable lens Precompensator 200 can utilize the fast movable lens or lenses to carry out this function well. In particular, when the laser beam is scanned with the XY Scanner 300, the movable lens or lenses can be moved with a sufficiently high speed so that the aberrations associated with the XY scanning get compensated to a desired level.

Figure 7B:
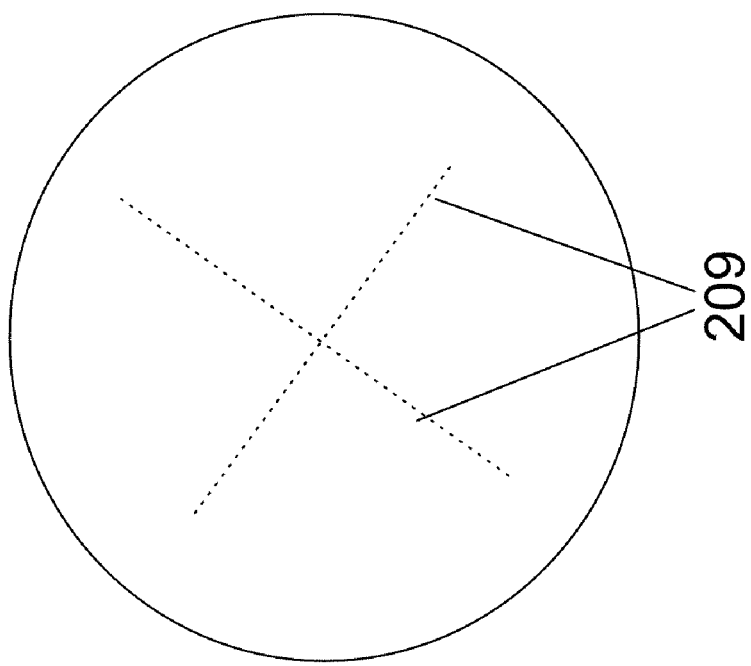
FIGS. 7A-B illustrate various uses of an efficient Z scanning functionality.
Figure 7A:
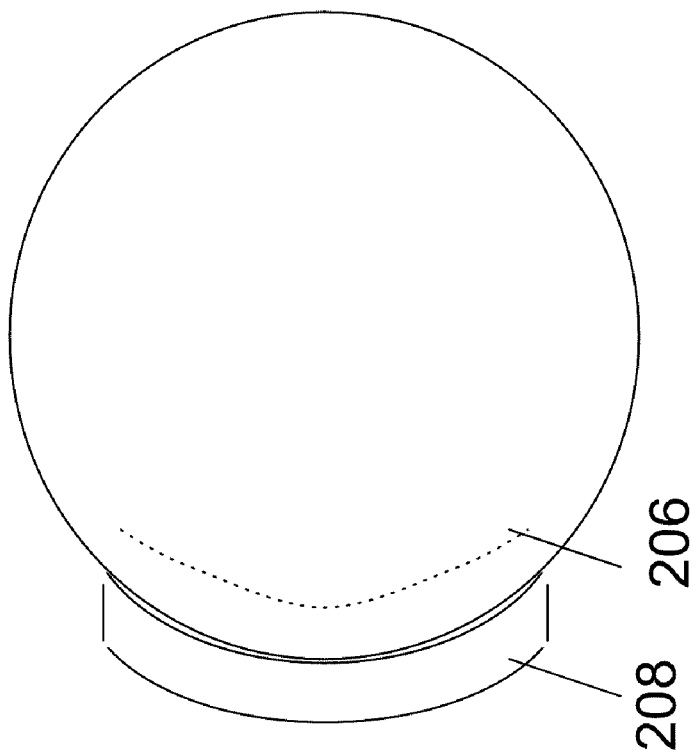

FIG. 7A illustrates that this aspect can be useful when a transverse surgical cut 206 is performed essentially tracking the contact surface of a planar or curved patient interface 208. The speed of the small movable lens makes it possible that the Z scanning is performed at the speed required by the XY scanning, forming the desired curved cut.

In some implementations a curvature, or radius, of the curved cut, or curved target line can be smaller than 1 mm, 10 mm, and 100 mm.

FIG. 7B illustrates another useful aspect of a high Z scanning speed. The focal plane of most optical systems is somewhat curved. If it is desired to create an essentially straight transversal cut, which therefore does not track the curvature of the focal plane, the focal depth needs to be continuously re-adjusted, synchronously with the fast transverse XY scanning to compensate for the curvature of the focal plane. For example, for radial cuts or planar cuts with a raster scan pattern the change of the radial, or XY coordinate, can be very fast. In these procedures a fast Z scanning speed can help forming the desired straight cut.

Finally, the high Z scanning speed can be also useful to perform some surgical procedures fast, such as corneal procedures.

In some implementations, the movable lens Precompensator 200 can change the depth of the focal spot of the laser delivery system with an axial speed at least 5% of the maximum transversal scanning speed of the focal spot. In some implementations with an axial speed at least 10% of the maximum transversal scanning speed of the focal spot. In other embodiments with an axial speed at least 20% of the maximum transversal scanning speed of the focal spot.

In some implementations, the movable lens Precompensator 200 can change the Z coordinate of the focal spot by 0.5-1 millimeter in a Z scanning time.

In some implementations this Z scanning time can be in the range of 10-100 nanoseconds, 100 nanoseconds-1 millisecond, 1 millisecond-10 milliseconds and 10 milliseconds-100 milliseconds.

In some implementations the movable lens of the lens group is movable in a Z moving range to reduce a first aberration measure by at least a movable percentage P(movable). Here the first aberration measure can be a spherical aberration coefficient $a_{40}$, an RMS wavefront error $\omega$, and a focal spot radius $r_f$; and the movable percentage P(movable) can be 10%, 20%, 30% and 40%.

In some implementations the movable lens of the lens group is movable in a Z moving range to increase a Strehl ratio S by at least a movable percentage P(movable), which can be 10%, 20%, 30% and 40%.

In some implementations, the movable lens Precompensator 200 is capable of changing a numerical aperture NA of the laser delivery system 1, a Z depth of the focal spot, any one of the aberration measures and a beam diameter essentially independently by moving the movable lens. In other words, moving the movable lens is capable of varying any one of these four characteristics of the laser delivery system 1 without changing the other two characteristics. These embodiments offer considerable control for the operator of the embodiment.

Some of the functions of the Precompensator 200 are sometimes referred to as beam conditioning or beam expanding. Correspondingly, in some existing systems blocks with analogous functions are referred to as beam conditioner or beam expanders.

In some embodiments the Precompensator 200 includes just one lens to achieve the above functionalities.

In some embodiments the Precompensator 200 includes two to five lenses to achieve the above functionalities.

Figure 8A:
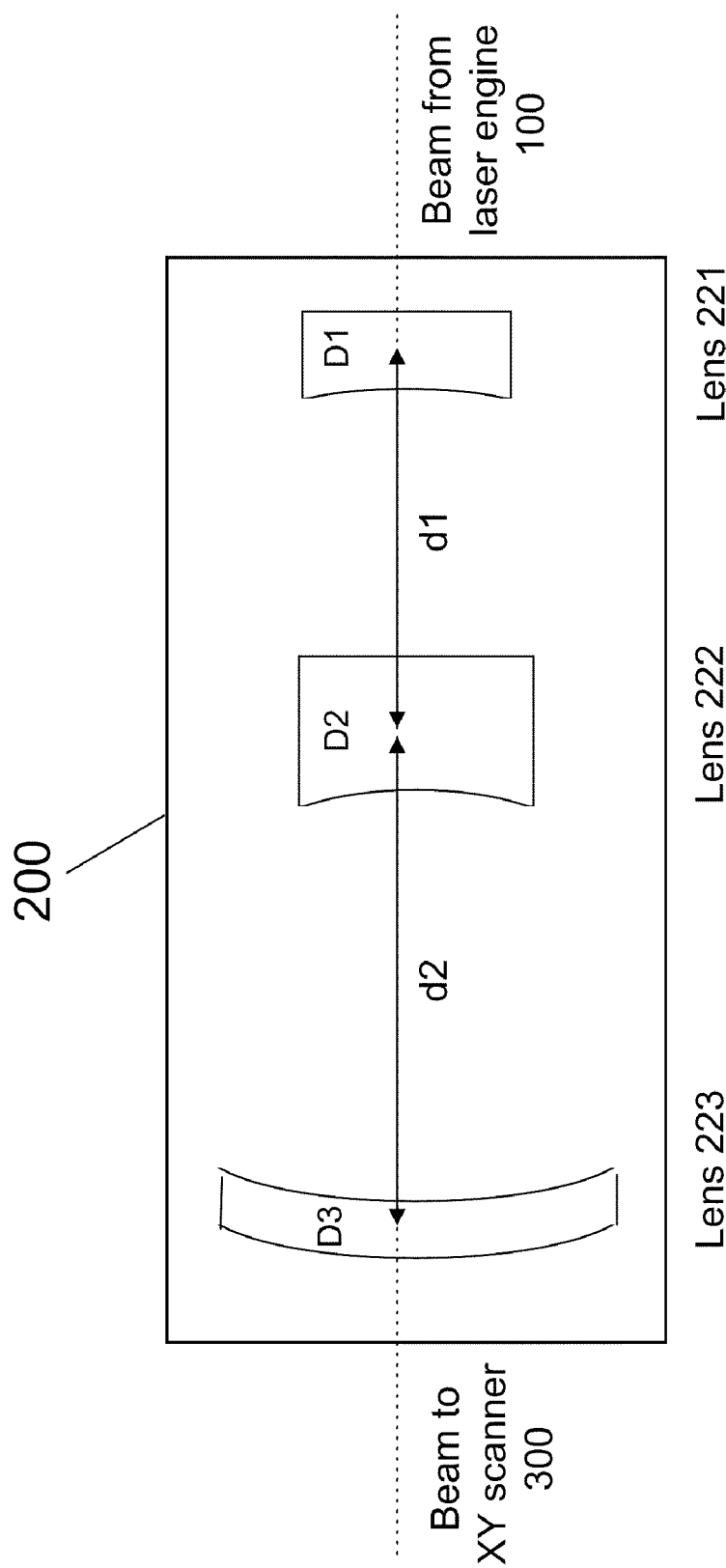
FIGS. 8A-D illustrate implementations of the precompensator 200.

FIG. 8A illustrates a three lens embodiment of Precompensator 200, including lens 221, lens 222 and lens 223.

Figure 8B:
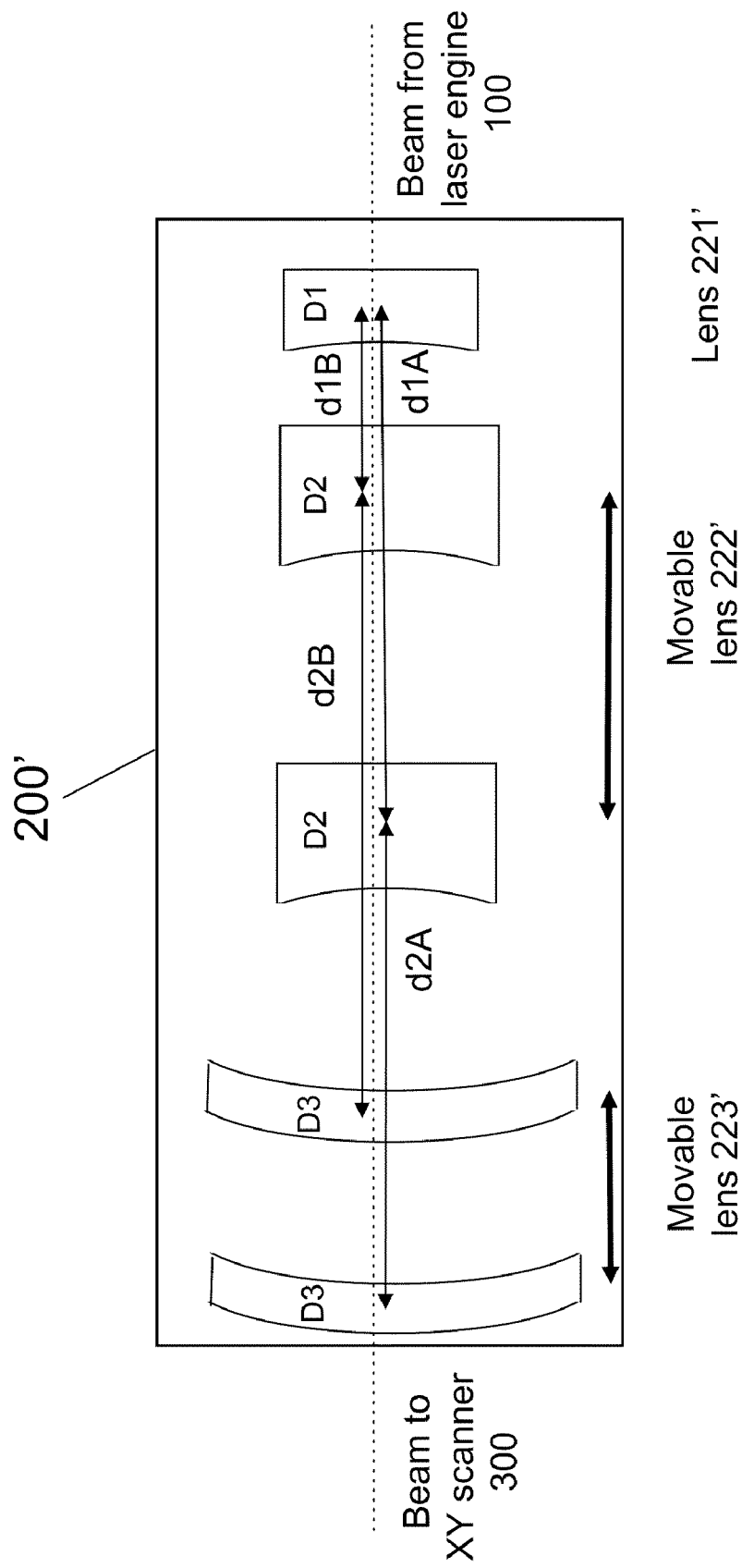

FIG. 8B illustrates a three lens embodiment of movable lens Precompensator 200', including lens 221', movable lens 222' and lens 223'.

Figure 8C:
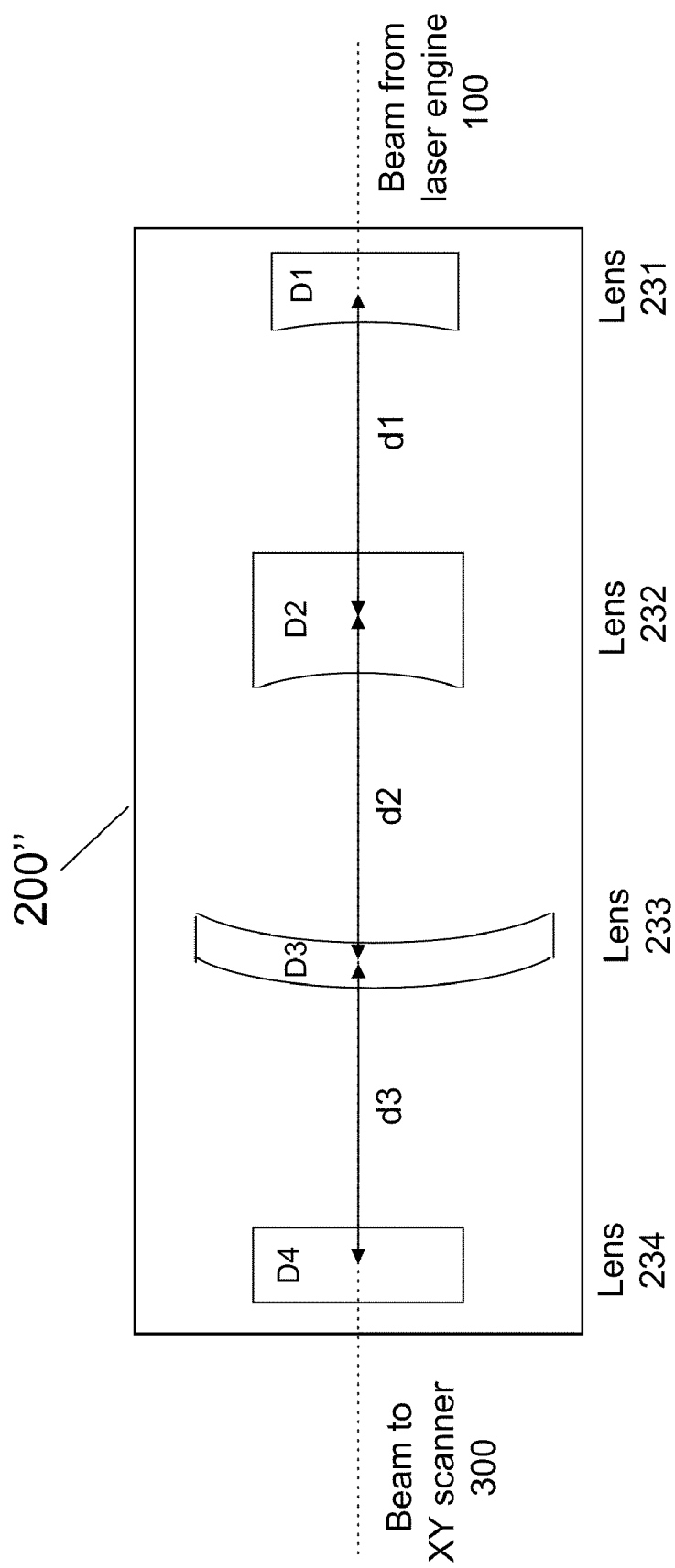

FIG. 8C illustrates a four lens embodiment of Precompensator 200", including lenses 231-234.

Figure 8D:
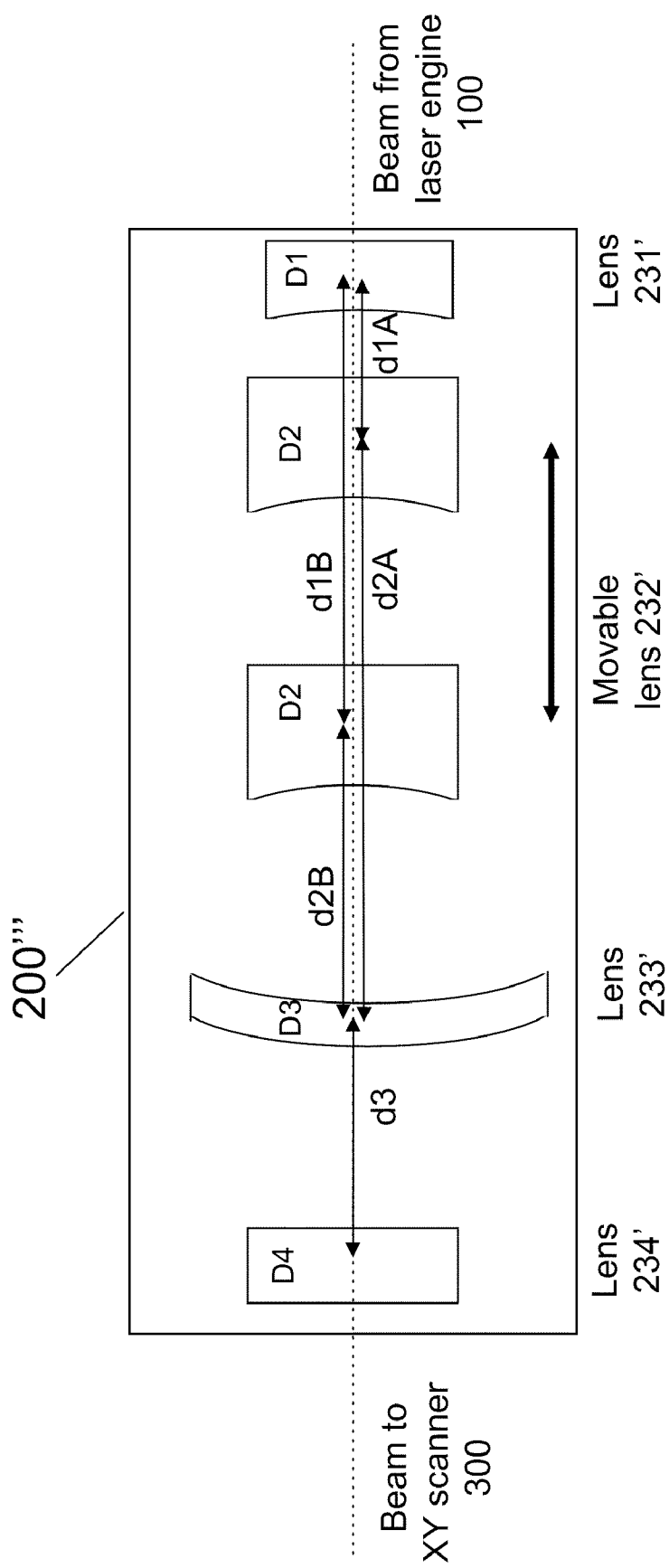

FIG. 8D illustrates a four lens embodiment of movable lens Precompensator 200''', including lens 231', movable lens 232', lens 233' and lens 234'.

Tables 2-4 illustrate various three lens implementations of the Precompensators 200 and 200' of FIGS. 8A-B. Embodiments of the Precompensator 200 can be implemented using thin lenses. Therefore, they can be described in terms of refractive powers of the individual lenses and their distances from the next lens.

Table 2 illustrates a three fixed lens embodiment of Precompensator 200, also shown in FIG. 8A. In Table 2 column 1 shows the lens number, column 2 the refractive power measured in diopters Di (i=1, 2, 3), and column 3 the distance di (i=1, 2) between lenses i and i+1.

TABLE 2 for FIG. 8A

| Lens number | Refractive power [1/m] | Distance to next lens [mm] |
|---|---|---|
| 221 | D1 = (−3, −5) | d1 = (60, 100) |
| 222 | D2 = (3, 5) | d2 = (3, 9) |
| 223 | D3 = (−3.5, −6) | |

Table 3 illustrates a possible implementation of Precompensator 200' with two movable lenses 222' and 223', as in FIG. 8B, showing lens spacings diA and diB in two configurations A and B in columns 3 and 4. The lens spacings di can vary continuously between diA and diB.

TABLE 3 for FIG. 8B

| Lens number | Refractive power [1/m] | Distance to next lens [mm], Configuration A | Distance to next lens [mm], Configuration B |
|---|---|---|---|
| 221' | D1 = (−3, −5) | d1 = (60, 100) | d1B = (1.0, 9.0) |
| 222' | D2 = (3, 5) | d2 = (3, 9) | d2B = (20, 40) |
| 223' | D3 = (−3.5, −6) | | |

Table 4 illustrates that in various implementations the above parameters Di and di can assume values in broad intervals, depending on a large number of design considerations, such as different beam sizes and available space. Some of the parameters of these implementations can be connected to the embodiments of Tables 2-3 by scaling: the refractive powers with a scaling factor a, and the distances with a corresponding scaling factor 1/a. Furthermore, the refractive powers can be additionally modified by tolerance factors t1 trough t3 to allow for differences in tolerances and design implementations. These relations are summarized in Table 4:

TABLE 4 for FIGS. 8A-B

| Lens number | Refractive power [1/m] | Distance to next lens [mm] |
|---|---|---|
| 221 | D1*a*t1 | d1/a |
| 222 | D2*a*t2 | d2/a |
| 223 | D3*a*t3 | |

In some implementations the scaling factor a can be in a range of 0.3 to 3, and the tolerance factors t1, t2, and t3 can be in a range of 0.8 to 1.2.

Analogously, Table 5 illustrates various four lens implementations of the Precompensator 200", wherein the lenses 231, 232, 233 and 234 are fixed, as shown in FIG. 8C.

TABLE 5 for FIG. 8C

| Lens number | Refractive power [1/m] | Distance to next lens [mm] |
|---|---|---|
| 231 | D1 = (−15, −20) | d1 = (100, 130) |
| 232 | D2 = (−5, −8) | d2 = (32, 41) |
| 233 | D3 = (−25, −35) | d3 = (33, 45) |
| 234 | D4 = (7, 10) | |

Table 6 illustrates a four lens implementation of the Precompensator 200' of FIG. 8D, with one movable lens 232'.

TABLE 6 for FIG. 8D

| Lens number | Refractive power [1/m] | Distance to next lens [mm], Configuration A | Distance to next lens [mm], Configuration B |
|---|---|---|---|
| 231 | D1 = (−15, −20) | D1A = (100, 130) | d1B = (120, 140) |
| 232 | D2 = (−5, −8) | d2A = (32, 41) | d2B = (20, 30) |
| 233 | D3 = (−25, −35) | d3A = (33, 45) | d3B = (31, 42) |
| 234 | D4 = (7, 10) | | |

As in the three lens implementations, the parameters of the four lens Precompensators 200" and 200''' can assume values in broad ranges. Parameters of some of these implementations again can be related to each other by scaling factors a, 1/a, t1, t2, t3, and t4, respectively, in analogy to Table 4. The scaling factor a can be in the range of 0.2 to 5 and the tolerance factors t1, . . . t4 can be in a range of 0.7 to 1.3.

In other embodiments, other combinations and ranges are employed. Within these ranges, many embodiments of the laser delivery system 1 are possible, as the system can be optimized for many different functionalities resulting in different choices. Design compromises and optimization constraints can lead to a large number of implementations, each with its own advantages. The large number of possibilities is illustrated by the ranges of parameters in the above Tables 2-6.

In a one movable lens implementation of the Precompensator 200' the moving lens can change one of the laser system's characteristics essentially independently. These parameters include the Z focal depth, the numerical aperture NA, any one of the aberration measures, and a diameter of the exit beam. For example, these implementations allow the operator to change e.g. the numerical aperture of the laser delivery system 1, without changing e.g. the Z focal depth.

In some implementations the Precompensator 200 has two independently moving elements. Such implementations allow the operator to independently control two characteristics of the laser beam, such as e.g. the beam diameter and the numerical aperture NA, while keeping the aberrations fixed.

Figure 9:
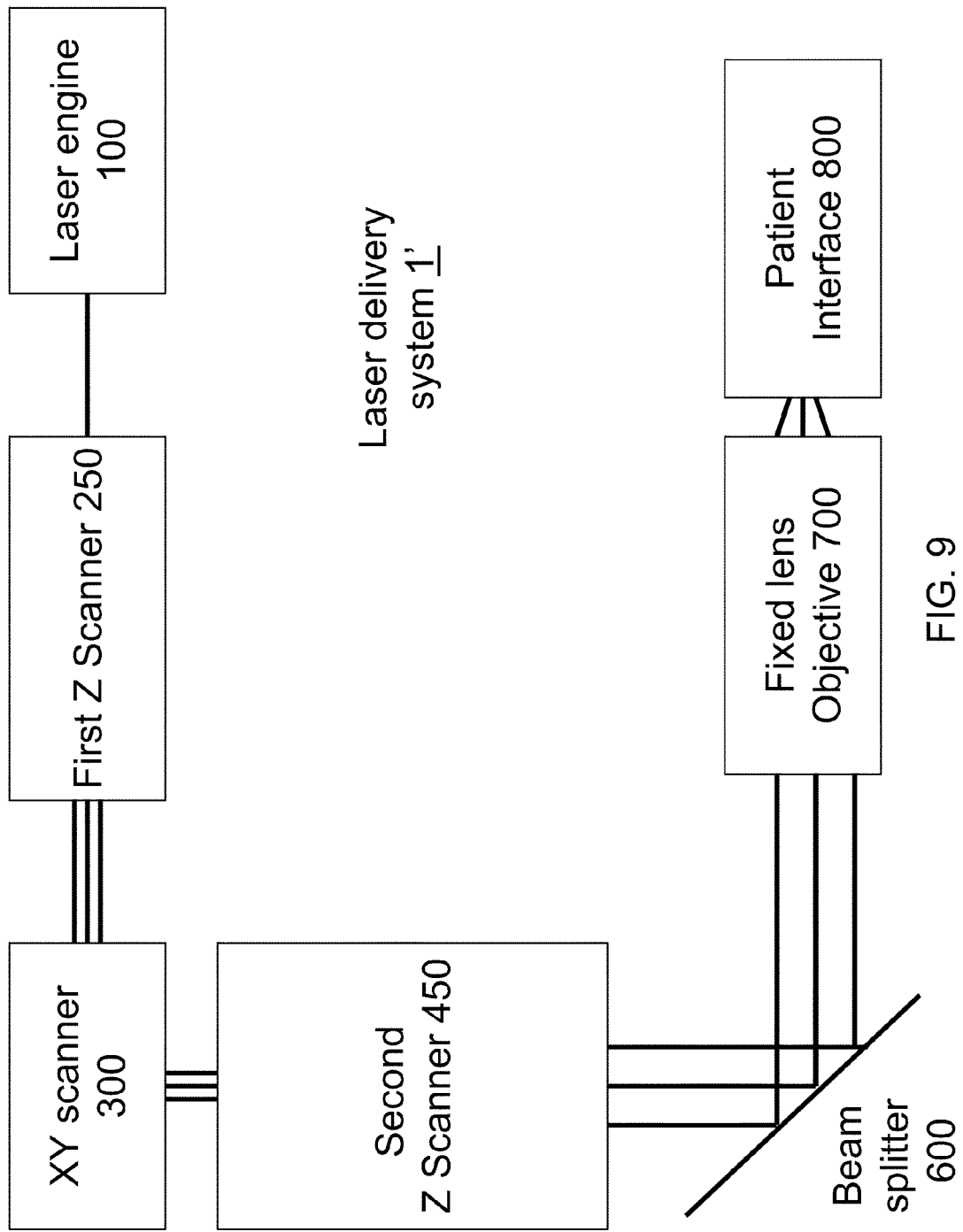
FIG. 9 illustrates an implementation of the laser delivery system 1 with two Z Scanners.

FIG. 9 illustrates an embodiment of the laser delivery system 1', where a Z scanning functionality of various optical blocks is highlighted. In particular, the laser engine 100 generates a laser beam, which is received by a first Z Scanner 250. The first Z Scanner 250 receives the laser beam from the laser engine 100 and scans a focal point of the laser delivery system 1' over a first Z interval along an optical axis of the laser delivery system 1'. The beam, outputted by the first Z Scanner 250 is received by the XY Scanner 300, which scans the laser beam in a direction essentially transverse to the optical axis of the laser system. The outputted XY scanned laser beam is then received by a second Z Scanner 450, which scans the focal point of the laser system over a second Z interval along the optical axis of the laser system.

In some embodiments, the first Z Scanner 250 is configured so that the first Z interval is suitable for a corneal surgical procedure, and the second Z Scanner 450 is configured so that the second Z interval is suitable for an anterior segment surgical procedure.

In some embodiments, the first Z interval is within the range of 0.05-1 mm and the second Z interval is within the range of 1-5 mm.

In some embodiments the first Z interval is within the range of 1-5 mm and the second Z interval is within the range of 5-10 mm.

In some embodiments the first Z Scanner 250 is configured to scan the focal point over the first Z interval of 0.05 mm-1 mm in a first Z scanning time. The first Z scanning time can be in one of the ranges of 10-100 nanoseconds, 100 nanoseconds-1 millisecond, 1 millisecond-10 milliseconds, and 10 milliseconds-100 milliseconds.

In some embodiments the second Z Scanner 450 is configured to scan the focal point over the second Z interval of 1 mm-5 mm in a second Z scanning time. The second Z scanning time can be in one of the ranges of 10-100 milliseconds, and 100 milliseconds-1 second.

In some embodiments the first Z Scanner 250 is configured to change the numerical aperture of the laser beam by more than 10%.

In some embodiments the second Z Scanner 450 is configured to change the numerical aperture of the laser beam by more than 10%.

In some embodiments the first Z Scanner 250 is configured to change the numerical aperture of the laser beam by more than 25%.

In some embodiments the second Z Scanner 450 is configured to change the numerical aperture of the laser beam by more than 25%.

FIG. 10 shows a summary table of the many variations of the above described elements. As shown, some implementations can have 0 Z depth scanners, 1 Z depth scanner before the XY Scanner 300, 1 Z depth scanner after the XY Scanner 300 and 2 Z depth scanners, one before and one after the XY Scanner 300.

Further, some implementations can have 0 NA controller, 1 NA controller before the XY Scanner 300, 1 NA controller after the XY Scanner 300 and 2 NA controllers, one before and one after the XY Scanner 300.

Here, the Z Scanners and NA controllers quite generally refer to a single lens or a lens group, which can modify the Z depth and the numerical aperture NA, respectively. In some cases these modifiers can be activated, or controlled by a single electric actuator, which makes the lenses of the modifier move synchronously to modify the NA or the Z depth of the beam.

Both the Z Scanners and the NA controllers can be housed in the first Z Scanner 250 and the second Z Scanner 450 of FIG. 9. In some cases the corresponding optical elements are distinct, in other implementations the Z Scanner and the NA controller which are housed in the same Z Scanner block 250 or 450, can share one or more lenses, movable lenses, or electric actuators.

As shown in FIG. 10, 0 Z scanners and one or two NA controllers operate at fixed Z depth, but can control NA during the XY scanning.

1 Z Scanner and 0 NA controller can perform the Z scanning.

1 Z Scanner and 1 or 2 NA controllers can perform, in addition to the Z scanning, a control of the NA.

2 Z Scanners can perform Z scanning at two speeds and also control the NA, when combined with 1 or 2 NA controllers.

Non-lens optical elements are also used in some implementations, such as variable apertures and pupils.

In addition, most of the illustrated 16 combinations can be further configured to precompensate a selected aberration, such as the spherical aberration.

FIG. 10 illustrates that the various system characteristics, such as the Z depth of the beam, its numerical aperture NA and its aberration, represented by its aberration measure such as the Strehl ratio S, can be controlled or adjusted independently of each other. Such embodiments offer a great control and precision to the operator of laser delivery system 1.

In analogous embodiments, such double beam conditioning can be performed for other pairings of beam characteristics. For example, similar tables with 4×4=16 pairings can be created regarding an aberration controller and a beam diameter controller. Here 0, 1, or 2 aberration controllers can be paired in all possible combinations with 0, 1 or 2 beam diameter controllers.

The list of beam characteristics includes: Z depth of the focal spot, the numerical aperture NA, the beam radius, and any aberration measure, such as the Strehl ratio S, the focal spot radius $r_f$, the RMS wavefront error $\omega$ and the spherical aberration measure $a_{40}$.

3. XY Scanner 300

The XY Scanner 300 may receive the precompensated beam from the Precompensator 200, either directly of indirectly, having passed through some intermediate optical elements. A function of the XY Scanner 300 may be to scan the beam received from the Precompensator 200 in a direction essentially transverse to an optical axis of the laser delivery system 1. In various embodiments, the "transverse" direction is not necessarily perpendicular to the optical axis, and can include any direction which makes a substantial angle with the optical axis.

In some embodiments the XY Scanner 300 outputs a scanning laser beam, which, having propagated through the laser delivery system 1 and having reached the surgical region, scans in a transverse direction from zero to a maximum of an XY scanning range of 5-14 mm. In some implementations maximum of the XY scanning range is between 8 and 12 mm.

Figure 11A:
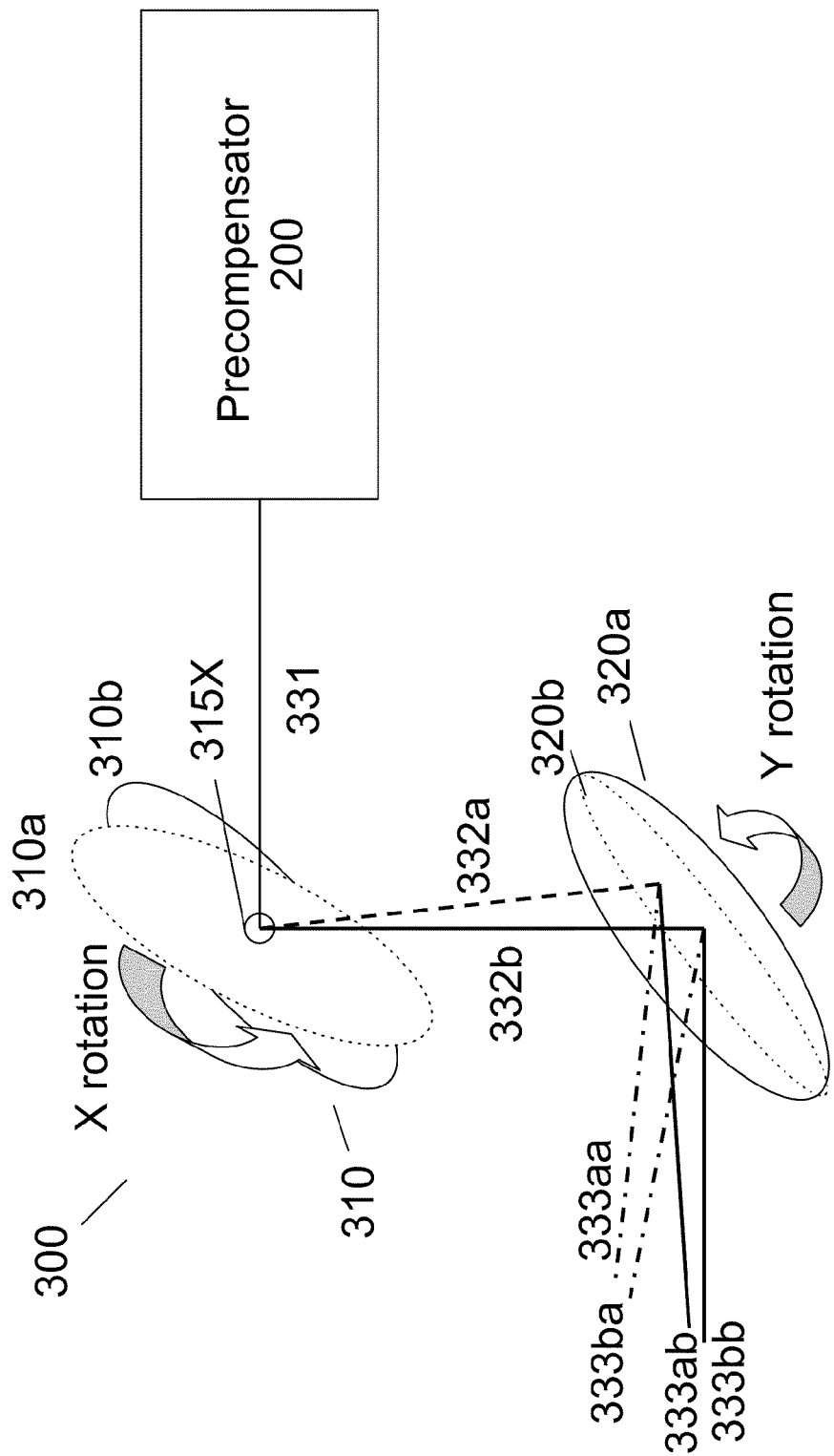
FIGS. 11A-C illustrate an XY Scanner with 2, 3, and 4 scanning mirrors.

FIG. 11A illustrates that the XY Scanner 300 can include an X scanner and a Y scanner. In some existing designs the X and the Y scanner each include one mirror: a single X scanning mirror 310 and a single Y scanning mirror 320. In such designs the beam deflected by the X scanning mirror 310 hits the Y scanning mirror 320 at different points depending on the orientation of the X scanning mirror 310. In particular, when the X scanning mirror 310 is in position 310*a*, the incident beam 331 is reflected as beam 332*a*, whereas when the X scanning mirror is rotated into position 310*b*, the incident beam is reflected as beam 332*b*.

These two beams 332*a* and 332*b* hit the Y scanning mirror 320 in different positions and therefore even for a fixed Y scanning mirror 320 in position 320*a* they will give rise to two different reflected beams 333*aa* and 333*ba*, respectively. Worse yet, when the Y scanning mirror 320 itself is rotated from position 320*a* to 320*b*, the two incident beams 332*a* and 332*b* give rise to two additional reflected beams 333*ab* and 333*bb*, all four beams 333*aa*, 333*ab*, 333*ba*, and 333*bb* propagating in different directions.

The problem can be characterized in terms of the notion of a pivot point. One definition of a pivot point of a scanning optical element can be as the point through which essentially all rays go through, having exited from the optical scanning element. This notion is the analogue of the focal point of non-moving refractive elements, as applied for moving optical elements, such as scanners.

Using this terminology, the above problem can be traced back in FIG. 11A to the X scanner pivot point 315X being fixed on the X scanning mirror 310 itself. The outputted scanned beam will appear for the subsequent optical elements as having emanated from a single pivot point 315X on the X scanning mirror 310, and thus propagating into a wide range of angles. This divergence of the two mirror designs can lead to several different types of undesirable aberrations.

Figure 11B:
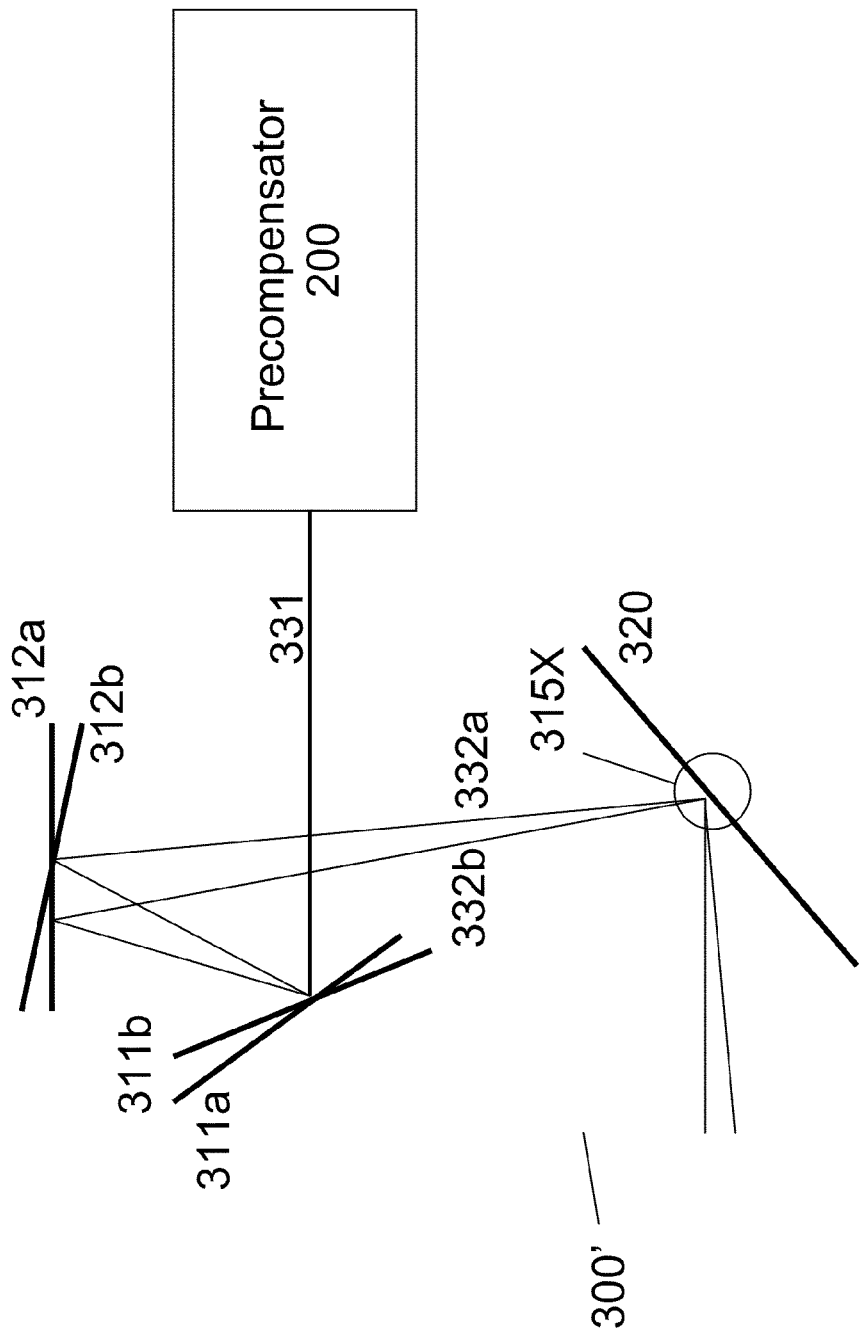

FIG. 11B illustrates an existing three mirror XY Scanner 300', where the X scanner 310 includes two mirrors 311 and 312 to address this problem. For clarity, the mirrors are shown from the side. In this design, X scanning mirrors 311 and 312 perform the X scanning function in a coordinated manner. As shown in FIG. 11B, as the first X scanning mirror 311 changes its orientation from 311*a* to 311*b*, the second X scanning mirror 312 can be rotated in a coordinated manner from 312*a* to 312*b*. These coordinated scanning rotations make it possible that the deflected beams 332*a* and 332*b* in the two rotational states go through a pivot point 315X, which is lifted off the X scanning mirrors.

Since the X scanner pivot point 315X has been lifted from the X scanning mirror itself, its location can be adjusted. In the design of FIG. 11B, the X scanning mirrors are designed to place the pivot point 315X essentially onto the Y scanning mirror 320. In such designs the problem of the X scanner 310 in FIG. 11A is essentially resolved and the corresponding aberrations are much reduced.

However, even this design has a problem analogous to that of FIG. 11A, only in the context of the Y scanning mirror 320. In the design of FIG. 11B, the Y scanner pivot point 315Y is still fixed to the Y scanning mirror.

The entrance pupil of an optical system is the image of the aperture stop when viewed from the front of the system. The exit pupil is the image of the aperture stop in the image space. In an optical system with multiple groups of lenses the locations of the entrance and exit pupils are often carefully adjusted. In many designs, the exit pupil of one lens group matches the entrance pupil of the following lens group.

For the XY scanner 310 the pivot point can be regarded as the exit pupil. In some embodiments this exit pupil matches the entrance pupil of the following lens group, such as the Z Scanner 450. However, the entrance pupil of that lens group may be inside the physical boundaries of the lens group, where a scanner block cannot be placed. In that case a scanner block is desirable for which the pivot point is outside the physical boundaries of the scanner block, at a location which can be arbitrarily chosen.

Figure 11C:
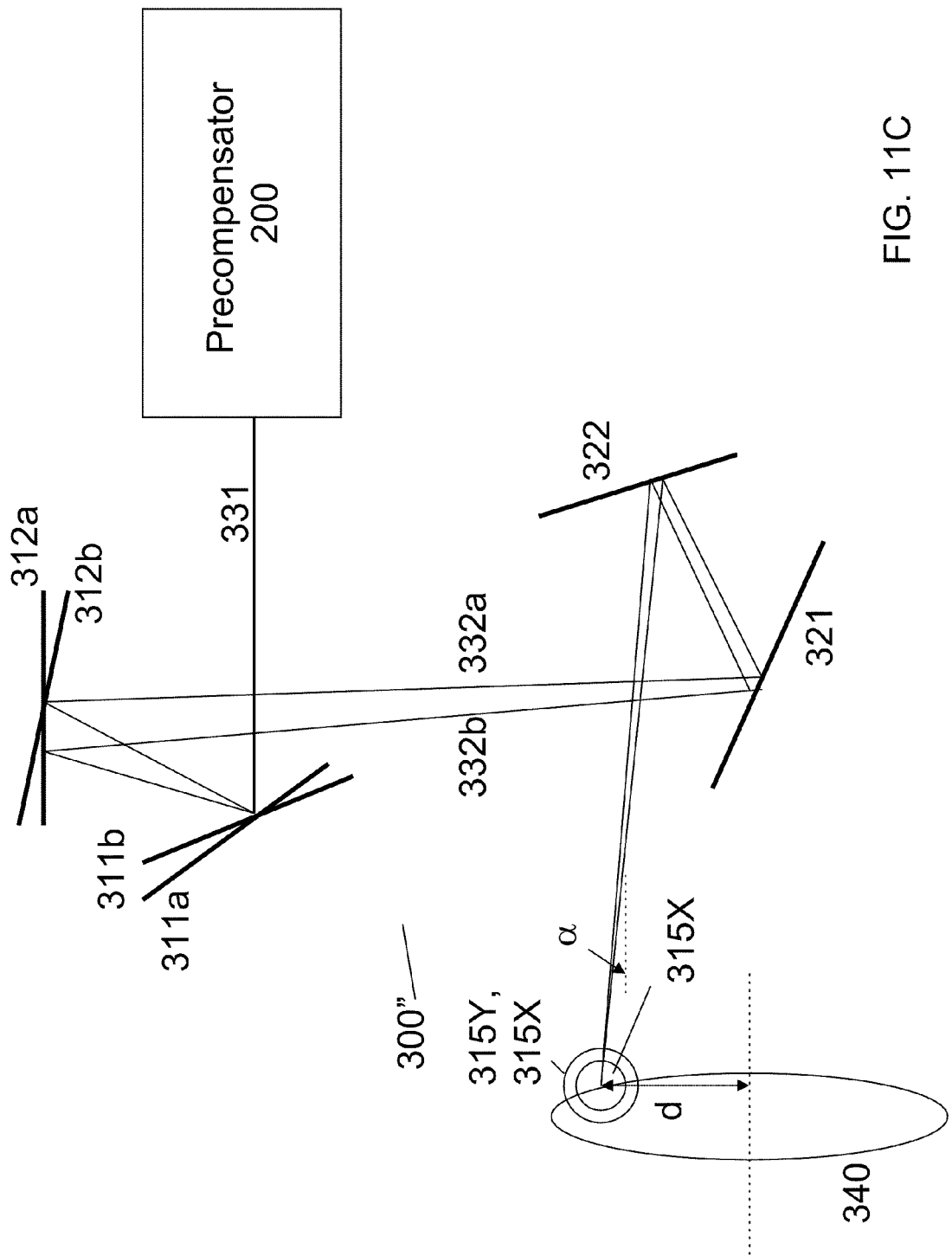

FIG. 11C illustrates a four mirror design to address this problem. In the XY Scanner 300'' the X scanner 310 again includes two X scanning mirrors 311 and 312. However, the Y scanner also includes two Y scanning mirrors, 321 and 322.

XY Scanner 300'' removes the Y scanner pivot point 315Y from the Y scanning mirror. Accordingly, XY Scanner 300'' can control the Y scanner, or output, pivot point 315Y to a predetermined location. An example is to move the Y scanning-output pivot point 315Y onto the entry pupil 340 of a subsequent lens group. In some implementations the X pivot point 315X can be also moved to the same location as well.

Other aspects of this design include that XY Scanner 300'' can control essentially independently (i) an angle α between the outputted scanned beam and an optical axis of the laser delivery system 1, and (ii) a location where the scanning beam impacts the entrance pupil of the subsequent optical element, characterized by a distance d from the optical axis. Because of the approximate independence of these controls, the XY Scanner 300'' can provide a scanning beam with minimized aberrations, as well as can control astigmatism and coma in the peripheral regions, including the peripheral regions of the surgical region.

Some implementations of XY Scanner 300''' include only one X scanning mirror 310 and one Y scanning mirror 320, each of them of the "fast steering" type. An individual fast steering mirror is capable of angular motion around two axes of rotation. A pair of these fast steering mirrors can also control the beam angle and the beam position in the plane transversal to the optical axis.

In some implementations the XY Scanner 300''' is configured to scan the laser beam over an XY scanning range whose maximum is longer than 5 millimeter and shorter than 15 millimeter at the focal plane of the laser system.

In some implementations the X pivot point generated by the first and second XY fast steering mirrors and the Y pivot point generated by the first and second XY fast steering mirrors coincide.

4. Z Scanner 450

As described above, ophthalmic surgical systems are configured to perform anterior segment surgery, or lens surgery by having a design which allows scanning a focal point over an interval much larger than the scanned interval in corneal procedures. In some implementations the Z scanning is performed over a Z scanning path within the Z scanning range of 5 mm to 10 mm, or 0 mm to 15 mm. (Throughout this application, the term "scanning within a range of x mm to y mm" refers to a scanning path whose initial value is x mm or more and ending value is y mm or less, encompassing all scanning paths which do not extend across the entire scanning range.)

Here, it is recalled that the "X, Y, Z" assignments are meant throughout the implementations in a broad sense. Z typically denotes an optical axis, which can be close to a geometrical axis. But the Z direction inside a target tissue, such as the eye, may not be fully parallel to the optical axis of the laser delivery system 1. Any compromise axis between these two can be also referred to as the Z direction. Also, the X, Y directions are not necessarily perpendicular to the Z axis. They can refer to any direction making a substantial angle with the Z direction. Also, in some implementations, a radial coordinate system may be more suitable to describe the scanning of the laser delivery system 1. In those implementations, the XY scanning refers to any scanning not parallel to the Z axis, parametrized by suitable radial coordinates.

FIG. 1 illustrates that some implementations of the laser delivery system 1 achieve these challenging large Z scanning ranges by including the First Beam Expander block 400 and the Movable Beam Expander block 500 in the Z Scanner 450. In various implementations, the First Beam Expander block 400 can be a movable block or a fixed block. The distance between the First Beam Expander block 400 and the Movable Beam Expander block 500 can be adjusted e.g. by a position actuator.

As was illustrated already in FIGS. 2A-B, as the focal point is moved away from its optimal position in the target tissue, the aberrations increase. These aberrations are typically called "geometric aberrations", as they can be understood from tracing geometric rays, and originate from the finite extent of the lenses. These geometric aberrations can be limited by making a numerical aperture of the Z Scanner 450 smaller. As such, the geometric aberrations depend both on the Z focal depth and the numerical aperture NA.

In addition, with decreasing numerical aperture NA, a second source of aberrations arises from the wave nature of light. These aberrations give rise to the so-called "diffraction aberration". This second type of aberration increases the focal spot radius with decreasing numerical aperture.

Figure 12A:
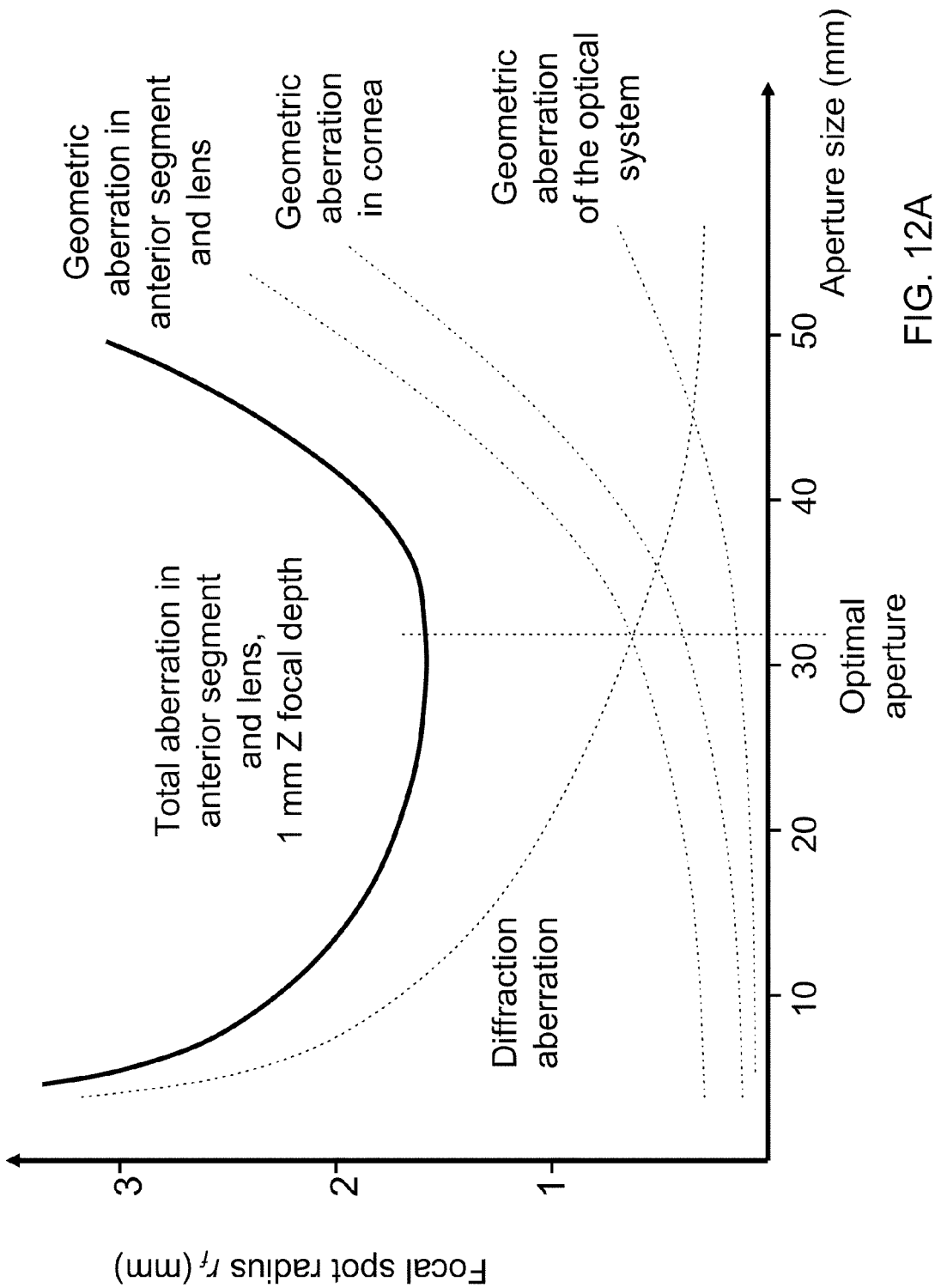
FIGS. 12A-D illustrate an aberration as a function of a numerical aperture and the corresponding optical numerical aperture $NA_{opt}(z)$ as a function of the Z focal depth.
Figure 12B:
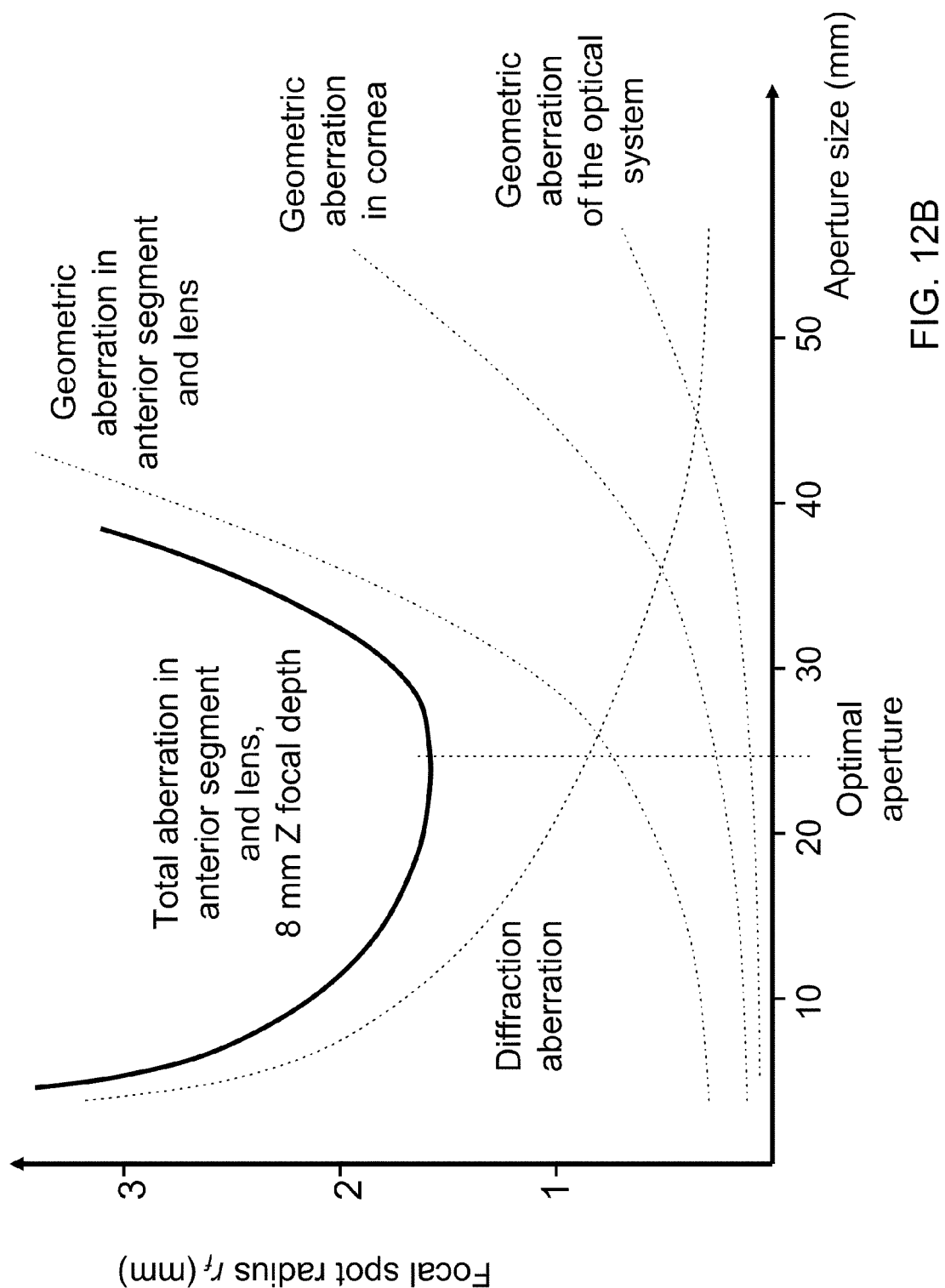

FIGS. 12A-B illustrate the geometric and diffraction aberrations in an anterior segment of an eye as a function of the aperture size of the Z Scanner 450, characterized by one of the above aberration measures: the focal spot radius $r_f$. Since the geometric aberration increases with the aperture size while the diffraction aberration decreases, a total aberration, defined as a sum of these two aberrations, exhibits an optimal minimum value at an optimal aberration and corresponding optimal numerical aberration $NA_{opt}$.

Here the usual definition connects the numerical aperture NA and the aperture size: NA=n*Sin Ar Tan(aperture size/(2*focal length)), where n is the refractive index of the material in which the image is formed.

These curves are for specific Z focal depths, 1 mm Z focal depth in FIG. 12A and 8 mm Z focal depth in FIG. 12B. As the geometric aberration is different at different Z focal depths, the minimum of the total aberration curve and thus the optimal aperture size and the optimal numerical aperture $NA_{opt}$ of the whole system depend on the Z focal depth: $NA_{opt}=NA_{opt}(z)$. In particular, the optimal aperture size and $NA_{opt}$ decreases for increasing Z focal depth, from 32 mm to 25 mm in this specific instance as the Z focal depth increases from 1 mm to 8 mm. Therefore, laser delivery systems which are intended to be used for both corneal and lens surgeries, need to cover a broader range of apertures and corresponding NA ranges. This requirement poses considerable design challenges.

As discussed further below, FIGS. 12 A-B also illustrate that the aberration exhibits a broad flat optimum for the typical corneal Z focal depths of 1 mm, while it exhibits a narrower, sharper minimum for Z focal depths typical for lens-surgery.

The aberration can be also characterized by the other three aberration measures S, ω, or $a_{40}$ as well, all yielding curves exhibiting an optimum. Any of the above four aberration measures can correspond to any of the five reference points P(1), ... P(5) described above, or can be an average taken over some or all of these reference points, or may correspond to other reference points.

In some implementations, in a wide range of Z focal depths, the aperture size and the corresponding NA can be adjusted to essentially the optimal numerical aperture $NA_{opt}(z)$, minimizing the total aberration, measured by an aberration measure. This functionality allows a strong reduction of the total aberration. Here, as before, the aberrations can be measured by one of the four aberration measures $r_f$, S, ω, or $a_{40}$, at any one of the above five reference points P1, ... P5.

The optimal aberration corresponds to a minimum of aberration measures $r_f$, ω, or $a_{40}$, or a maximum of the Strehl ratio S.

In some other implementations, where the optimal aberration may not be reached, or design considerations dictate that an aberration away from the optimal value should be used, the Movable Beam Expander Block 500 can still decrease the values of the aberration measures $r_f$, ω, or $a_{40}$ by at least a P(MovableExpander) percentage, or correspondingly increase the value of the Strehl ratio S by at least a P(MovableExpander) percentage, compared to the aberration measures of an essentially identical laser system where the second block of the Z Scanner 450 is not movable and thus the numerical aperture is not adjustable. In some implementations P(MovableExpander) can be 20%, 30%, 40%, or 50%. Here, as before, the aberration measures $r_f$, S, ω, or $a_{40}$, can be measured at any one of the five reference points P1, ... P5.

In some implementations, laser systems having the Z Scanner 450 with the adjustable numerical aperture NA can increase the Strehl ratio S above 0.8, relative to essentially identical laser systems where the Z scanner does not have an adjustable numerical aperture, having a Strehl ratio S below 0.8.

An additional design challenge is not only to minimize the total aberration at a fixed Z focal depth by adjusting the laser delivery system to its optimal aperture size and corresponding numerical aperture $NA_{opt}(z)$, but also to keep the system at least close to the Z dependent optimal numerical aperture $NA_{opt}(z)$ as the Z focal depth is scanned. In a typical implementation, the optimal numerical aperture decreases as the focal depth increases.

To address this variation of the optimal aperture as the Z focal depth is scanned within the Z scanning range, implementations of the laser delivery system 1 have the capability of changing the numerical aperture NA(z) as a separate parameter of the Z Scanner 450, essentially independently from varying the Z focal depth itself.

Implementations, where two quantities are controlled essentially independently, as presently the Z focal depth and the numerical aperture NA, typically have a pair of control parameters to achieve this modality. Examples include the pairing of a controllable distance between the First Beam Expander block 400 and the Movable Beam Expander block 500 and a position of a movable lens in either of these blocks, which can be adjusted by a secondary optical controller. Another example includes two movable lenses in any combination in the two blocks of the Z Scanner 450. It is recalled that the First Beam Expander block 400 can be implemented as a fixed block or a movable block.

In some implementations the numerical aperture NA can be adjusted to a sequence of optimal numerical aperture values $NA_{opt}(z)$, yielding a sequence of optimal total aberration values at a sequence of Z focal depth as the Z focal depth is scanned.

As before, the optimal total aberration can be captured by the minimum of any of the above aberration measures $r_f$, ω, or $a_{40}$, or the maximum of the Strehl ratio S. The Z scanning ranges can be e.g. 5-10 mm or 0-15 mm. The Z focal depth can be scanned at a radius r1=0 mm, or r2=3 mm, or at some other radius r, or at a variable radius r(z), bounded e.g. by r<3 mm.

Table 7 illustrates an example, where the second column describes the scanning of the Z focal depth within a Z scanning range of (−0.14 mm, 11.65 mm) in an ocular target tissue and the third column shows the corresponding values of $NA_{opt}(z)$. Implementations of the Z Scanner 450 are capable of adjusting the Z focal depth in this range and adjusting the numerical aperture NA to its optimal value $NA_{opt}(z)$ at these focal depths.

TABLE 7

| Z Position of Movable Expander 500 [mm] | Z focal depth [mm] | $NA_{opt}(z)$ |
|---|---|---|
| 0.00 | 11.65 | 0.17 |
| 5.00 | 9.68 | 0.18 |
| 10.00 | 7.94 | 0.19 |
| 15.00 | 6.43 | 0.20 |
| 20.00 | 5.12 | 0.22 |
| 25.00 | 3.98 | 0.23 |
| 30.00 | 3.00 | 0.25 |
| 35.00 | 2.16 | 0.27 |
| 40.00 | 1.44 | 0.28 |
| 45.00 | 0.83 | 0.30 |
| 50.00 | 0.30 | 0.32 |
| 55.00 | −0.14 | 0.34 |

In some other embodiments, the Z focal depth maybe scanned within a Z scanning range of 0 mm to 10 mm. In the course of scanning the numerical aperture may vary within a range of 0.4 to 0.1, in some other embodiments from 0.35 to 0.15.

Figure 12C:
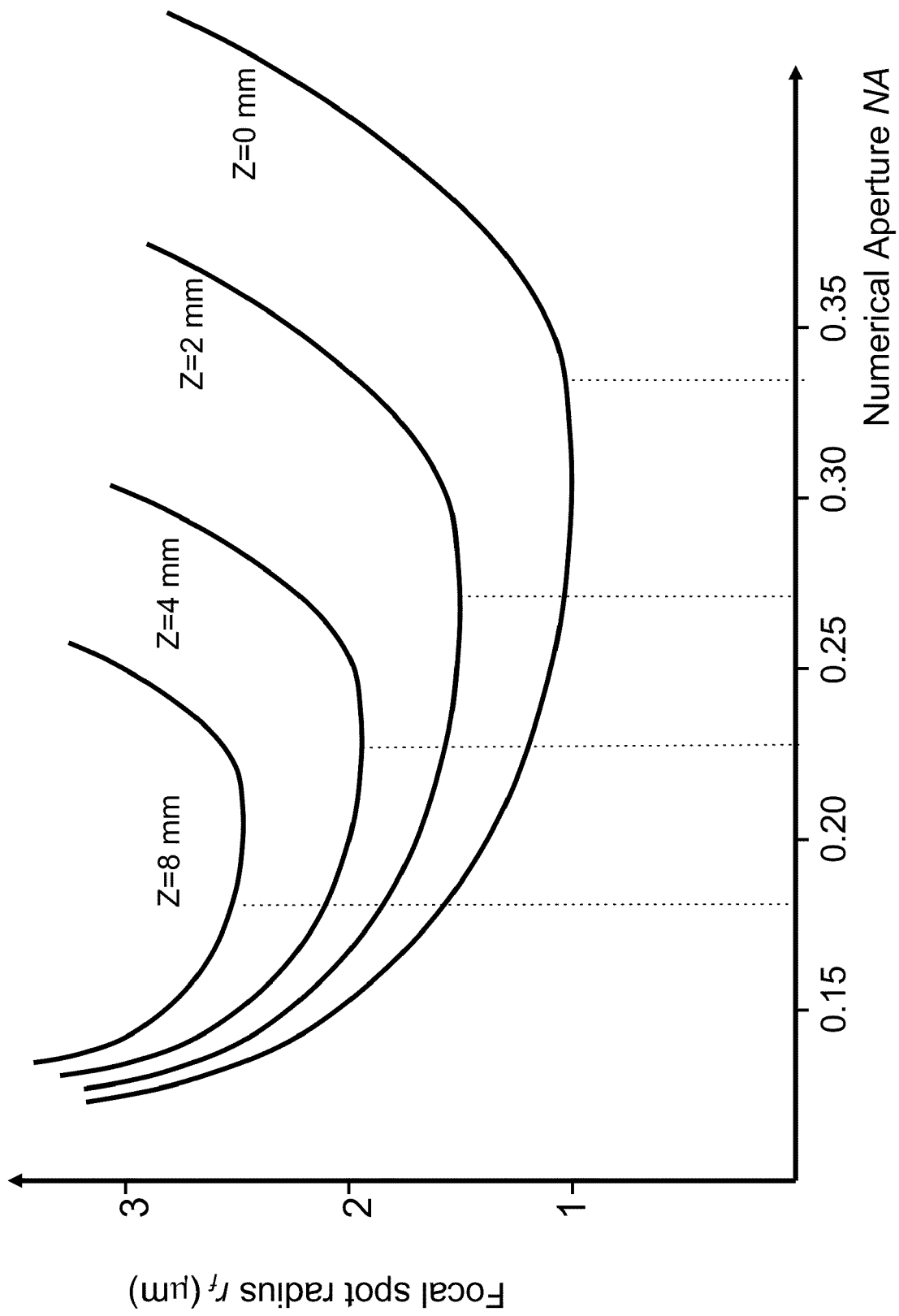

FIG. 12C illustrates an analogous sequence of aberration curves, corresponding to a sequence of Z focal depths of 8 mm, 4 mm, 2 mm, and 0 mm, exhibiting a sequence of corresponding optimal numerical apertures $N_{opt}(z)$.

Figure 12D:
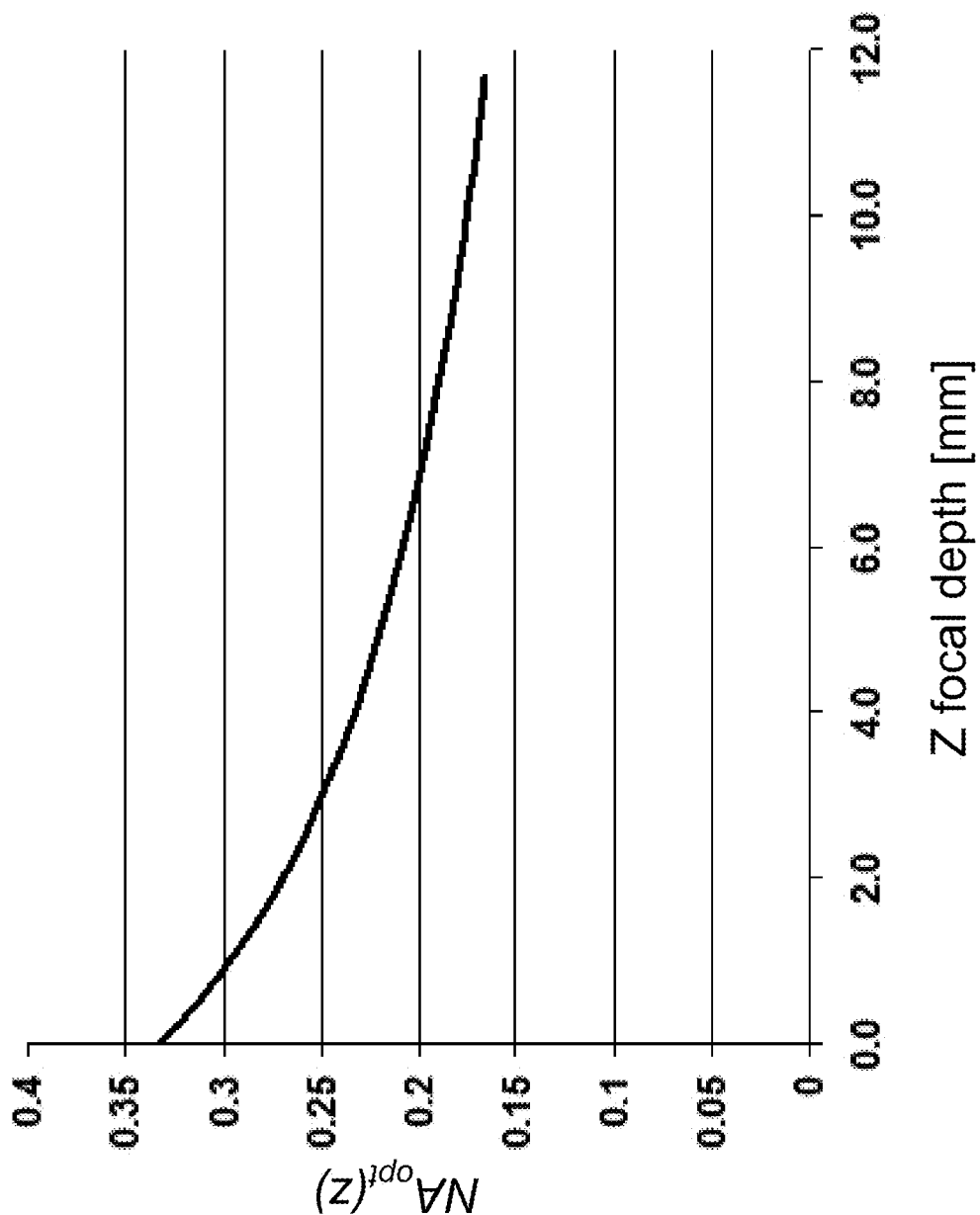

FIG. 12D illustrates explicitly the optimal numerical apertures $N_{opt}(z)$ as a function of the corresponding Z focal depths.

As described above, the separate adjustability of the Z focal depth and the numerical aperture NA typically requires two independently adjustable control parameters. Some implementations, however, may not offer the separate and independent adjustability of Z and NA. Instead, for every Z focal depth, these implementations adjust automatically the numerical aperture to either its optimal value $NA_{opt}(z)$, or at least to a vicinity of $NA_{opt}(z)$, without a separate NA adjusting step by an operator. For example, NA can track $NA_{opt}(z)$ within a P(track) percent, where P(track) can be 10%, 20%, or 30%.

These implementations can have only a single, integrated adjustable controller. In the just described example, this integrated controller may only display to a user of the system that it controls the Z focal depth in the target region. However, the controller may contain a coupled aperture adjuster, which simultaneously adjusts the numerical aperture NA to track $NA_{opt}(z)$ without a separate tuning step performed by the user of the laser delivery system 1.

In some implementations adjusting the distance between the First Beam Expander 400 and the Movable Beam Expander 500 may perform this functionality adequately. In other implementations, a single movable lens can offer this modality. In yet other implementations, a combination of two adjusters may be employed.

These implementations offer a simplified control function for the operator of the laser delivery system 1. Since achieving such a single, integrated control function is a design challenge, some implementations perform these integrated control functions in combination with the other blocks, such as the Precompensator 200, the XY Scanner 300 and the Objective 700.

In some implementations, where the optimal total aberration values cannot, or are not, achieved for various design considerations, the numerical aperture NA can be adjusted to a sequence of numerical aperture values at a sequence of Z focal depths along the Z scanning path within the Z scanning range to reduce the total aberration by at least a P(scan) percentage relative to laser systems whose Z Scanner 450 does not have an adjustable numerical aperture NA. In some implementations P(scan) can be 20, 30, 40, or 50 percent.

As before, the total aberration can be characterized by any on of the previously introduced aberration measures $r_f$, $\omega$, or $a_{40}$. Equivalently, the reduction of the aberration can be characterized by a corresponding increase of the Strehl ratio S. The Z scanning path can be a path parallel to the Z axis at a radius R from the optical, or Z axis of the laser system. In some implementations the Z scanning path can be located between radii r1=0 mm and r2=3 mm from the optical Z axis.

The total aberration can be measured in several different ways. The total aberration can refer to a total aberration averaged over the Z scanning path, or to the maximum or minimal value of the total aberration along the scanning path. The reduction of the total aberration can refer to any one of these possibilities.

In some implementations, the numerical aperture NA can be adjusted from a first value when a corneal procedure is performed to a second value when an anterior segment procedure is performed. In some implementations the first value is in the range of 0.2-0.5 and the second value is in the range of 0.1-0.3. In some other implementations the first value can be in the range of 0.25-0.35 and the second value can be in the range of 0.15-0.25.

The present implementation of the Z Scanner 450 is different from existing corneal laser delivery systems in several other ways, including the following.

1. In corneal laser delivery systems it is typically required that the numerical aperture does not change during the Z scan of the focal depth to ensure the simplicity of the design. This design is satisfactory for corneal surgery as the total aberration induced by the typical 1 mm Z scan is not a serious limiting factor of the precision of the corneal laser delivery systems. In contrast, implementations of the laser delivery system 1 have a variable numerical aperture NA to keep adjusting the aperture to its optimal aperture over the extensive surgical Z interval of e.g. 5-10 mm. This, of course, is achieved by the modality of the numerical aperture NA being adjustable essentially independently from the Z focal depth.

2. Also, typical existing corneal systems have their Z scanner in the Objective 700, or as a part of a complex implementation of the Objective 700, whereas the present Z Scanner 450 is disposed before the Objective 700. Here the Objective 700 denotes the final lens group of the laser delivery system 1 which is disposed in a functional mechanical housing separate from the functional mechanical housing of the XY Scanner and the Z Scanner. The term functional mechanical housing refers not to the overall housing of the delivery system, whose design can be dictated by ergonomic or appearance considerations, but to the housing which is holding together the lenses to perform their actual optical function. The Objective 700 of the present implementations is typically positioned in the optical pathway after the XYZ scanning beam, outputted by the Z Scanner 450, is deflected by the mirror 600.

3. FIGS. 12A-B illustrate a further challenge in the design of lens-surgical optical systems. Visibly, the total aberration exhibits a wide, flat optimal region for typical corneal Z focal depths of 1 mm, thus (i) the system parameters can be optimized for other considerations, (ii) a broad Z scanning range can be used, and (iii) less precise tuning of the system parameters is needed, all without much deterioration of the focal spot size. In contrast, for lens-surgical systems the focal spot size deteriorates quickly when (i) the system parameters are optimized for other considerations, (ii) a broader Z scanning range is implemented, and (iii) the system parameters are tuned less precisely.

In a further aspect of the embodiments of the Z Scanner 450, it is recalled that laser delivery systems which include an imaging sub-system or a visual observational optics sub-system, have the beams associated with either of these sub-systems coupled into the laser delivery system 1 through the mirror 600. The mirror 600 can be a dichroic mirror, for example. In typical surgical systems the Objective 700 refers to the lens group which is positioned after the mirror 600 in the optical pathway.

Implementing the Z Scanner 450 before the mirror 600 and separate from the Objective 700 is an important design consideration also because the weight of the Objective 700 is a critical factor, since the Objective 700 makes essentially direct contact with the target tissue, such as the eye of the patient. Therefore, minimizing the weight or mass of the Objective 700 makes implementations of the laser delivery system 1 impose a reduced pressure on the eye. And since this pressure deforms the eye itself and thus decreases the precision of the surgical procedure, designs which reduce the pressure on the eye increase the precision of the ophthalmic surgery considerably.

Tables 8-9 illustrate ranges of some relevant parameters for various embodiments of the First Beam Expander block 400 and the Movable Beam Expander block 500. The Beam Expander blocks each can have 2-10 lenses, in some embodiments 3-5 lenses, which are configured to carry out the above functionalities.

Table 8 illustrates a five lens embodiment of the First Beam Expander block 400 using an industry standard convention, describing groups of thick lenses in terms of the individual surfaces. First Beam Expander block 400 can include lenses 411, 412, 413, 414 and 415 with parameters in the following ranges (indicated by brackets):

TABLE 8

| Surface | Curvature [1/m] | Distance [mm] | Refractive Index n |
|---|---|---|---|
| 1 | (0, 1.5) | (5, 25) | (1.6, 1.93) |
| 2 | (22, 28) | (12, 22) | (1.6, 1.7) |
| 3 | (−17, −14) | (0.5, 12) | 1 |
| 4 | (7.0, 8.5) | (15, 29) | (1.65, 1.8) |
| 5 | (−19, −13) | (3, 14) | 1 |
| 6 | (14, 18) | (8, 12) | (1.6, 1.7) |
| 7 | (0, 9.3) | (6, 12) | 1 |
| 8 | (−28, −21) | (1, 5) | (1.65, 1.75) |
| 9 | (−15, −6) | | |

In some embodiments, the First Beam Expander block 400 includes, sequentially from an input side facing the XY Scanner 300: a first lens group with a positive refractive power, a meniscus lens, having a convex surface facing the input side, and a second lens, having a concave surface facing the input side.

Other implementations are related to the implementations of Table 8 by a scale factor a, having five scaled lenses, the curvatures of the second column being multiplied by a, the distances of the third column multiplied by 1/a, and having unchanged indices of refraction n. The scale factor a can assume values between 0.3 and 3.

Table 9 illustrates a four lens embodiment of the Moving Beam Expander block 500, including lenses 511, 512, 513, and 514, with parameters in the following ranges:

TABLE 9

| Surface | Curvature [1/m] | Distance [mm] | Refractive Index n |
|---|---|---|---|
| 1 | (−25, −10) | (3, 7) | (1.7, 1.8) |
| 2 | (−25, −28) | (0, 2) | 1 |
| 3 | (−43, −24) | (1.5, 5) | (1.5, 1.62) |
| 4 | (8.5, 19.4) | (26, 31) | 1 |
| 5 | (−6.2, −4.6) | (10, 16) | (1.53, 1.6) |
| 6 | (−18.4, −14.7) | (34, 49) | 1 |
| 7 | (1.9, 4.2) | (8, 14) | (1.58, 1.61) |
| 8 | (−11, −9.0) | | |

Some implementations of the Movable Beam Expander block 500 include, sequentially from an input side facing the First Beam Expander block 400: a meniscus lens, having a concave surface facing the input side, a negative lens with a negative refractive power, and a positive lens group with a positive refractive power.

Other implementations are related to the implementations of Table 9 by a scale factor a, having four scaled lenses, having the curvatures of the second column being multiplied by a, the distances of the third column multiplied by 1/a, and having unchanged indices of refraction n. The scale factor a can assume values between 0.3 and 3.

Figure 13A:
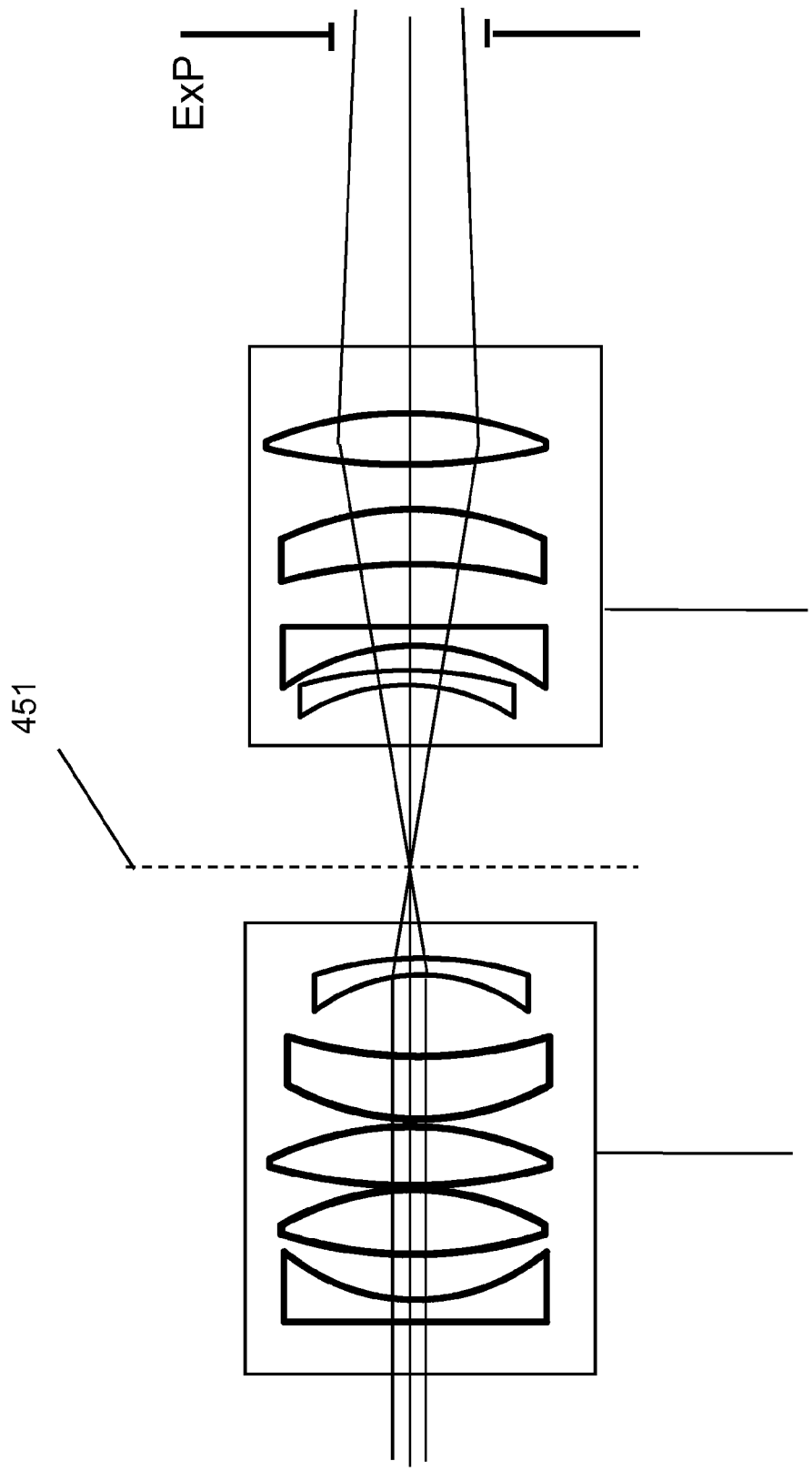
FIGS. 13A-B illustrate two settings of the First Beam Expander block 400 and the Movable Beam Expander block 500.
Figure 13B:
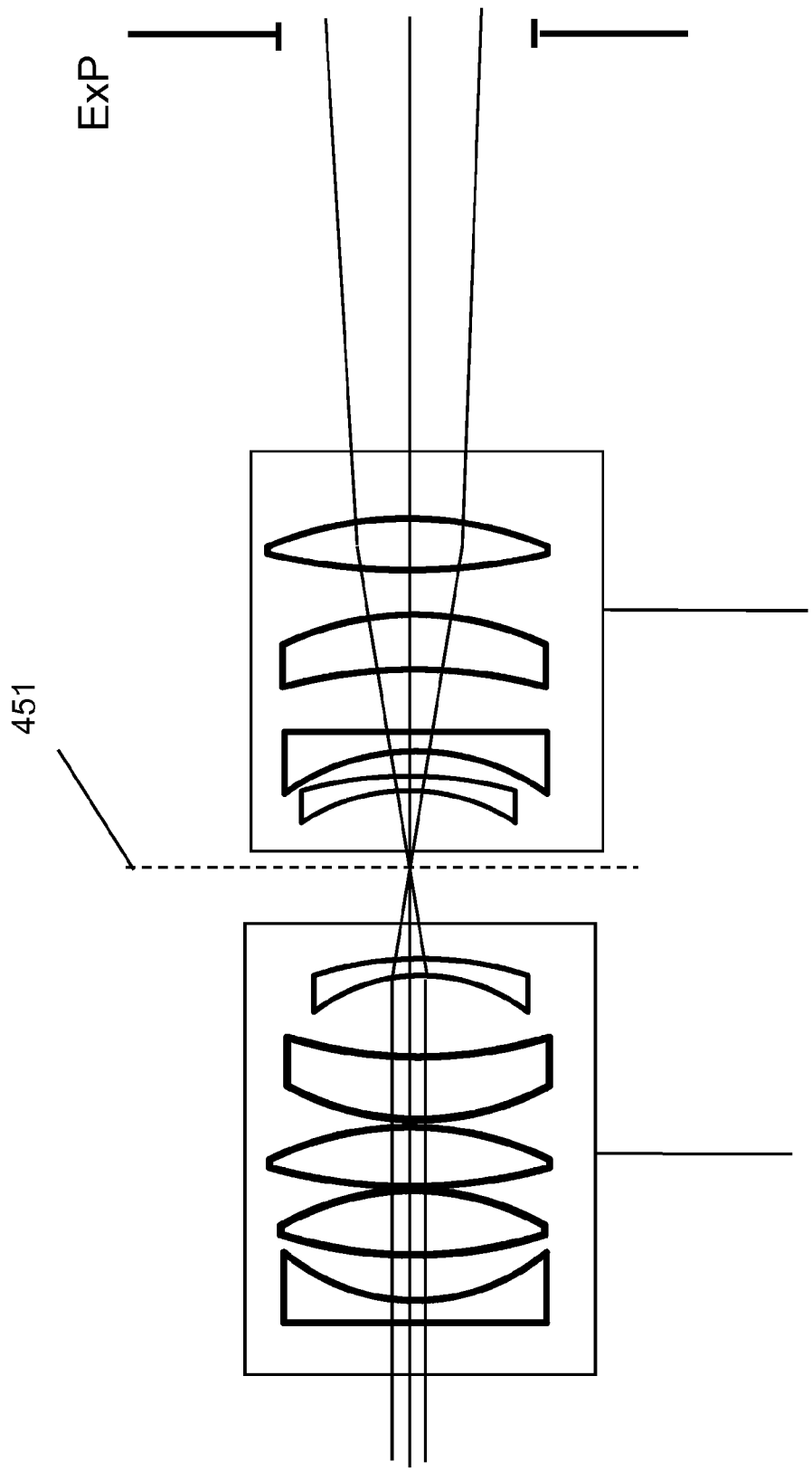

FIGS. 13A-B illustrate embodiments of Tables 8-9 in two configurations with different distances between the First Beam Expander block 400 and the Moving Beam Expander block 500. In some implementations, the Moving Beam Expander block 500 can be moved relative to the First Beam Expander block 400 by a distance in the range of d=5-50 mm.

These figures illustrate the design considerations of the Z Scanner 450 at work.

FIG. 13A illustrates the case when the Movable Beam Expander block 500 is in a position relatively far from the First Beam Expander block 400. In this case the beam exiting the combined assembly has (i) convergent rays, (ii) a relatively large diameter at an exit pupil ExP, (iii) a shallower Z-depth of the focal spot when a fixed focal length objective is placed near the exit pupil of the Z Scanner 450, and thus (iv) the focal spot is formed by a beam with a higher numerical aperture NA.

FIG. 13B illustrates the case when Movable Beam Expander block 500 is closer to the First Beam Expander 400 than in the case of FIG. 13A. Here the beam has (i) divergent rays, (ii) a smaller diameter at the exit pupil ExP, (iii) a deeper Z-depth of the focal spot when a fixed focal length objective is placed at the exit pupil of the Z Scanner 450, and thus (iv) the focal spot is formed by a beam with a smaller numerical aperture NA.

In summary, at shallower Z focal depths the focal spot is created by a large NA beam, whereas for increasing Z focal depths the numerical aperture NA decreases. The relative change in the numerical aperture NA can be optimized by optimizing the location of the exit pupil ExP of the Beam Expander blocks 400 and 500 and the location of the entrance pupil of the focusing Objective 700. These implementations are alternative ways for optimizing the numerical aperture at different focal depths even without use of the functionalities of the pre-compensator 200.

As discussed above, the numerical aperture NA can be extensively adjusted with or without the Precompensator 200. In the overall laser delivery system 1 the numerical aperture NA can be adjusted by controlling the Precompensator 200, the First Beam Expander block 400 or the Movable Beam Expander block 500, or by controlling these blocks in combination. The actual choice of implementation in practice depends on other higher level system level requirements, such as scanning range, scanning speed, and complexity. Implementations with other numerical ranges can also be configured to perform some or all of the above described functionalities.

Figure 14:
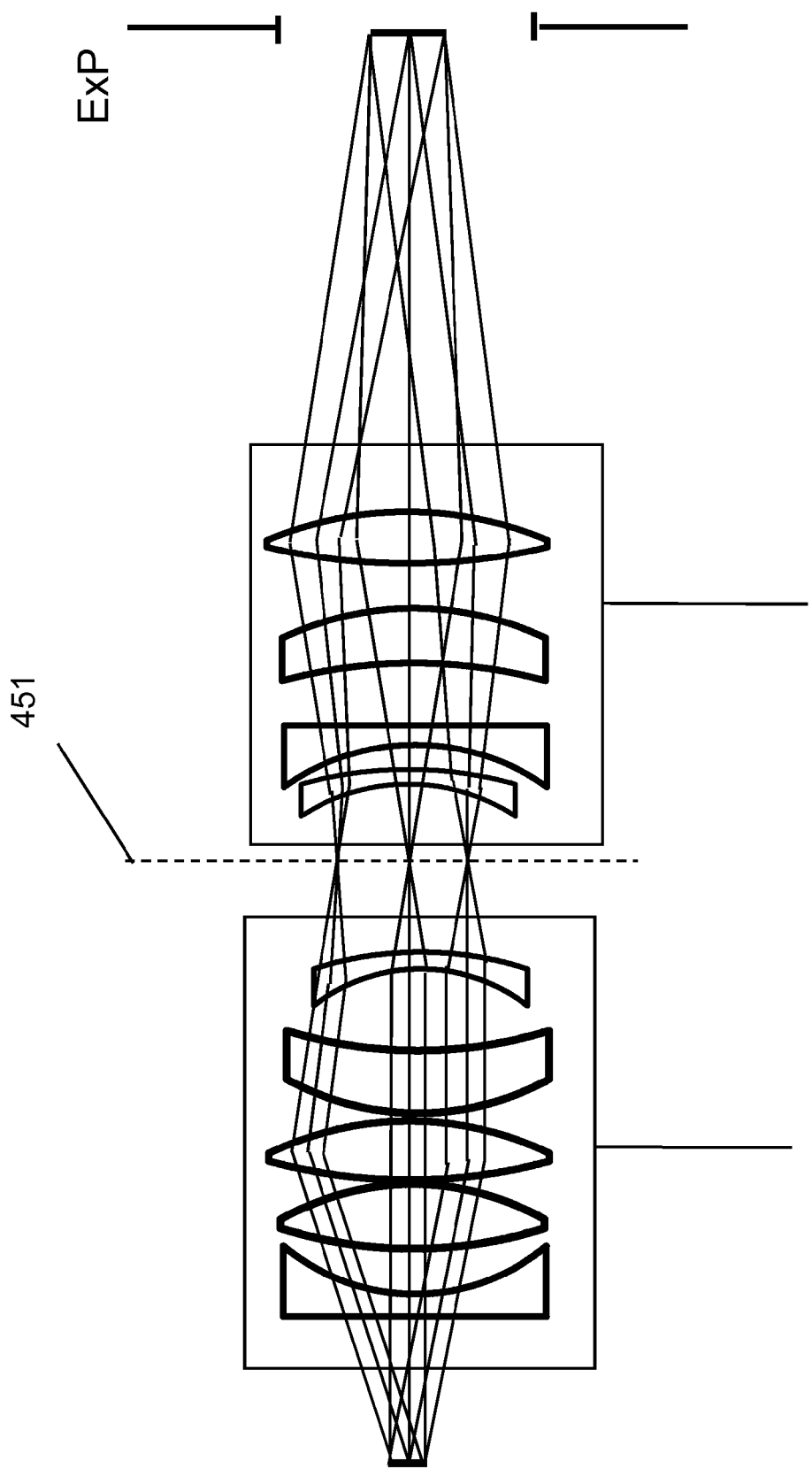
FIG. 14 illustrates the intermediate focal plane of the Z Scanner 450.

FIG. 14 illustrates a further aspect of the Z Scanner 450. Three different characteristic beams are shown, emanating from an exit pivot point PP(XY) of the XY Scanner 300. Remarkably, all three characteristic beams are focused into an entrance pivot point PP(O) of the Objective 700 by the Z Scanner 450. The position of PP(O) can be adjusted e.g. by moving the Movable Beam Expander 500.

As discussed below, laser delivery systems which generate a pivot point PP(O) located off the mirrors of the XY Scanner 300 have useful features e.g. in embodiments where the PP(O) pivot point falls inside the Objective 700.

In other embodiments, the XY Scanner 300 has an exit pivot point PP(XY) farther than the distance to the Z Scanner 450. In these embodiments, the Z Scanner 450 only modifies the exit pivot point PP(XY) of the XY Scanner 300 into the entrance pivot point PP(O) of the Objective 700.

In either case, these implementations make use of the existence of an intermediate focal plane 451, located between the First Beam Expander block 400 and the Movable Beam Expander block 500. The existence of this intermediate focal plane 451 is indicated by the focal points of the three characteristic beams lining up laterally with essentially the same z coordinate. Conversely, implementations which do not possess such an intermediate focal plane are not well suited to have an adjustable pivot point PP(O).

5. Objective 700

In some implementations the laser beam outputted by the Z Scanner 450 is deflected by the Beam Splitter/Dichroic Mirror 600 onto the Objective 700. Through this mirror 600 various auxiliary lights can also be coupled into the laser delivery system 1. The auxiliary light sources can include light associated with an optical coherence tomography imaging (OCT) system, an illumination system and a visual observational block.

The Objective 700 can provide a shared optical pathway for an XYZ scanned laser beam, propagating from the laser engine 100 through the XY Scanner 300 and the Z Scanner 450, and the auxiliary light into the surgical target region. In various implementations, the Objective 700 may include objective lens groups. In several implementations the lenses of the objective lens groups do not move relative to each other. As such, while the Objective 700 is an integral part of the Z scanning functionality, it does not contribute to the Z scanning in a variable or dynamic manner. In these implementations no lens position is adjusted in the Objective 700 to move the Z focal depth of the focal spot.

Implementations of the Objective 700 can control at least one of a spherical aberration, coma, and higher order aberrations of the surgical pulsed laser beam.

Since the Objective 700 is guiding lights of different wavelength, implementations of the Objective 700 use achromatized lens groups. The wavelength of the auxiliary light can be e.g. in the range of 0.4 micron to 0.9 micron, and the wavelength of the surgical light can be in the 1.0-1.1 micron range. Implementations of the Objective 700 keep the chromatic aberrations below a predetermined value throughout the range of wavelengths of the used lights, such as 0.4 micron to 1.1 micron in the above example.

The weight or mass of the Objective 700 is an important consideration. In some implementations the objective is in mechanical contact with the eye of the patient. As such, it exerts pressure on the eye. This pressure can distort the eye from its relaxed configuration, making it more difficult to select targets and direct the surgical laser beam accurately.

Furthermore, if the patient moves during the surgical procedure, it may be preferable that the objective can move with the smallest resistance in response to the patient's movement. Although the weight of the objective can be statically balanced with a spring system or counterbalance, these measures may not reduce the dynamic or inertial forces. In fact, these forces may be increased by such measures. All of these considerations point toward the usefulness of reducing the weight or mass of the Objective 700.

There are numerous ways to identify critical forces and corresponding objective masses in relation to eye surgical procedures. A review of various impacts on the eye was published e.g. in *Determination of Significant Parameters for Eye Injury Risk from Projectiles*; Duma S M, Ng T P, Kennedy E A, Stitzel J D, Herring I P, Kuhn F. *J. Trauma*. 2005 October; 59(4):960-4. This paper reviewed objects impacting an eye and provided critical energy values of the impacting objects, corresponding to (i) different types of damage to the eye, including minor injuries like corneal abrasions, moderate ones like lens dislocations, and grave injuries like retinal damage. The paper also assigned a probability of injury, from (ii) low, representing a few percent chance, to medium, representing an about 50% chance, to high, referring to a near certainty of injury. The paper further classified (iii) the impact scenarios according to the shape of the impacting object, categorizing according to total impacting energy and impacting energy normalized by the impact area.

These results can be applied to the specific case of eye surgery by investigating the possibly highest impact injury, caused by a total breakdown of the mechanical support system of the Objective 700. Such a breakdown may result in a freefall of the entire Objective 700 over a typical vertical path of 20-25 mm, transferring all of the objective's energy to the eye itself. Critical masses can be computed from the published critical energy values modeling the freefall of the objective according to known physical principles.

A vertical path of this length can emerge from the following design principles. The Objective 700 can be mounted on a vertical sliding stage to provide a safe and reliable docking of the laser delivery system 1 by a gantry to the eye. Such designs ease precision and force requirements on the gantry because the vertical gantry accommodates the Objective 700 to be positioned within the vertical travel range. Further, once the eye is docked, these designs allow the eye to move vertically relative to laser source 100 without breaking the attachment of the eye to the laser delivery system 1. These movements may occur due to movement of the patient or movement of the surgical bed. A vertical travel range of 20 to 25 mm of the Objective 700 mitigates effectively and safely against gantry forces and patient motion within this range.

Finally, (iv) a design consideration also influences the critical masses in the sense that the ("optical") mass of the optical elements of the Objective 700, such as the glass lenses alone in the objective lens groups define a lower bound on the mass of the entire objective, as there are numerous ways to reduce the mass of the housing and the control systems of the objective, while it is much harder to reduce the mass of the lenses. In present systems the total mass of the objective can be two-three times the "optical" mass of the lenses alone.

Some of these criteria yield sharper definitions of critical masses, others only a smooth crossover dependence, not lending themselves to a sharp definition.

From all the possible combinations of the above (i)-(iv) classifications, four relatively sharp and meaningful definitions of critical masses MC can be identified as follows:

(1) MC1~400 grams: objectives with masses M<MC1 pose essentially no risk of injury for a patient even in a worst case breakdown scenario;

(2) MC2~750 grams: masses in the MC1<M<MC2 regime can have a larger than 10% chance of causing some corneal abrasions via the total impacting energy;

(3) MC3~1,300-1,400 grams: masses in the MC2<M<MC3 regime may have a 50% chance of causing corneal abrasions in any impacting scenario; and finally (4) MC4~3,300 grams: masses in the MC3<M<MC4 range in some impacting scenarios can cause a near certain corneal abrasion, and can develop a non-zero chance of injuries of medium severity or worse.

All of these probabilities, of course, are to be multiplied with the small probability of the total breakdown of the mechanical support system of the objective actually occurring. However, in ophthalmic applications extreme measures need to be taken to guard against all conceivable injury scenarios, however unlikely, making the above critical masses relevant.

Therefore, the above considerations identify four critical masses according to clear criteria, regarding total and optical masses of the Objective 700. Accordingly, embodiments of the Objective 700 where the design process manages to reduce the objective mass below any one of the above critical masses MC4, . . . , MC1, offer qualitatively better chances for safe surgical procedures.

Existing objectives for femtosecond ophthalmic lasers have a mass above 5000 grams, considerably above even the largest of these four critical masses. An exception is US patent application 20030053219 by Manzi, which describes a lens system where the optical mass of the lenses alone is about 1000 grams, possibly leading to a total mass of 2,000-3,000 grams. While Manzi's design is lighter than other existing objectives, it is still quite massive. This is primarily due to a Z scanner being an integral part of the objective since lens elements inside the objective are used for Z focus control. Additional mass is required by Manzi for the precision machined housing, for a precision linear guide for the lenses, and for a servo motor, all increasing the total mass to values back above 5000 grams.

In contrast, a mass of various embodiments of the Objective 700 can fall in any of the above four mass ranges: 0-400 grams, 400-750 grams, 750-1,350 grams, and 1,350-3,300 grams. The mass can be either the optical or the total mass. E.g. the lenses in an implementation of the Objective 700 can have a mass of less than 130 grams. It is feasible to mount these lenses in a precision metal housing for a total assembly mass of 400 grams.

Embodiments of the Objective 700 achieve such a remarkable mass reduction to below 400 grams, 750 grams, 1,350 grams and 3,300 grams by removing the Z scanning functionality to the separate Z Scanner 450, housing it in a separate functional or mechanical housing. Here the term "functional or mechanical housing" refers to the fact that overall, non-functional design considerations may result in disposing the separate Z Scanner 450 into the same general container as the Objective 700, but such a general container does not serve an optical function or mechanical purpose.

In some embodiments, a mass of the Objective 700 can be reduced by a P(mass) percentage in comparison to analogous objectives, which perform at least some of the dynamic Z scanning functionality by adjusting an optical characteristic of the Objective 700. Such characteristic can be the entire Z Scanner 450 being integrated into the Objective 700, or the Movable Beam Expander block 500 being integrated into the Objective 700, or one or more movable scanning lens being integrated into the Objective 700. P(mass) can be 10%, 50%, or 100%.

Another related aspect of the Objective 700 and the corresponding design of the surgical laser system 1 was described in relation to FIG. 14, where it was shown that embodiments of the Z Scanner 450 can focus the XYZ scanned laser beam onto the objective's entrance pivot point PP(O). Embodiments, which have the entrance pivot point PP(O) inside the Objective 700 have a much-reduced beam radius rb over a large fraction of the optical pathway, as the beam converges towards this internal pivot point PP(O). In turn, a beam with a reduced beam radius rb can be controlled by smaller lenses, resulting in significant reduction of the overall mass of the Objective 700.

Figure 15:
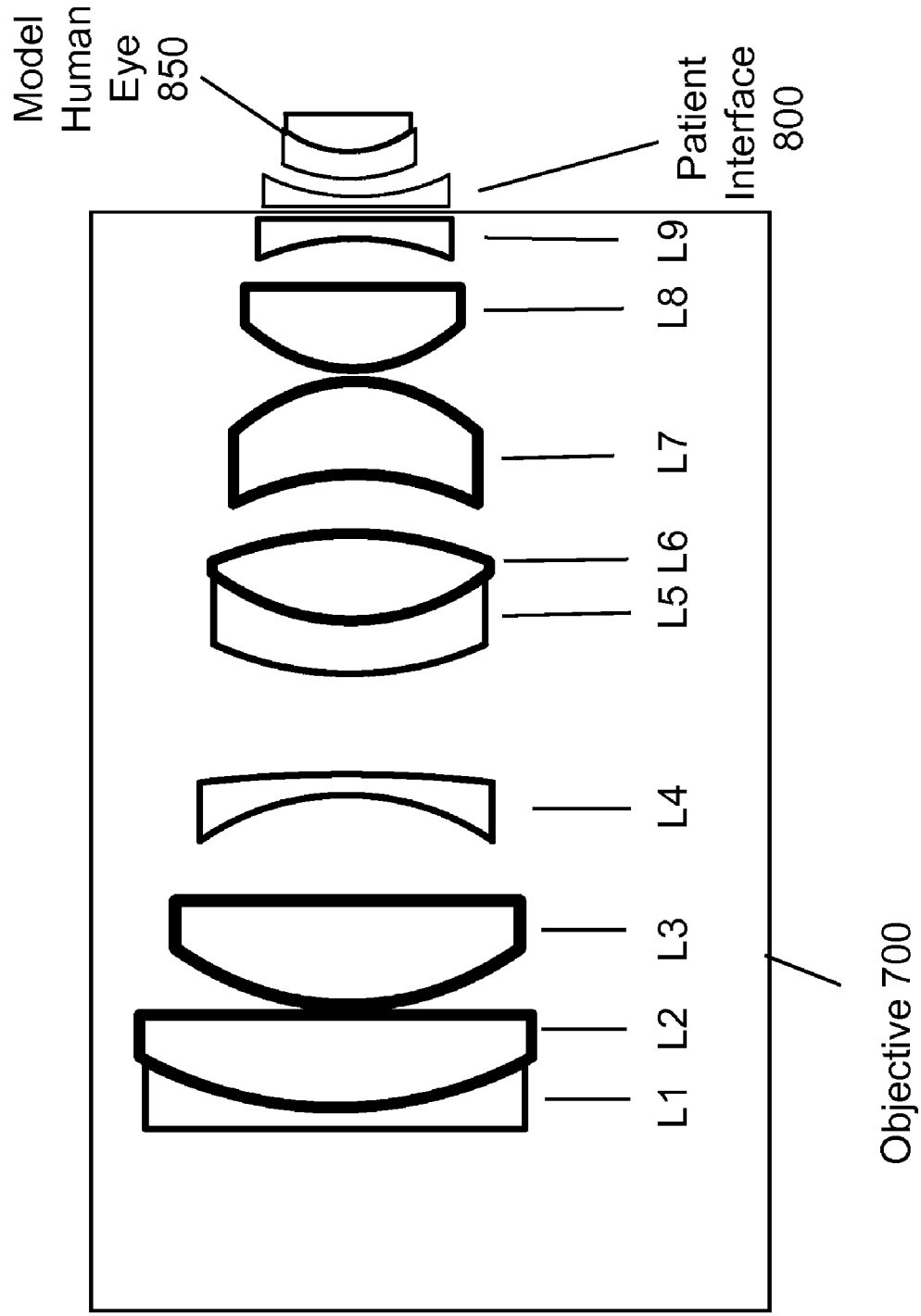
FIG. 15 illustrates an implementation of the Objective 700.

An implementation of the Objective 700 according to the above design insights is summarized in Table 10 and illustrated in FIG. 15. Implementations of the Objective 700 include a first lens group, to receive the surgical pulsed laser beam from the Z Scanner 450, and a second lens group, to receive the surgical pulsed laser beam from the first lens group and to focus the surgical laser beam onto a target region.

Table 10 illustrates the Objective 700 of FIG. 15 in more detail via surfaces 1 trough 16. The Objective 700 has nine lenses L1-L9 and interfaces with the Patient Interface 800 via surface 17. As before, the brackets indicate the ranges the corresponding parameters can assume. (Surfaces 1 and 2 define a doublet of lenses L1/L2 and surfaces 8 and 9 define a doublet of lenses L5/L6, hence the 16 surface instead of 18.)

TABLE 10

| Surface | Curvature [1/m] | Distance [mm] | Index of refraction n |
| --- | --- | --- | --- |
| 1 | (−1.5, 4.5) | (1, 6) | (1.7, 1.9) |
| 2 | (7.8, 45) | (6.4, 13) | 1.56, 1.8) |
| 3 | (−4.2, 3.2) | (0, 3.2) | 1 |
| 4 | (22, 36) | (10.5, 14) | (1.47, 1.62) |
| 5 | (−10, 5) | (0, 6.8) | 1 |
| 6 | (−27.2, −12.6) | (8.0, 11.6) | (1.58, 1.63) |
| 7 | (−30.3, 2.5) | (0, 6.7) | 1 |
| 8 | (−3.1, 18.9) | (4.0, 8.3) | (1.65, 1.76) |
| 9 | (40.7, 72) | (8.2, 17.9) | (1.57, 1.69) |
| 10 | (−28.3, −22.1) | (0, 3) | 1 |
| 11 | (−37.8, −17.6) | (3.0, 26) | (1.70, 1.86) |
| 12 | (−6.3, 14.0) | (0, 3.0) | 1 |
| 13 | (37.9, 65) | (12.0, 22.3) | (1.54, 1.72) |
| 14 | (−15.4, 5.2) | (0, 6.5) | 1 |
| 15 | (−55.1, −21.6) | (2.0, 4.7) | (1.56, 1.85) |
| 16 | (11.4, 26.8) | (0, 2.0) | 1 |
| 17 | (−60.0, 0) | (1.0, 1.5) | (1.47, 1.54) |

In other implementations, different number of lenses can be used with different parameter ranges, which satisfy the above design considerations comparably well.

In some implementations the Objective 700 can be described in terms of lens groups. For example, the Objective 700 can include a first lens group, to receive the XYZ scanned laser beam from the Z Scanner 450, and a second lens group, to receive a laser beam from the first lens group. The second lens group can include a first lens with an index of refraction in the range of 1.54 to 1.72, an entry surface with a curvature in the range of 37.9 to 65 l/m and an exit surface with a curvature in the range of −15.4 to 5.2 l/m. Further, the second lens group can also include a second lens, separated from the first lens by a distance in the range of 0 to 6.5 mm, with an index of refraction in the range of 1.56 to 1.85, an entry surface with a curvature in the range of −55.1 to −21.8 l/m and an exit surface with a curvature in the range of 11.4 to 26.8 l/m. The Objective 700 can output the laser beam onto the patient interface 800 through the second lens.

In some implementations an effective focal length of the Objective 700 is less than 70 mm.

In some embodiments a distance from the Objective 700 to the patient interface 800 is less than 20 mm.

In some designs a curvature of a focal plane of the laser delivery system 1 is larger than 20 l/m.

ments NA and S assume values in the same respective ranges "around" these specific radial coordinates. In some cases the term "around" refers to a range of radial coordinates within the P(radial) percent of the shown radial coordinate values, where P(radial) can be one of 10%, 20% and 30%. E.g. points having a z radial coordinate in the range of 7.2 mm and 8.8 mm are within the P(radial)=10% vicinity of the z=8.0 mm radial coordinate of the "lens, center" reference point.

Furthermore, in some embodiments, NA and S fall in only one of their three respective ranges listed for the B, C, and D configurations. In some other embodiments, NA and S fall into two of their three respective ranges, listed for the B, C, and D configurations in Tables 11A-B.

Visibly, the described laser delivery system is well corrected to essentially a diffraction limited optical performance throughout the entire lens-surgical volume.

TABLE 11A

| Configuration | Tissue, location | Depth z [mm] | Radius r [mm] | Numerical aperture NA | Strehl ratio S |
|---|---|---|---|---|---|
| A | Cornea, center | 0.3 | 0 | (0.25, 0.40) | (0.90, 1.0) |
| B | Cornea, periphery | 0.3 | 6.2 | (0.25, 0.40) | (0.90, 1.0) |
| C | Lens, center | 8 | 0 | (0.15, 0.35) | (0.90, 1.0) |
| D | Lens, periphery | 7.3 | 4 | (0.15, 0.35) | (0.80, 1.0) |

TABLE 11B

| Configuration | Tissue, location | Depth z [mm] | Radius r [mm] | Numerical aperture NA | Strehl ratio S |
|---|---|---|---|---|---|
| A | Cornea, center | 0.3 | 0 | (0.30, 0.35) | (0.95, 1.0) |
| B | Cornea, periphery | 0.3 | 6.2 | (0.30, 0.35) | (0.90, 0.95) |
| C | Lens, center | 8 | 0 | (0.20, 0.25) | (0.95, 1.0) |
| D | Lens, periphery | 7.3 | 4 | (0.20, 0.25) | (0.85, 0.90) |

Numerous other implementations of the Objective 700 and the entire surgical laser system 1 can be also created to adhere to the design principles expressed throughout this application by using commercially available optical design software packages such as Zemax from Zemax Development Corporation or Code V from Optical Research Associates.

6. Overall System Optical Performance

In the various implementations, the parameters of the subsystems Precompensator 200, XY Scanner 300, Z Scanner 450 and Objective 700 can be optimized in an interdependent manner so that the optical performance of the overall laser delivery system 1 may exhibit properties which are uniquely useful for e.g. ophthalmic surgical applications.

Tables 11A-B summarize the optical performance of the overall laser delivery system 1 in a first and a second implementation in terms of the numerical aperture NA and the Strehl ratio S. The optical performance is again characterized at reference points, in analogy to the above reference points P1, . . . P5. Tables 11A-B show the optical performance of the laser delivery system 1 with its components in configurations A, B, C, and D, delivering the laser beam to a center of the cornea (A), a periphery of the cornea (B), a center of the lens (C) and a periphery of the lens (D), respectively. These reference points represent a large surgical volume, associated with the challenge of performing ophthalmic surgery on the crystalline lens.

Tables 11A-B show the radial coordinates of the reference points having specific values. However, in other embodi- Analogous designs, which have a Strehl ratio S higher than 0.8 can be considered equivalent to the above listed designs, as all of these designs are considered diffraction limited systems.

Other aberration measures, such as the focal spot radius $r_f$ can be also used besides the Strehl ratio S to characterize the overall optical performance of the laser delivery system 1. Since large Strehl ratios combined with large numerical apertures NAs translate to small focal spot radii $r_f$, throughout the configurations A-D the focal spot radius $r_f$ can stay below 2 microns in some implementations, in others below 4 microns, in yet others below 10 microns in the ocular target region.

To characterize the laser delivery system's performance more accurately, and to represent the substantial impact of the cornea and lens on the beam propagation, the NA and S values of Tables 11A-B have been derived by designing the system including the eye as an integral part of the optical design. In some designs, the eye is modeled in its natural form. In others, a degree of applanation of the eye is included, to represent authentic surgical condition.

Table 12 summarizes a simple model of the relevant ocular tissues, as shown by Model human eye 850 in FIG. 15. (The numbering of the surfaces was chosen to continue the numbering of Table 10, starting with surface 18, the surface connecting the Patient Interface 800 to the corneal tissue.) The ocular tissue can be modeled by a 0.6 mm thick cornea (entered from the Patient Interface via shared surface 18), aqueous humor (entered from the cornea via surface 19) and the crystalline lens (entered from the aqueous humor via surface 20). The separations of the ocular surfaces are treated similarly to the separations of the lens surfaces 1-16.

TABLE 12

| Surface | Curvature [1/m] | Distance [mm] | Index of refraction n |
|---|---|---|---|
| 18 | (−100, −80) | 0.6 | 1.38 |
| 19 | (−100, −80) | (2.0, 4.0) | 1.34 |
| 20 | (−100, −80) | (3.0, 5.0) | 1.42 |

The NA and S values of Tables 11A-B were calculated using this model of the ocular tissue. Related models of the eye result in comparable aberration measures.

In a separate further aspect, in some implementations of the optical design of the entire laser delivery system 1 can be simplified by leaving some of the distortions and field curvatures uncorrected by optical means.

Figure 16:
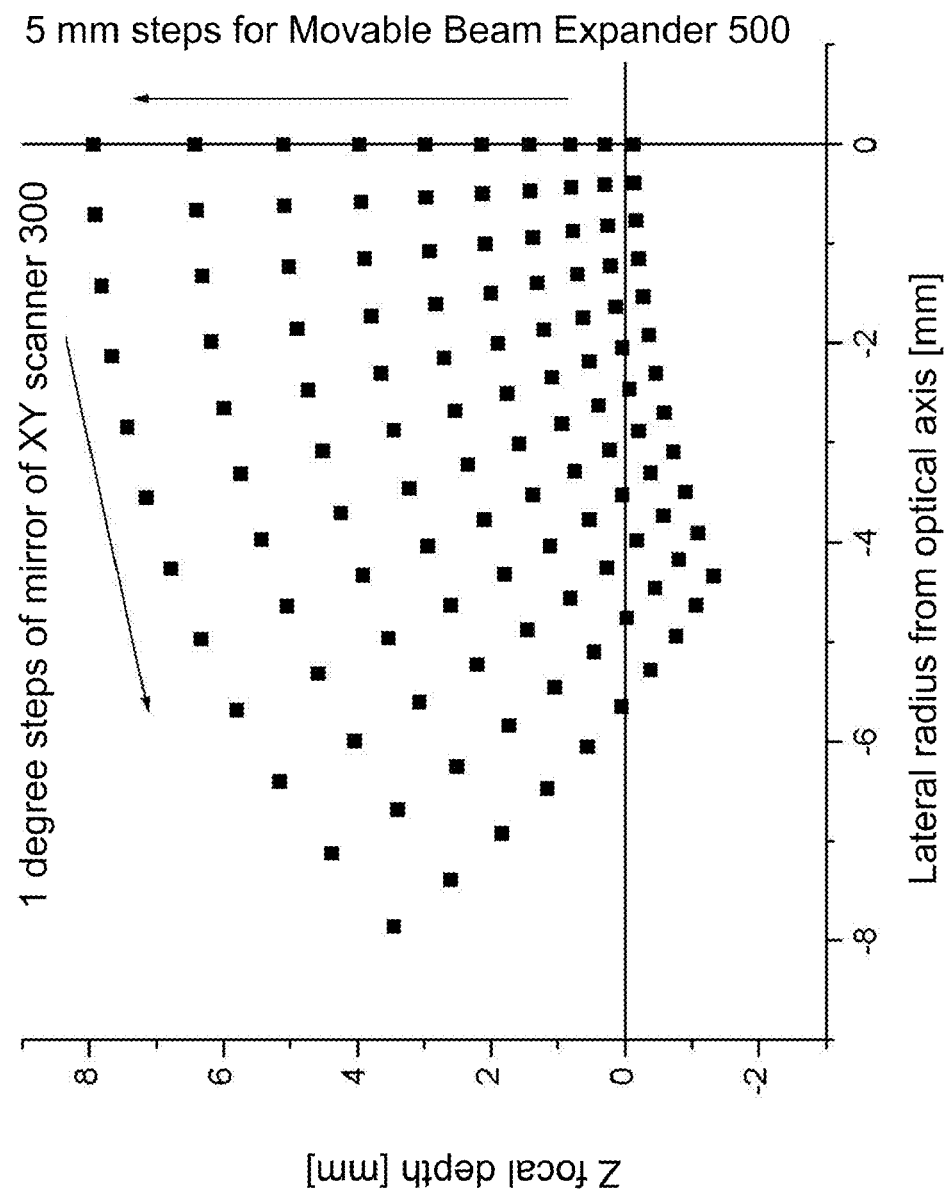
FIG. 16 illustrates a curved focal plane in the target region.

FIG. 16 illustrates that in some systems this design principle would render the positional accuracy of the surgical system less advantageous. The square dots indicate the position of the focal spot as a mirror of the XY Scanner 300 scans in 1 degree steps and the Z Scanner 450 scans the Z focal depth by moving the Movable Beam Expander 500 in 5 mm steps. Visibly, the "focal plane", defined as the XY scanned locations of the focal spot while the keeping the Z focal depth constant, is curved. At the lateral periphery the cutting depth is shallower, consistent with the known behavior of lenses with uncorrected field curvature.

Likewise, if the mirrors of the XY Scanner 300 are kept fixed and the Z Scanner 450 scans the Z focal depth, the lateral position of the focal spot changes. Further complicating the design, neither the radial lateral XY position nor the Z focal depth exhibits a linear dependence on the respective scanner positions. In the XY plane these distortions are called barrel or pincushion distortions. (In many implementations, the third coordinate, the azimuth angle of the XY Scanner 300 transfers unchanged to the azimuth angle of the focal positions, and hence will be suppressed.)

Figure 17:
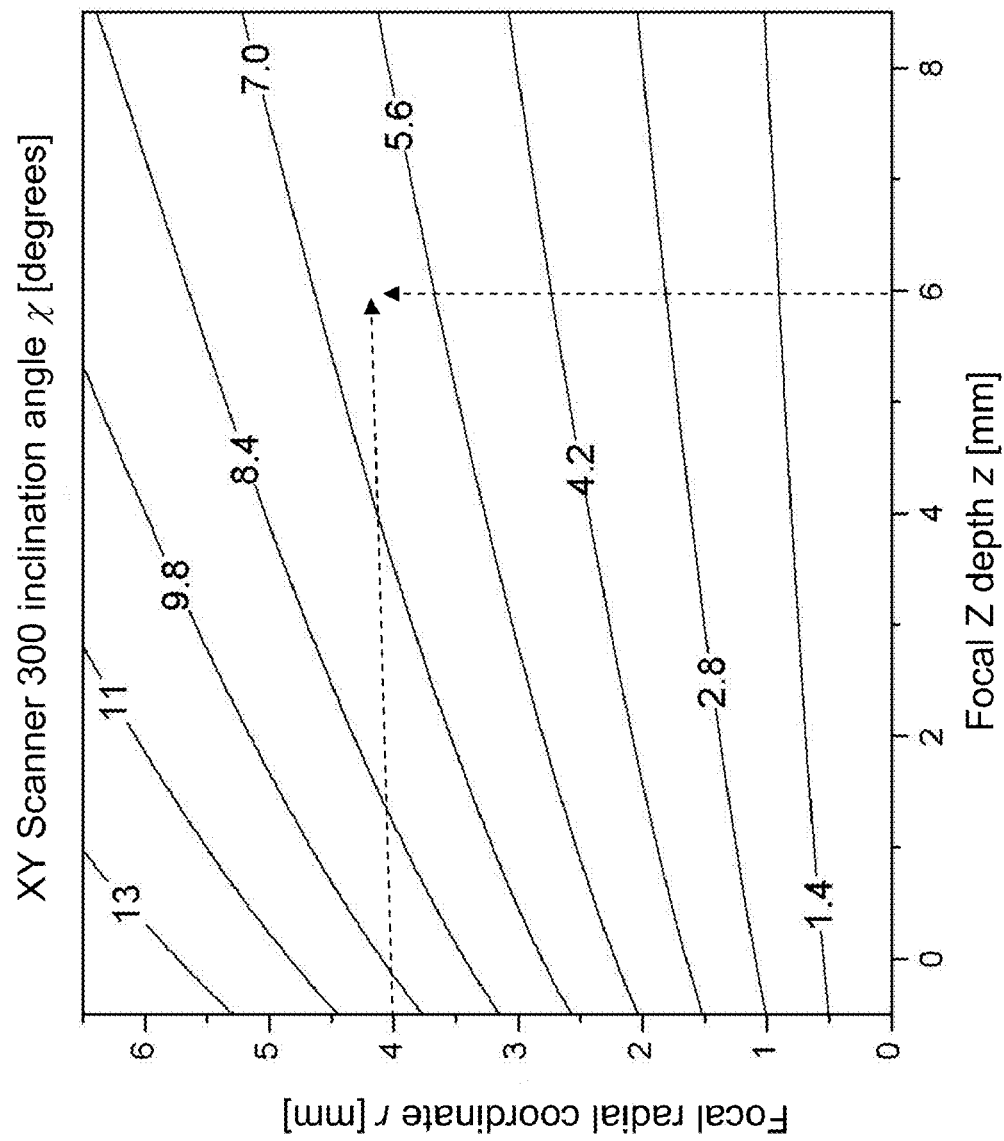
FIG. 17 illustrates a nomogram of the XY Scanner inclination angle.

FIG. 17 illustrates how some implementations of the laser delivery system 1 offer new, computational solutions to the described challenges. The scanner coordinates are given in spherical coordinates $(\zeta, \chi, \phi)$, where $\zeta$ is the position of the Z Scanner 450, $\chi$ is an inclination angle of the XY Scanner 300 from the optical axis, and $\phi$ is the azimuth angle. The focal spot positions are given by the cylindrical focal coordinates $(z, r, \phi)$, z being the Z focal depth, r the radial distance from the optical axis, and $\phi$ the azimuth angle.

The azimuth angle of the focal position can be essentially the same as the azimuth angle of the scanners and thus is not shown. The remaining XY and the Z scanner coordinates $(\zeta, \chi)$ can be discretized within their respective scanning intervals, defining a scanning grid and a corresponding scanner matrix $C_{ij}$, defined as $C_{ij}=(\zeta_i, \chi_j)$. If the actual scanner coordinates assume a value $(\zeta_{i0}, \chi_{j0})$, then the scanning matrix $C_{ij}$ is 1 at this particular (i0, j0) pair and zero for all other (i, j) pairs.

Similarly, the focal spot positions can be characterized by a two dimensional focal matrix $S_{kl}$, where $S_{kl}$ is related to the discretized radial and Z depth focal coordinates $(z_k, r_l)$. In terms of the scanner matrix $C_{ij}$ and focal matrix $S_{kl}$, the optical performance of the laser delivery system 1 can be characterized with a four dimensional transfer matrix $T_{ijkl}$, which expresses how the scanner coordinates $(\zeta_i, \chi_j)$ transform onto the focal coordinates $(z_k, r_l)$ in general: S=TC, or in detail:

$$S_{kl} = \sum_{ij} T_{klij} C_{ij} \quad (5)$$

While the transfer matrix $T_{ijkl}$ represents a linear connection between the scanner matrix $C_{ij}$ and focal matrix $S_{kl}$, in some other implementations a non-linear relationship may exist between the scanner matrix $C_{ij}$ and focal matrix $S_{kl}$. In those implementations Eq. (5) is replaced by a non-linear connection.

The laser delivery system 1 can be designed to optimize the elements of the transfer matrix T by computational ray tracing, physical calibration, or a combination of both. An implementation of a physical calibration method is described in US Patent Application US20090131921, which could be used for such a purpose.

Typically, the transfer matrix T is invertible and can be used to create the inverse transfer matrix, $T^{-1}$, which connects elements of the focal matrix $S_{kl}$ to the scanner matrix $C_{ij}$.

Alternatively, in some embodiments the inverse transfer matrix $T^{-1}$ can be determined directly by starting a computational design process with the desired focal matrix $S_{kl}$ in the target region and use e.g. ray tracing to reconstruct the corresponding scanner matrix $C_{ij}$.

Figure 18:
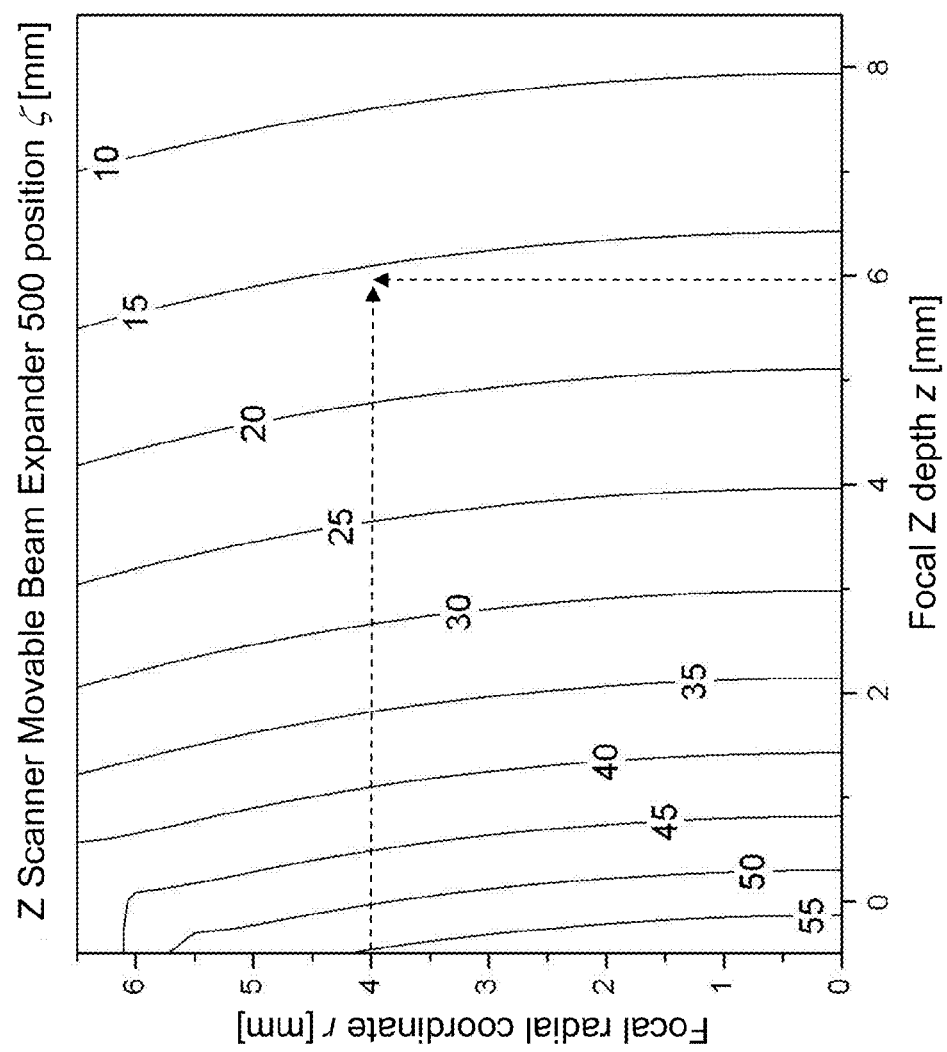
FIG. 18 illustrates a nomogram of the Movable Beam Expander position.

FIGS. 17-18 illustrate such relations. These FIGS. are nomograms, illustrating which $(\zeta_i, \chi_j)$ scanner coordinates the XY Scanner 300 or the Z Scanner 450 can be tuned to in order to focus the beam to the $(z_k, r_l)$ focal coordinates, shown on the z and r axes.

FIG. 17 shows the $\chi$ inclination angle of the XY Scanner 300, corresponding to the (z, r) focal coordinates. As an example, to achieve a Z depth of z=6 mm and a radial position of r=4 mm, the dashed lines indicate that an XY scanner inclination angle of $\chi$=6.4 degrees can be used.

FIG. 18 shows that, to achieve the same (z, r)=(4, 6) focal coordinates, a Z scanner position $\zeta$=15.5 mm can be used. Computationally, the nomograms can be stored in a computer memory as look-up tables. Values in between stored look-up coordinates can be quickly determined by two dimensional linear or quadratic interpolation.

Knowledge of the transfer matrix T and its inverse $T^{-1}$ allow embodiments of the laser delivery system 1 to correct the aberrations of FIG. 16 by computational methods instead of optical methods. These embodiments may include a computational controller, which can control at least one of the XY Scanner 300 and the Z Scanner 450 to control an optical distortion of the laser delivery system 1.

FIG. 19 illustrates that, for example, if scanning along a scanning pattern with reduced optical distortion is desired in a target region, e.g. along a flat focal plane at a predetermined Z focal depth z, the computational controller can perform the steps of the following computational control method 900:

(910): receiving at least one of input $(z_k, r_l)$ focal coordinates and elements of a focal matrix $S_{kl}$ corresponding to a scanning pattern with reduced optical distortion in the target region;

(920): computing, or recalling from a stored memory at least one of the $(\zeta_i, \chi_j)$ scanner coordinates and the elements of the scanner matrix $C_{ij}$, corresponding to the input $(z_k, r_l)$ focal coordinates or elements of the focal matrix $S_{kl}$, using a predetermined inverse transfer matrix $(T^{-1})_{ijkl}$; and (930): controlling at least one of the Z Scanner 450 and the XY Scanner 300 according to the computed $(\zeta_i, \chi_j)$ scanner coordinates to scan the focal spot according to the input $(z_k, r_l)$ focal coordinates or elements of the focal matrix $S_{kl}$.

Laser delivery systems having such a computational controller can reduce an optical distortion relative to the same or similar laser systems without such controllers. The degree of reduction may be as much as 10% in some embodiments, and as much as 30% in other embodiments.

The reduced optical distortion can be any one of an aberration, a field curvature, a barrel distortion, a pincushion distortion, a curved focal plane, and a bent scanning line, intended to be parallel to the Z axis.

In some implementations, the computational controller performs these functions in cooperation with the other blocks of the laser delivery system, including the Precompensator 200, the XY Scanner 300, the Z Scanner 450 and the Objective 700, possibly utilizing any of their above described features.

The number of possible analogous implementations is very large, relying on the principle of computational control to reduce optical aberrations. E.g. the computational controller in some embodiments can be capable to scan the focal spot over a focal plane with a curvature below a critical curvature value. In some other implementations surfaces with predetermined shapes can be scanned with an appropriate operation of the computational controller.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

A number of implementations of imaging-guided laser surgical techniques, apparatus and systems are disclosed. However, variations and enhancements of the described implementations, and other implementations can be made based on what is described.

The invention claimed is:

1. A laser system for ophthalmic surgery, comprising:
a laser source, to generate a pulsed laser beam;
an XY scanner,
  to receive the pulsed laser beam, and
  to output an XY-scanning beam, scanned in two directions transverse to a Z axis;
a Z scanner,
  to receive the XY-scanning beam; and
  to output an XYZ-scanning beam, scanned in addition along the Z axis;
the Z scanner comprising
  a first lens group to output a beam having an intermediate focal plane; and
  a movable lens group to receive the beam through the intermediate focal plane and to collimate the beam in a variable manner; and
an objective to receive the collimated beam from the Z scanner and to focus the beam into a focal spot in a target region.

2. The ophthalmic laser system of claim 1, wherein:
the Z scanner is configured to scan a Z focal depth of the focal spot in the target region within a Z scanning range of 5 millimeter to 10 millimeter.

3. The ophthalmic laser system of claim 1, wherein:
the Z scanner is configured to scan a Z focal depth of the focal spot in the target region within a Z scanning range of 0 millimeter to 15 millimeter.

4. The ophthalmic laser system of claim 1, wherein
the movable lens group can be moved along the Z axis by a distance between 5 and 50 millimeters.

5. The ophthalmic laser system of claim 1, wherein:
the first lens group comprises 2-10 lenses; and
the movable lens group comprises 2-10 lenses.

6. The ophthalmic laser system of claim 1, wherein:
the first lens group comprises, sequentially from an input side
  a first lens group with a positive refractive power;
  a meniscus lens, having a convex surface facing the input side; and
  a second lens, having a concave surface facing the input side.

7. The ophthalmic laser system of claim 1, wherein:
the first lens group has five lenses, the lenses having indices of refraction and sequentially labeled surfaces with corresponding curvatures, all within ranges given in the following table:

| Surface | Curvature [1/m] | Distance [mm] | Refractive Index n |
|---|---|---|---|
| 1 | (0, 1.5) | (5, 25) | (1.6, 1.93) |
| 2 | (22, 28) | (12, 22) | (1.6, 1.7) |
| 3 | (−17, −14) | (0.5, 12) | 1 |
| 4 | (7.0, 8.5) | (15, 29) | (1.65, 1.8) |
| 5 | (−19, −13) | (3, 14) | 1 |
| 6 | (14, 18) | (8, 12) | (1.6, 1.7) |
| 7 | (0, 9.3) | (6, 12) | 1 |
| 8 | (−28, −21) | (1, 5) | (1.65, 1.75) |
| 9 | (−15, −6) | | |

8. The ophthalmic laser system of claim 7, wherein:
the first lens group has five scaled lenses in place of the five lenses, having scaled curvatures corresponding to the curvatures of the five lenses multiplied by a scale factor $\alpha$ and scaled distances in place of the distances, scaled by a scale factor $1/\alpha$, wherein
the scale factor $\alpha$ has a value between 0.3 and 3.

9. The ophthalmic laser system of claim 1, wherein:
the movable lens group comprises, sequentially from an input side
  a meniscus lens, having a concave surface facing the input side;
  a negative lens with a negative refractive power; and
  a positive lens group with a positive refractive power.

10. The ophthalmic laser system of claim 1, wherein:
the movable lens group has four lenses, the lenses having indices of refraction and sequentially labeled surfaces with corresponding curvatures, all within ranges given in the following table:

| Surface | Curvature [1/m] | Distance [mm] | Refractive Index n |
|---|---|---|---|
| 1 | (−25, −10) | (3, 7) | (1.7, 1.8) |
| 2 | (−25, −28) | (0, 2) | 1 |
| 3 | (−43, −24) | (1.5, 5) | (1.5, 1.62) |
| 4 | (8.5, 19.4) | (26, 31) | 1 |
| 5 | (−6.2, −4.6) | (10, 16) | (1.53, 1.6) |
| 6 | (−18.4, −14.7) | (34, 49) | 1 |
| 7 | (1.9, 4.2) | (8, 14) | (1.58, 1.61) |
| 8 | (−11, −9.0) | | |

11. The ophthalmic laser system of claim 10, wherein:
the movable lens group has four scaled lenses in place of the four lenses, having scaled curvatures corresponding to the curvatures of the four lenses multiplied by a scale factor α and scaled distances in place of the distances, scaled by a scale factor 1/α, wherein
the scale factor α has a value between 0.3 and 3.

12. The ophthalmic laser system of claim 1, wherein:
the movable lens group is adjustable to change at least one characteristic of the XYZ scanning beam exiting the Z scanner, the characteristics comprising:
a convergence, a beam diameter, a Z focal depth, and a numerical aperture NA.

13. The ophthalmic laser system of claim 1, wherein:
the movable lens group is configured to adjust a numerical aperture NA and a Z focal depth of the XYZ scanning beam essentially independently from each other.

14. The ophthalmic laser system of claim 1, wherein:
the Z scanner is configured to focus a beam, emanating from an exit pivot point of the XY scanner into an entrance pivot point of the objective.

15. The ophthalmic laser system of claim 14, wherein:
the entrance pivot point of the objective is inside the objective.

16. The ophthalmic laser system of claim 14, wherein:
a position of the entrance pivot point of the objective is adjustable by moving the movable lens group.

17. The ophthalmic laser system of claim 1, wherein:
the Z scanner is configured to modify an exit pivot point of the XY scanner into an entrance pivot point of the objective.

18. The ophthalmic laser system of claim 17, wherein:
the entrance pivot point of the objective is inside the objective.

19. The ophthalmic laser system of claim 1, wherein:
the first lens group is one of a movable lens group and a fixed lens group.

20. A method of ophthalmic surgery, the method comprising the steps of:
generating a pulsed laser beam;
XY scanning the pulsed laser beam in two directions transverse to a Z direction with an XY scanner;
Z scanning the XY scanned beam along a Z direction with a Z scanner by
focusing the XY scanned beam onto an intermediate focal plane with a first lens group;
receiving the beam from the intermediate focal plane by a movable beam scanner;
collimating the beam into an adjustable entrance pivot point of an objective by the movable beam scanner; and
focusing the beam onto an XYZ scanned focal spot in a target region by the objective.

21. The method of claim 20, wherein the Z scanning step comprises:
adjusting the movable beam scanner to change at least one characteristic of the XYZ scanning beam exiting the Z scanner, the characteristics comprising:
a convergence, a beam diameter, a Z focal depth, and a numerical aperture NA.

22. The method of claim 20, wherein the Z scanning step comprises:
adjusting a numerical aperture NA and a Z focal depth of the XYZ scanning beam essentially independently from each other.

* * * * *